(12) United States Patent
Hill et al.

(10) Patent No.: US 7,459,445 B2
(45) Date of Patent: *Dec. 2, 2008

(54) ESTROGENIC COMPOUNDS AND TOPICAL PHARMACEUTICAL FORMULATIONS OF THE SAME

(75) Inventors: Edward N. Hill, Wilmington, NC (US); Frederick D. Sancilio, Wilmington, NC (US); Robert R. Whittle, Wilmington, NC (US)

(73) Assignee: Duramed Pharmaceuticals, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/671,718

(22) Filed: Feb. 6, 2007

(65) Prior Publication Data

US 2007/0142307 A1    Jun. 21, 2007

Related U.S. Application Data

(63) Continuation of application No. 10/628,057, filed on Jul. 23, 2003, now Pat. No. 7,179,799.

(51) Int. Cl.
*A61K 31/56* (2006.01)
*C07J 1/00* (2006.01)

(52) U.S. Cl. .................. 514/182; 514/171; 514/178; 552/615

(58) Field of Classification Search .............. 552/615; 514/171, 178, 182
See application file for complete search history.

(56) References Cited

U.S. PATENT DOCUMENTS

| | | | | |
|---|---|---|---|---|
| 3,230,142 A | 1/1966 | Spero | ............. | 167/55 |
| 3,487,152 A | 12/1969 | Carstensen et al. | .......... | 424/240 |
| 3,502,772 A | 3/1970 | Ijzerman | ............. | 424/239 |
| 3,568,828 A | 3/1971 | Lerner | ............. | 206/42 |
| 3,591,688 A | 7/1971 | Jones et al. | ............. | 424/239 |
| 3,639,600 A | 2/1972 | Hendrix | ............. | 424/242 |
| 3,733,407 A | 5/1973 | Segre | ............. | 424/239 |
| 3,795,734 A | 3/1974 | Rochefort | ............. | 424/238 |
| 3,813,418 A | 5/1974 | Hofmeister et al. | ............. | 260/397.4 |
| 3,836,651 A | 9/1974 | Rudel et al. | ............. | 424/239 |
| 3,932,635 A | 1/1976 | Segre | ............. | 424/239 |
| 3,939,264 A | 2/1976 | Lachnit-Fixson | ............. | 424/239 |
| 3,942,641 A | 3/1976 | Segre | ............. | 206/534 |
| 3,957,982 A | 5/1976 | Lachnit-Fixson et al. | ... | 424/238 |
| 3,969,502 A | 7/1976 | Lachnit-Fixson | ............. | 424/239 |
| 4,027,019 A | 5/1977 | Shroff | ............. | 424/238 |
| 4,066,757 A | 1/1978 | Pasquale | ............. | 424/243 |
| 4,071,623 A | 1/1978 | van der Vies | ............. | 424/238 |
| 4,145,416 A | 3/1979 | Lachnit-Fixson et al. | ... | 424/238 |
| 4,147,783 A | 4/1979 | van der Vies | ............. | 424/243 |
| 4,154,820 A | 5/1979 | Simoons | ............. | 424/175 |
| 4,210,644 A | 7/1980 | Ewing et al. | ............. | 424/239 |
| 4,259,325 A | 3/1981 | Prezewowsky et al. | ...... | 424/238 |
| 4,291,028 A | 9/1981 | Vorys | ............. | 424/238 |
| 4,292,315 A | 9/1981 | Vorys | ............. | 424/240 |
| 4,315,925 A | 2/1982 | Hussain et al. | ............. | 424/239 |
| 4,327,725 A | 5/1982 | Cortese et al. | ............. | 128/260 |
| 4,378,356 A | 3/1983 | De Jager | ............. | 424/238 |
| 4,383,993 A | 5/1983 | Hussain et al. | ............. | 424/239 |
| 4,390,531 A | 6/1983 | Edgren | ............. | 424/239 |
| 4,425,339 A | 1/1984 | Pitchford | ............. | 424/239 |
| 4,512,986 A | 4/1985 | Reel et al. | ............. | 514/170 |
| 4,530,839 A | 7/1985 | Pasquale | ............. | 514/171 |

(Continued)

FOREIGN PATENT DOCUMENTS

DE    2431694 A1    3/1976

(Continued)

OTHER PUBLICATIONS

Andreolini, et al., *Estrogen Conjugates in Late-Pregnancy Fluids: Extraction and Group Separation by a Graphitized Carbon Black Cartridge and Quantification by High-Performance Liquid Chromatography*, Anal. Chem. 59:1720-1725 (1987).

(Continued)

*Primary Examiner*—Barbara P Badio
(74) *Attorney, Agent, or Firm*—Myers Bigel Sibley & Sajovec, PA

(57) ABSTRACT

Novel estrogenic compounds of Formula I are provided.

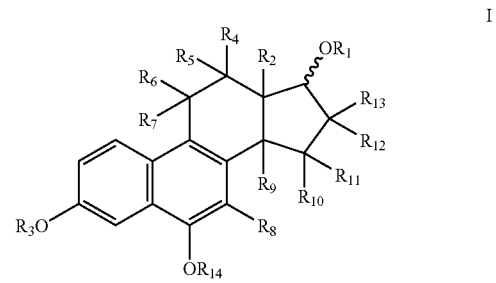

wherein the bond represented by the wavy line may be a single or double bond such that when the wavy line is a single bond, $R_1$ is selected from the group consisting of hydrogen, sulfate and glucoronate or other esters, and when the wavy line is a double bond, $R_1$ does not exist; $R_2$ is lower alkyl; $R_3$ may be selected from the group consisting of hydrogen, sulfate, or glucuronide or other esters; and $R_4$ through $R_{13}$ may independently be selected from the group consisting of hydrogen, hydroxy, ketone, lower alkyl, lower alkoxy, halogen, and carbonyl groups and $R_{14}$ is selected from the group consisting of hydrogen, sulfate and glucoronide and other esters. When $R_1$ is hydroxy, the hydroxy or ester substituent may have either an α or a β orientation. Compositions of matter including compounds of the present invention are also provided as are methods of treating mammals in need of treatment using compounds of the present invention.

14 Claims, 47 Drawing Sheets

U.S. PATENT DOCUMENTS

| | | | |
|---|---|---|---|
| 4,544,554 A | 10/1985 | Pasquale | 514/170 |
| 4,616,006 A | 10/1986 | Pasquale | 514/170 |
| 4,621,079 A | 11/1986 | Lachnit-Fixson et al. | 514/170 |
| 4,628,051 A | 12/1986 | Pasquale | 514/170 |
| 4,738,957 A | 4/1988 | Laurent et al. | 514/182 |
| 4,756,907 A | 7/1988 | Beck et al. | 424/85 |
| 4,762,717 A | 8/1988 | Crowley, Jr. | 424/425 |
| 4,764,378 A | 8/1988 | Keith et al. | 424/435 |
| 4,783,337 A | 11/1988 | Wong et al. | 424/468 |
| 4,816,257 A | 3/1989 | Buster et al. | 424/430 |
| 4,816,258 A | 3/1989 | Nedberge et al. | 424/448 |
| 4,826,831 A | 5/1989 | Plunkett et al. | 514/170 |
| 4,855,305 A | 8/1989 | Cohen | 514/171 |
| 4,900,734 A | 2/1990 | Maxson et al. | 514/171 |
| 4,914,089 A | 4/1990 | Tax | 514/170 |
| 4,921,843 A | 5/1990 | Pasquale | 514/170 |
| 4,962,098 A | 10/1990 | Boissonneault | 514/170 |
| 4,977,147 A | 12/1990 | Jungblut et al. | 514/171 |
| 5,006,345 A | 4/1991 | Lang | 424/467 |
| 5,010,070 A | 4/1991 | Boissonneault | 514/171 |
| 5,043,331 A | 8/1991 | Hirvonen et al. | 514/170 |
| 5,089,482 A | 2/1992 | Hermens et al. | 514/58 |
| 5,098,714 A | 3/1992 | Wright et al. | 424/473 |
| 5,108,995 A | 4/1992 | Casper | 514/170 |
| 5,130,137 A | 7/1992 | Crowley, Jr. | 424/422 |
| 5,183,814 A | 2/1993 | Dukes | 514/171 |
| 5,200,197 A | 4/1993 | Wright et al. | 424/473 |
| 5,208,225 A | 5/1993 | Boissonneault et al. | 514/178 |
| 5,210,081 A | 5/1993 | Raveendranath et al. | 514/179 |
| 5,262,408 A | 11/1993 | Bergink | 514/182 |
| 5,276,022 A | 1/1994 | Casper | 514/170 |
| 5,280,023 A | 1/1994 | Ehrlich et al. | 514/177 |
| 5,288,717 A | 2/1994 | Raveendranath et al. | 514/179 |
| 5,362,720 A | 11/1994 | Labrie | 514/169 |
| 5,382,573 A | 1/1995 | Casper | 514/170 |
| 5,418,228 A | 5/1995 | Bennink | 514/182 |
| 5,434,146 A | 7/1995 | Labrie et al. | 514/169 |
| 5,464,871 A | 11/1995 | Kun et al. | 514/617 |
| 5,510,342 A | 4/1996 | Washburn et al. | 514/179 |
| 5,541,172 A | 7/1996 | Labrie | 514/169 |
| 5,545,634 A | 8/1996 | Labrie | 514/169 |
| 5,547,948 A | 8/1996 | Barcomb | 514/170 |
| 5,567,695 A | 10/1996 | Labrie | 514/169 |
| 5,629,303 A | 5/1997 | Labrie et al. | 514/169 |
| 5,654,011 A | 8/1997 | Jackson et al. | 424/635 |
| 5,753,639 A | 5/1998 | Labrie | 514/169 |
| 5,759,576 A | 6/1998 | Barcomb | 424/479 |
| 5,759,577 A | 6/1998 | Barcomb | 424/479 |
| 5,807,586 A | 9/1998 | Jackson et al. | 424/630 |
| 5,846,960 A | 12/1998 | Labrie | 514/169 |
| 5,861,387 A | 1/1999 | Labrie et al. | 514/169 |
| 5,861,431 A | 1/1999 | Hildebrand et al. | 514/557 |
| 5,908,638 A | 6/1999 | Huber et al. | 424/465 |
| RE36,247 E | 7/1999 | Plunkett et al. | 514/170 |
| 5,998,639 A | 12/1999 | Raijmakers et al. | 552/625 |
| 6,040,333 A | 3/2000 | Jackson | 514/456 |

FOREIGN PATENT DOCUMENTS

| | | |
|---|---|---|
| DE | 2624025 A1 | 12/1976 |
| DE | 3341638 A1 | 11/1983 |
| GB | 1214712 | 12/1970 |
| GB | 1561244 | 2/1980 |
| GB | 2096462 A | 10/1982 |
| IL | 25265 | 12/1969 |

OTHER PUBLICATIONS

Fujino, et al., 3-(*Difluoro-1,3.5-trianinyl*)-1-(ethylthio)-2-n-propylbenz[f]isoindole as a Fluorescence Derivation Reagent for Estrogens in High-Performance Liquid Chromatography, Chem. Pharm. Bull., 37(7): 1939-1940 (1989).

Vest, Floyd B. & Karnes, H. Thomas, *Luminescent Derivation of Estrogens for HPLC Detection* (Abstract), Department of Pharmacy and Pharmaceutics, Medical College of Virginia, APQ 1198, ref. needed.

Takadate, et al., *A Convenient Derivatization with Anion Exchange Resin Catalysis for High-Performance Liquid Chromatographic Analysis. 1. Derivatization of Estrogens with Dansyl Chloride*, Chem. Pharm. Bull., 33(11): 5092-5095 (1985).

Novakovic, et al., *High-Performance Liquid Chromatographic Determination of Equine Estrogens with Ultraviolet Absorbance and Electrochemical Detection*, Journal of Chromatography A, 678: 359-363 (1994).

Townsend, et al., *High-Performance Liquid Chromatographic Determination of Conjugated Estrogens in Tablets*, Journal of Chromatography, 450: 414-419 (1988).

Ishida, et al., *Determination of Oestrogens in Pregnancy Urine by High-Performance Liquid Chromatography with Fluorescence Detection*, Journal of Chromatography, 431: 249-257 (1988).

*Conjugated Estrogens*, The United States Pharmacopeia (USP), published by United States Pharmacopeial Convention, Inc., pp. 627-629 (2000).

Synthetic Generic Conjugated Estrogens: Timeline, May 5, 1997, <http://www.fda.gov/cder/news/cetimeline.htm>.

FDA Statement on Generic Premarin, HHS News Press Release, P97-12, May 5, 1997, <http://www.fda.gov/cder/cepressrelease.htm>.

New Drug Approval for Cenestin, Synthetic Conjugated Estrogens, A: Mar. 24, 1999, *Questions and Answers*, <http://www.fda.gov/cder/news/cenestin/qa.htm>.

NDA 20-992 Cenestin™ (synthetic conjugated estrogens, A) Tablets Physicians Package Insert, pp. 1-10 (1999).

NDA 20-992 Cenestin™ (synthetic conjugated estrogens, A) Tablets Patient Package Insert, pp. 11-13 (1999).

FDA Backgrounder on Conjugated Estrogens, May 5, 1997, <http://www.fda.gov/cder/cebackground.htm>.

Letter from Yana Ruth Mille, Chief, Compendial Operations Staff, HFD-354, Office of Pharmaceutical Science, Center for Drug Evaluation & Research to Joseph G. Valentino, J.D., Senior Vice President and General Counsel, The United States Pharmacopeial Convention, Inc. (Mar. 8, 2000) (REF: 3-00-001-O).

Letter from Yana Ruth Mille, Chief, Compendial Operations Staff, HFD-354, Office of Pharmaceutical Science, Center for Drug Evaluation & Research to Joseph G. Valentino, J.D., Senior Vice President and General Counsel, The United States Pharmacopeial Convention, Inc. (Mar. 8, 2000) (REF: 3-00-002-O).

Memorandum from Janet Woodcock, M.D., Director, Center for Drug Evaluation & Research to Douglas L. Sporn, Director, Office of Generic Drugs, regarding Approvability of a Synthetic Generic Version of Premarin (May 5, 1997).

Sakac, Marijan N. et al., "Chemical Behavior of 3, 17.beta.-dipropionoxy-9.alpha.-hydroxyestra-1,3,5(10)-trien-6-one," *Database CHEMABS 'Online!*, Database accession No. 128:180573 XP002171996, J. Serb. Chem. Soc., 63(1): 21-24 (1998).

Wiese, Thomas et al., "Induction of the Estrogen Specific Mitogenic Response of MCF-7 Cells by Selected Analogues of Estradiol-17β: A 3D Study," *Journal of Medicinal Chemistry*, 40(22): 3659-3669 (1997).

Yang et al., "The Hydroxylation and Amidation of Equilenin Acetate Catalyzed by Chloro[5,10,15,20-tetrakis(pentafluorophenyl)porphyrinato]manganese(III)," *Chem. Commun.*, 7: 531-532 (2000).

Yang, Jerry et al., "Regioselective Oxidations of Equilenin Derivatives Catalyzed by a Rhodium(III) Porphyrin Complex-Contrast with the Manganese(III) Porphyrin," *Tetrahedron Letters*, 41(42): 8063-8067 (2000).

Rzheznikov, V.M. et al., "Synthesis and Biological Activity of Estrone 8-iso- and D-homoanalogs Oxidized for Rings B and C," *Database CHEMABS 'Online!*, Database accession No. 110:108353 XP002171997, Khim.-Farm. Zh. 22(12): 1462-1465 (1988).

Sakac, Marija N. et al., "Synthesis of New Steroidal N-butyl-N-methyl-undecanamide Derivatives," *Database CHEMABS 'Online!*, Database accession No. 133:335378 XP002171995, ZB. Matice SRP. PRIR. NAUKE 96: 5-9 (1999).

Center for Drug Evaluation and Research (CDER),Guidance for Industry, Draft Guidance, *Conjugated Estrogens. USP—LC-MS Method for Both Qualitative Chemical Characterization and Documentation of Qualitative Pharmaceutical Equivalence,* Mar. 2000, <http://www.fda.gov/cder/guidance/index.htm>.

Physician's Desk Reference 53: 3367-3379 (1999).

ESTROGENIC COMPOUNDS AND TOPICAL PHARMACEUTICAL FORMULATIONS OF THE SAME

CROSS REFERENCE TO RELATED APPLICATION

The present application is a continuation application of U.S. patent application Ser. No. 10/628,057, filed Jul. 23, 2003, now U.S. Pat. No. 7,179,799, which claims priority to U.S. patent application Ser. No. 09/800,614, filed Mar. 8, 2001, now U.S. Pat. No. 6,660,726, which in turn, claims priority to U.S. Provisional Application Ser. No. 60/188,523, filed Mar. 10, 2000. The disclosures of each of which are hereby incorporated by reference in their entireties.

FIELD OF THE INVENTION

The present invention relates to the isolation of estrogenic compounds.

BACKGROUND OF THE INVENTION

Women, particularly menopausal and post-menopausal women, often experience a wide variety of conditions and disorders attributable to estrogen deprivation. Estrogen deprivation is most often the result of loss of ovarian function. Exemplary conditions are hot flashes, dryness of the vagina, including discomfort during intercourse, loss of bone mass, increased heart disease and the like.

Providing dosages of estrogen is an effective agent for the control or prevention of such conditions, particularly in controlling or preventing hot flashes and vaginal atrophy, along with retarding or preventing osteoporosis. Estrogen is typically administered alone or in combination with a progestin.

As detailed in U.S. Pat. No. Re. 36,247 to Plunkett et al., estrogen alone, given in small doses, on a continuous basis, is effective in most patients for the control of the above symptoms and problems associated therewith. However, although the vast majority of women taking continuous low-dose estrogen will not have bleeding for many months or even years, there is a distinct risk posed by this routine of silently (i.e. exhibiting no overt symptoms) developing "hyperplasia of the endometrium". This term refers, of course, to an overstimulation of the lining of the uterus which can become pre-malignant, coupled with the possibility that the patient may eventually develop cancer of the uterine lining even under such a low-dose regimen (Gusberg et al., Obstetrics and Gynaecology, 17, 397-412, 1961).

Estrogen alone can also be given in cycles, usually 21-25 days on treatment and 5-7 days off treatment. Again, if small doses of estrogen are required to control the symptoms and it is used to this fashion, only about 10% of women will experience withdrawal bleeding between the cycles of actual treatment. However, one must again be concerned by the risk of developing endometrial hyperplasia and by the increased relative risk of developing cancer of the uterus (Research on the Menopause: Report of a W.H.O. Scientific Group, 53-68, 1981).

The addition of progestin for the last 7-10 days of each estrogen cycle may virtually eliminate the concern about developing endometrial hyperplasia and/or also reduce the risk of developing endometrial carcinoma below that of the untreated general population. However, withdrawal bleeding may occur regularly in this routine and this is highly unacceptable to most older women (Whitehead, Am. J. Obs/Gyn., 142,6, 791-795, 1982).

Still another routine for estrogen administration may involve a formulation such as those found in birth control pills which contain relatively small doses of estrogen over the full 20-21 day treatment cycle, plus very substantial doses of potent progestins over the same period of time. This routine, of course not only produces withdrawal bleeding on each cycle, but is further unacceptable because such formulations have been shown to carry an increased risk of developing arterial complications, such as stroke or myocardial infarction in older women about the age of 35-40. This is especially true if the individual is a smoker of cigarettes (Plunkett, Am. J. Obs/Gyn. 142, 6, 747-751, 1982). There, however, remains a need for novel isolated estrogenic compounds.

SUMMARY OF THE INVENTION

Thus, as one aspect of the present invention, a compound represented by Formula I is provided.

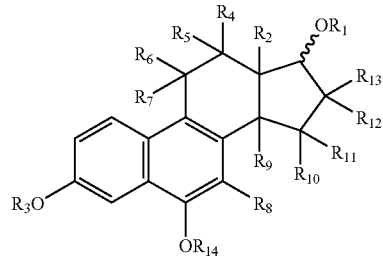

where the bond represented by the wavy line may be a single or double bond such that when the wavy line is a single bond, $R_1$ may be selected from the group consisting of hydrogen, sulfate and glucoronide or other esters, and when the wavy line is a double bond, $R_1$ does not exist; $R_2$ is lower alkyl; $R_3$ may be selected from the group consisting of hydrogen, sulfate, and glucoronide or other esters; and $R_4$ through $R_{13}$ may independently be selected from the group consisting of hydrogen, hydroxy, ketone, lower alkyl ($C_1$ to $C_4$), lower alkoxy ($C_1$ to $C_4$), halogen, and carbonyl groups. When $R_1$ is hydroxy, the hydroxy or ester substituent may have either an $\alpha$ or a $\beta$ orientation, with the $\beta$ orientation being preferred. $R_2$ is preferably $C_1$ to $C_4$ alkyl, and more preferably is methyl. $R_4$ through $R_{12}$ are preferably hydrogen. $R_{13}$ is preferably hydrogen or ethynyl. $R_{14}$ is hydrogen, sulfate, or glucoronide and other esters.

The compound represented by Formula I may be present in chemically pure form, namely greater than about 90% pure, preferably greater than about 95% pure, and most preferably greater than about 99% pure.

A preferred compound is illustrated in Formula II:

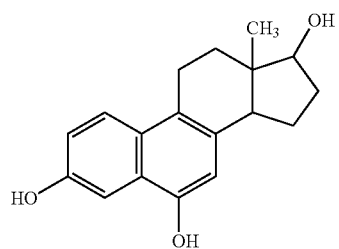

Another preferred compound is illustrated in Formula III:

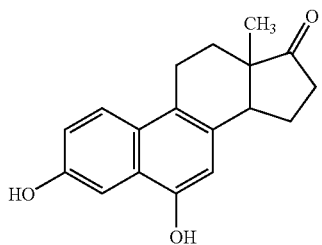

III

In another aspect, the present invention provides a composition of matter. The composition of matter comprises a compound according to the present invention.

In still another aspect, the invention provides a method of treating mammals in need of treatment. The method comprises administering an effective amount of a composition of matter according to the present invention. Examples of treatments that are addressed by the compositions of the invention include vasomotor symptoms, atrophic vaginitis, and osteoporosis.

The invention is described in greater detail with respect to the preferred embodiments set forth hereinbelow.

BRIEF DESCRIPTION OF THE DRAWINGS

The accompanying drawings which are incorporated in and constitute a part of the specification, illustrate embodiments of the invention and, together with the description, serve to explain principles of the invention.

DETAILED DESCRIPTION OF THE PREFERRED EMBODIMENTS

Figure 1:
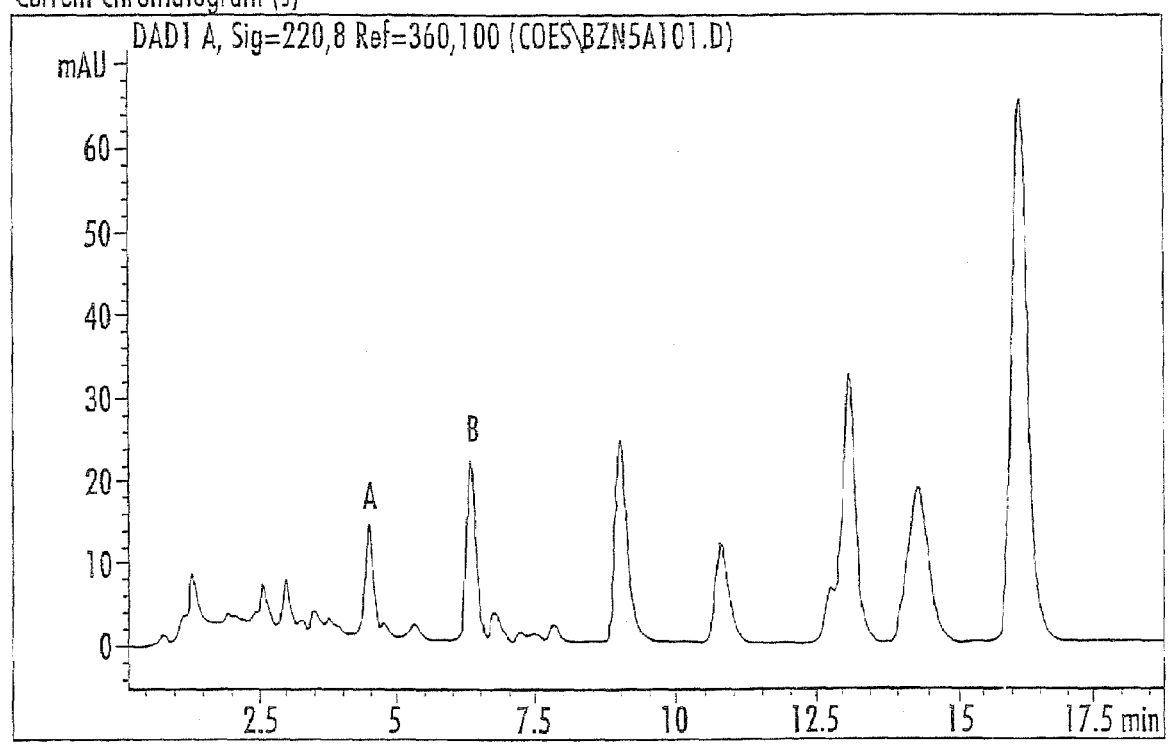
FIG. 1 is a HPLC Chromatogram using chromatographic method 1 showing Peaks A and B in the Endeavor 10-Component Conjugated Estrogens drug product.

The invention will now be described with reference to the embodiments set forth herein. These embodiments are intended to illustrate the invention and are not meant to limit the scope of the invention, which is defined by the claims.

In one aspect of the present invention, a compound represented by Formula I is provided.

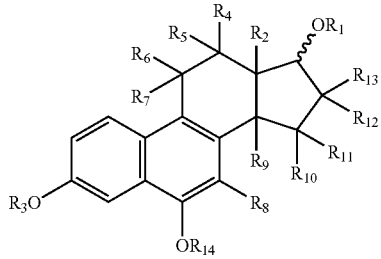

I wherein the bond represented by the wavy line may be a single or double bond such that when the wavy line is a single bond, $R_1$ may be selected from the group consisting of hydrogen, sulfate and glucoronide or other esters, and when the wavy line is a double bond, $R_1$ does not exist; $R_2$ is lower alkyl; $R_3$ may be selected from the group consisting of hydrogen, sulfate and glucoronide or other esters; and $R_4$ through $R_{13}$ may independently be selected from the group consisting of hydrogen, hydroxy, ketone, lower alkyl ($C_1$ to $C_4$), lower alkoxy ($C_1$ to $C_4$), halogen, and carbonyl groups. When $R_1$ is hydroxy, the hydroxy or ester substituent may have either an α or a β orientation, with the β orientation being preferred. $R_2$ is preferably $C_1$ to $C_4$ alkyl, and more preferably is methyl. $R_4$ through $R_{12}$ are preferably hydrogen. $R_{13}$ is preferably hydrogen or ethynyl. $R_{14}$ may be selected from the group consisting of hydrogen, sulfate and glucoronide and other esters The compound represented by Formula I is present in chemically pure form, (i.e., greater than about 90% pure). The compound represented by Formula I is preferably greater than about 95% pure, and is most preferably greater than about 99% pure.

A preferred compound is illustrated in Formula II:

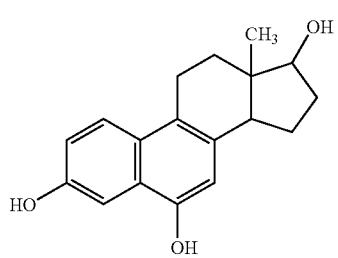

II

Another preferred compound is illustrated in Formula III:

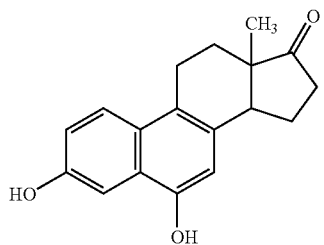

III

Compounds of the present invention may be present in a conjugated form. The conjugates may be various conjugates understood by those skilled in the art, including, but not limited to, glucuronide and sulfate. The most preferred conjugate is sulfate.

Compounds of the present invention may also be present as various pharmaceutically acceptable salts including salts of the conjugated compound. The salts may be various salts understood by those skilled in the art, including, but not limited to, sodium salts, calcium salts, magnesium salts, lithium salts, and amine salts such as piperazine salts. The most preferred salts are sodium salts.

In another aspect, the present invention provides a composition of matter. The composition of matter comprises one or more compounds according to the present invention.

In one embodiment, the composition of the invention includes at least one additional pharmaceutically active ingredient. Examples of additional active ingredients include, but are not limited to, other estrogenic compounds, androgenic compounds, progestin compounds, vasodilation agents, calcium salts, and vitamin D and its derivatives (e.g., calcitriol and mixtures and blends thereof) and mixtures and blends of the various compounds.

Examples of estrogenic compounds and compositions are set forth in U.S. patent application Ser. No. 09/524,132 filed on Mar. 10, 2000, which is commonly assigned to the assignee of the present invention, the disclosure of which is incorporated by reference herein in its entirety. Suitable estrogenic compounds include estrone, 17α-estradiol, 17β-estradiol, equilin, 17α-dihydroequilin, 17β-dihydroequilin, equilenin, 17α-dihydroequilenin, 17β-dihydroequilenin, $\Delta^{8,9}$-dehydroestrone, 17α-$\Delta^{8,9}$-dehydroestradiol, 17β-$\Delta^{8,9}$-dehydroestradiol, ethinyl estradiol, estradiol valerate, 6-OH equilenin, 6-OH 17α-dihydroequilenin, 6-OH 17β-dihydroequilenin, and mixtures, conjugates and salts thereof, and the estrogen ketones and their corresponding 17α- and 17β-hydroxy derivatives. The estrogenic compounds way also be present as conjugated estrogens. The conjugates may be various conjugates understood by those skilled in the art, including, but not limited to, sulfate and glucuronide. The most preferred estrogen conjugates are estrogen sulfates. The estrogenic compounds may also be present estrogen conjugates. In one embodiment, the estrogenic compounds are present as salts of estrogen conjugates. The salts may be various salts understood by those skilled in the art, including, but not limited to, sodium salts, calcium salts, magnesium salts, lithium salts, and piperazine salts. The most preferred salts are sodium salts. The estrogenic compounds can be derived from natural and synthetic sources.

Suitable androgenic compounds include methyltestosterone, androsterone, androsterone acetate, androsterone propionate, androsterone benzoate, androsteronediol, androsteronediol-3-acetate, androsteronediol-17-acetate, androsteronediol-3-17-diacetate, androsteronediol-17-benzoate, androsteronediol-3-acetate-17-benzoate, androsteronedione, dehydroepiandrosterone, sodium dehydroepiandrosterone sulfate, dromostanolone, dromostanolone propionate, ethylestrenol, fluoxymesterone, methyl testosterone, nandrolone phenpropionate, nandrolone decanoate, nandrolone furylpropionate, nandrolone cyclohexane-propionate, nandrolone benzoate, nandrolone cyclohexanecarboxylate, oxandrolone, oxymetholone, stanozolol, testosterone, testosterone decanoate, 4-dihydrotestosterone, 5α-dihydrotestosterone, testolactone, 17α-methyl-19-nortestosterone and pharmaceutically acceptable esters and salts thereof, and combinations of any of the foregoing.

Suitable vasodilation compounds include alpha andrenergic antagonists. Exemplary α-adrenergic compounds include phentolamine, phenoxybenzalamine, tolazoline, doxazosin, dibenamine, prazosin, prazosin hydrochloride, phenoxybenzamine and the like. Preferably, phentolamine is used and can form pharmaceutically acceptable salts with organic and inorganic acids, as described, for example, in U.S. Pat. No. 6,001,845 to Estok, the disclosure of which is incorporated herein by reference in its entirety. Preferably phentolamine mesylate or phentolamine hydrochloride is used. Other vasodilation compounds include phosphodiesterase type 5 inhibitors (e.g., suldenafi), prostaglandin E compounds (e.g., alprostodil), thymoxamine, bromocriptine, yohimbine, paperverine, apomorphine, organic nitrates, imipramine, verapamil, naftidrofuryl, and isoxsuprine. Combinations of the various vasodilation compounds may be used.

Examples of progestins are set forth in U.S. Pat. No. Re. 36,247 to Plunkett et al., the disclosure of which is incorporated herein by reference in its entirety. Suitable progestin compounds include desogestrel, dydrogesterone, ethynodiol diacetate, medroxyprogesterone, levonorgestrel, medroxyprogesterone acetate, hydroxyprogesterone caproate, norethindrone, norethindrone acetate, norethynodrel, allylestrenol, 19-nortestosterone, lynoestrenol, quingestanol acetate, medrogestone, norgestrienone, dimethisterone, ethisterone, cyproterone acetate, chlornadinone acetate, megestrol acetate, norgestimate, norgestrel, desogestrel, trimegestone, gestodene, nomegestrol acetate, progesterone, 5α-pregnan-3β,20α-diol sulfate, 5α-pregnan-3β,20β-diol sulfate, 5α-pregnan-3β-ol-20-one, 16, 5α-pregnen-3β-ol-20-one, 4-pregnen-20β-ol-3-one-20-sulfate and mixtures thereof.

Calcium salts may include, without limitation, organic acid salts of calcium such as calcium citrate, calcium lactate, calcium fumurate, calcium acetate, and calcium glycerophosphate, as well as inorganic salts such as calcium chloride, calcium phosphate, calcium sulphate, and calcium nitrate.

Pharmaceutically acceptable salts, solvates, hydrates, and polymorphs may be formed of any of the active ingredients employed in the composition of the invention. The invention also encompasses embodiments in which the composition of matter defined herein is included in various quantities in combination with known pharmaceutically accepted formulations. For example, the composition of matter of the invention may be incorporated into various known estrogen-containing drug products such as, Premarin® made commercially available by Wyeth-Ayerst Laboratories of Philadelphia, Pa. The composition of matter of the invention may also be employed as part of a continuous estrogen-progestin therapy regimen such as that described by U.S. Pat. No. Re. 36,247 to Plunkett et al. and made commercially available as Prempro® and Premphase® by Wyeth-Ayerst Laboratories.

The present invention also encompasses pharmaceutically acceptable drug products comprising a composition of matter of the present invention and at least one pharmaceutically acceptable carrier, diluent, or excipient, the selection of which are known to the skilled artisan. The drug product formulations can be in various forms such as, for example, tablets; effervescent tablets; pills; powders; elixirs; suspensions; emulsions; solutions; syrups; soft and hard gelatin capsules; transdermal patches; topical gels, creams and the like; suppositories; sterile injectable solutions; and sterile packaged powders, sublingual tablets, buccal tablets, and buccal adhesive systems.

In certain embodiments, the drug product is present in a solid pharmaceutical composition that may be suitable for oral administration. A solid composition of matter according to the present invention may be formed and may be mixed with an excipient, diluted by an excipient or enclosed within such a carrier which can be in the form of a capsule, sachet, tablet, paper, or other container. When the excipient serves as a diluent, it may be a solid, semi-solid, or liquid material which acts as a vehicle, carrier, or medium for the composition of matter.

Various suitable excipients will be understood by those skilled in the art and may be found in the *National Formulary* 19, pages 2404-2406 (2000), the disclosure of pages 2404 to 2406 being incorporated herein in their entirety. For example, the drug product formulations may include lubricating agents such as, for example, talc, magnesium stearate and mineral oil; wetting agents; emulsifying and suspending agents; binding agents such as starches, gum arabic, microcrystalline cellulose, cellulose, methylcellulose, and syrup; anticaking agents such as calcium silicate; coating agents such as methacrylates and shellac; preserving agents such as methyl- and propyl hydroxybenzoates; sweetening agents; or flavoring agents. Polyols, buffers, and inert fillers may also be used. Examples of polyols include, but are not limited to, mannitol, sorbitol, xylitol, sucrose, maltose, glucose, lactose, dextrose, and the like. Suitable buffers encompass, but are not limited to, phosphate, citrate, tartarate, succinate, and the like. Other inert fillers which may be used encompass those which are known in the art and are useful in the manufacture of various dosage forms. If desired, the solid formulations may include other components such as bulking agents and/or granulating agents, and the like. The drug products of the invention may be formulated so as to provide quick, sustained, or delayed release of the active ingredient after administration to the patient by employing procedures well known in the art.

To form tablets for oral administration, the composition of matter of the present invention may be made by a direct compression process. In this process, the active drug ingredients may be mixed with a solid, pulverant carrier such as, for example, lactose, saccharose, sorbitol, mannitol, starch, amylopectin, cellulose derivatives or gelatin, and mixtures thereof, as well as with an antifriction agent such as, for example, magnesium stearate, calcium stearate, and polyethylene glycol waxes. The mixture may then be pressed into tablets using a machine with the appropriate punches and dies to obtain the desired tablet size. The operating parameters of the machine may be selected by the skilled artisan. Alternatively, tablets for oral administration may be formed by a wet granulation process. Active drug ingredients may be mixed with excipients and/or diluents. The solid substances may be ground or sieved to a desired particle size. A binding agent may be added to the drug. The binding agent may be suspended and homogenized in a suitable solvent. The active ingredient and auxiliary agents may also be mixed with the binding agent solution. The resulting dry mixture is moistened with the solution uniformly. The moistening typically causes the particles to aggregate slightly, and the resulting mass is pressed through a stainless steel sieve having a desired size. The mixture is then dried in controlled drying units for the determined length of time necessary to achieve a desired particle size and consistency. The granules of the dried mixture are sieved to remove any powder. To this mixture, disintegrating, antifriction, and/or anti-adhesive agents are added. Finally, the mixture is pressed into tablets using a machine with the appropriate punches and dies to obtain the desired tablet size. The operating parameters of the machine may be selected by the skilled artisan.

If coated tablets are desired, the above-prepared cores may be coated with a concentrated solution of sugar or cellulosic polymers, which may contain gum arabic, gelatin, talc, titanium dioxide, or with a lacquer dissolved in a volatile organic solvent, aqueous solvent, or a mixture of solvents. To this coating, various dyes may be added in order to distinguish among tablets with different active compounds or with different amounts of the active compound present. In a particular embodiment, the active ingredient may be present in a core surrounded by one or more layers including enteric coating layers.

Soft gelatin capsules may be prepared in which capsules contain a mixture of the active ingredient and vegetable oil. Hard gelatin capsules may contain granules of the active ingredient in combination with a solid, pulverulent carrier, such as, for example, lactose, saccharose, sorbitol, mannitol, potato starch, corn starch, amylopectin, cellulose derivatives, and/or gelatin.

In one preferred embodiment, the formulation is in the form of orally-administered tablets which contain the composition of matter of the present invention as set forth herein along with the following inactive ingredients: calcium phosphate tribasic, calcium sulfate, carnauba wax, cellulose, glyceryl monooleate, lactose, magnesium stearate, methylcellulose, pharmaceutical glaze, polyethylene glycol, stearic acid, sucrose, and titanium dioxide. Such ingredients may be present in amounts similar to those present in Premarin® (conjugated estrogens tablets, USP) made commercially available by Wyeth-Ayerst Laboratories of Philadelphia, Pa. Tablets employing the active ingredients of the invention may contain excipients similar to those contained in the 0.3 mg., 0.625 mg., and 1.25 mg tablets of Premarin® (conjugated estrogens tablets, USP).

Liquid preparations for oral administration may be prepared in the form of syrups or suspensions, e.g., solutions containing an active ingredient, sugar, and a mixture of ethanol, water, glycerol, and propylene glycol. If desired, such liquid preparations may contain coloring agents, flavoring agents, and saccharin. Thickening agents such as carboxymethylcellulose may also be used.

In the event that the above formulations are to be used for parenteral administration, such a formulation may comprise sterile aqueous injection solutions, non-aqueous injection solutions, or both comprising the composition of matter of the present invention. When aqueous injection solutions are prepared, the composition of matter may be present as a water-soluble pharmaceutically acceptable salt. Parenteral preparations may contain anti-oxidants, buffers, bacteriostats, and solutes which render the formulation isotonic with the blood of the intended recipient. Aqueous and non-aqueous sterile suspensions may include suspending agents and thickening agents. The formulations may be presented in unit-dose or multi-dose containers, for example sealed ampules and vials. Extemporaneous injection solutions and suspensions may be prepared from sterile powders, granules and tablets of the kind previously described.

In a preferred embodiment, the drug product of the present invention is in the form of an injectable solution containing a predetermined amount (e.g., 25 mg) of the composition of matter in a sterile lyphilized cake which also contains lactose, sodium citrate, and simethicone. The pH of a solution containing the above ingredients may be adjusted using a suitable buffer (e.g., sodium hydroxide or hydrochloric acid). Reconstitution may be carried out according to known methods, e.g., using a sterile diluent (5 mL) containing 2 percent benzyl alcohol in sterile water. A preferred injectable solution is similar to Premarin® Intravenous made commercially available by Wyeth-Ayerst Laboratories.

The composition of matter also may be formulated such that it is suitable for topical administration (e.g., vaginal cream). These formulations may contain various excipients known to those skilled in the art. Suitable excipients may include, but are not limited to, cetyl esters wax, cetyl alcohol, white wax, glyceryl monostearate, propylene glycol monostearate, methyl stearate, benzyl alcohol, sodium lauryl sulfate, glycerin, mineral oil, water, carbomer, ethyl alcohol, acrylate adhesives, polyisobutylene adhesives, and silicone adhesives.

In a preferred embodiment, the drug product is in the form of a vaginal cream containing the composition of matter as set forth herein present in a nonliquefying base. The nonliquefying base may contain various inactive ingredients such as, for example, cetyl esters wax, cetyl alcohol, white wax, glyceryl monostearate, propylene glycol monostearate, methyl stearate, benzyl alcohol, sodium lauryl sulfate, glycerin, and mineral oil. Such composition may be formulated similar to Premarin® Vaginal Cream made commercially available by Wyeth-Ayerst Laboratories.

Dosage units for rectal administration may be prepared in the form of suppositories which may contain the composition of matter in a mixture with a neutral fat base, or they may be prepared in the form of gelatin-rectal capsules which contain the active substance in a mixture with a vegetable oil or paraffin oil.

In another aspect, the present invention relates to methods of treating mammals (e.g., man) in need of treatment. The methods include administering an effective amount of a composition of matter as defined herein to the mammal in need of treatment. The methods may be used for a number of treatments such as, but not limited to, vasomotor symptoms; atrophic vaginitis; osteoporosis; hypoestrogenism due to hypogonadism, castration, or primary ovarian failure; breast cancer in selected persons with metastatic disease; advanced androgen-dependent carcinoma of the prostate; abnormal uterine bleeding; and kraurosis vulvae. The administration may be cyclic, occurring for one or more short periods of time or courses of treatment (i.e. short-term use). Alternatively, the administration may be continuous, occurring over extended periods of time (i.e. long-term use). One example of long-term use would be from the onset of menopause until death. Cyclic and continuous administration may be either uninterrupted or interrupted. Uninterrupted administration occurs one or more times daily such that there is no break in treatment. Interrupted administration occurs other than daily, for example a repeated course of treatment including three weeks of daily treatment followed by one week of no treatment.

EXAMPLES

The present invention will now be described in greater detail with respect to the following numbered examples. In the examples, "mL" means milliliter, "° C." means degrees Celcius, "mM" means millimoles/liter, "M" means moles/liter, "Å" means angstrom, "µm" means micrometer, "nm" means nanometer, "mm" means millimeter, "mg" means milligram, and "m/z" means mass to charge ratio. These examples are for illustrating the invention and are not intended to limit the invention as set forth by the claims.

A list of instruments and equipment employed in the examples are as follows:
1. HPLC Chromatographic Procedures
   a. Analytical scale chromatographic system
      1. HP1100 Diode-array detector
      2. HP1100 Quaternary HPLC pump
      3. Shimadzu, Model RF-551, fluorescence detector
      4. HP1100 Thermostatically controlled column compartment
   b. Semi-prep scale chromatographic system
      1. HP1100 HPLC chromatographic system
      2. HP1100 Diode-array detector
      3. HP1100 Quaternary HPLC pump
      4. HP1100 Thermostatically controlled column compartment
   c. Prep scale chromatographic system
      1. Waters Delta Prep 4000 chromatographic system
      2. Waters 2487 UV detector
      3. Waters fraction collector II
      4. Waters PrepLC 40 mm radial compression assembly
      5. Waters Nova-Pak HR $C_{18}$ gun radial compression column segments, (2) 40 mm×100 mm segments with a 40 mm×10 mm guard segment
2. Fraction Collection, Purification, and Crystallization
   a. ISCO Foxy Jr., Fraction Collector
   b. Büchi, Model R-124 rotary evaporator
   c. Sep-Pak, SPE cartridges, Varian Bond Elut $C_{18}$
   d. Waters fraction collector II
3. Mass Spectral Analyses
   a. Fast Atom Bombardment (FAB-MS)
      1. Instrument: VG Analytical ZAB 2-SE
      2. Sample input: Cesium ion gun
      3. Data system: VG Analytical 11-250J with PDP 11/73
      4. Solvent: Methanol
      5. Matrix: Glycerol/Thioglycerol/Triethylamine
   b. High Resolution Mass Spectrometer (HR-MS)
      1. Instrument: VG Analytical ZAB 2-SE
      2. Sample input: Cesium ion gun
      3. Data System: VG Analytical 11-250J with PDP 11/73
      4. Solvent: Methanol
      5. Matrix: Peak A: PEG 300 & PEG 400
         Peak B: PEG 300 & m-nitrobenzyl alcohol
B. Chemicals, Reagents, and Analytical Materials
   1. Chemicals and Reagents
      a. Acetonitrile (ACN), HPLC grade
      b. Methanol (MeOH), HPLC grade
      c. Milli-Q water
      d. Triethylamine (TEA), HPLC grade
      e. tert-Butyl ammonium hydroxide (TBAH), 0.4 M, reagent grade
      f. Potassium phosphate monobasic, AR grade
      g. Nitrogen gas, zero grade
      h. Phosphoric acid, 85%
      i. Hydrochloric acid, concentrated
      j. Sodium hydroxide
   2. Analytical Samples
      Conjugated estrogens tablets, 1.25 mg, FDL lot #00426-064
   3. Analytical Standards
      a. Conjugated Estrogens Reference Standard (ten component), Organics/LaGrange, Inc. (OLG) lot #C02322
      b. Equilin sulfate, sodium salt, OLG lot#RD1810
      c. Equilin sulfate, sodium salt, Diosynth lot#00004429
      d. 17α-Dihydroequilin sulfate, sodium salt, OLG lot#RD1812
      e. 17α-Dihydroequilin sulfate, sodium salt, Diosynth lot#58
      f. $\Delta^{8,9}$-Dehydroestrone, Proquina lot#9371-1/95
      g. $\Delta^{8,9}$-Dehydroestrone, lot#HS 30/95, supplier unknown
      h. $\Delta^{8,9}$-Dehydroestrone, sulfate+estrone sulfate, sodium salts, lot#17-44, supplier unknown Examples 1-4

Isolation of Compounds A and B

The compounds of Peaks A and B are isolated from a 10-component conjugated estrogen available from Endeavor Pharmaceuticals of Wilmington, N.C. as follows:

Example 1

HPLC Chromatographic Assay Method 1 (Analytical Scale)

A standard solution containing about 0.03 mg/mL of Conjugated Estrogens Drug Substance may be prepared. The drug substance may be provided in powder form or a powder may be formed by grinding tablets. An appropriate amount of drug substance is weighed to yield 200 mL of solution. The drug substance is placed in a 200 ml volumetric flask. A 61 mL volume of organic diluent is added to the flask and the flask is mechanically shaken for 15 minutes. About 100 mL of aqueous diluent is then added to the flask and the flask is once again mechanically shaken for 15 minutes. The resulting solution is diluted to volume with aqueous diluent and mixed well. A portion of the solution is filtered through a 0.45 µm PTFE filter.

A 50 mM phosphate buffer solution may be prepared using potassium phosphate.

An aqueous diluent solution containing phosphate buffer and 0.4 M TBAH with a volumetric ratio of 277:0.9 may be prepared. The pH can be adjusted to 3.0±0.1 using phosphoric acid.

An organic diluent solution containing acetonitrile and methanol with a volumetric ratio of 26.5:4 may be prepared.

A mobile phase may be prepared by mixing organic diluent and aqueous diluent to form a solution with a volumetric ratio of 30.5:69.5, organic:aqueous.

When 1.25 mg tablets are to be analyzed, five washed and ground tablets are placed into a 200 mL volumetric flask. A 61 mL volume of organic diluent is added to the flask and the flask is mechanically shaken for 15 minutes. About 100 mL of aqueous diluent is then added to the flask and the flask is once again mechanically shaken for 15 minutes. The resulting solution is diluted to volume with aqueous diluent and mixed. A portion of the solution is filtered through a 0.45 μm PTFE filter.

In this chromatographic analysis, an HPLC system with a column heater equipped with a 3 μm, 15.0 cm×4.6 mm $C_{18}$ column and suitable UV detector for detection at 220 nm and diode array was employed. The flow rate was set for 1.5 mL/minute and the column temperature was set for 25° C.

An example of a chromatographic procedure is as follows: Equal volumes of the standard solution and the sample preparations were separately injected into the chromatographic systems. Peaks A and B were integrated and evaluated based on the peak area response for the chromatogram (area percent).

Example 2

HPLC Chromatographic Separation Method 2 (Semi-Prep Scale)

A Mobile Phase A (aqueous) containing 15 mM TEA in 0.125% concentrated HCl may be prepared by combining 42 mL of TEA with 20 L of water and mixing well. To the resulting solution, 25 mL of concentrated HCl is added and the pH is adjusted to approximately 7.0 with 1 N HCl or 1 N NaOH.

A Mobile Phase B (organic) containing 15 mM TEA in 0.125% concentrated HCl in acetonitrile may be prepared by combining 16.8 mL of TEA with 8 L of acetonitrile and adding 10 mL of concentrated HCl. The resulting solution is then mixed well.

A sample for Peak A collection containing a 30 mg/mL solution of 17α-dihydroequilin sulfate, sodium salt in mobile phase A may be prepared.

In this chromatographic separation for Peak A collection, a semi-prep scale HPLC system equipped with an appropriate fraction collector, a Waters Symmetry $C_{18}$ (7.8 mm×300.0 mm), 7 μm column, and a suitable UV detector for detection at 220 nm may be employed. The flow rate may be set for 5 mL/minute, the column temperature may be set to 40° C., and the gradient elution profile may be as follows:

| Time | % Mobile Phase | |
|---|---|---|
| (Minutes) | A | B |
| 0.0 | 83 | 17 |
| 42.0 | 83 | 17 |
| 42.1 | 50 | 50 |
| 47.0 | 50 | 50 |
| 47.1 | 83 | 17 |

An example of a chromatographic procedure is as follows: 150 μL portions of the sample solution were separately injected into the chromatograph until all of the sample solution had been injected. The fraction containing the peak at approximately 41 minutes was collected and labeled as Peak A.

Example 3

HPLC Chromatographic Separation Method 3 (Prep Scale)

A Mobile Phase A (aqueous) containing 60 mM TEA in 0.5% concentrated HCl may be prepared by combining 168 mL of TEA with 20 L of water and mixing well. To the resulting solution, 100 mL of concentrated HCl is added and the pH is adjusted to approximately 3.0 with 1 N HCl or 1 N NaOH.

A Mobile Phase B (organic) containing 60 mM TEA in 0.5% concentrated HCl in acetonitrile may be prepared by combining 84 mL of TEA with 10 L of acetonitrile and adding 50 mL of concentrated HCl. The resulting solution is then mixed well.

A sample solution for Peak A collection containing a 20 mg/mL solution of 17α-dihydroequilin sulfate, sodium salt in mobile phase A may be prepared.

A sample solution for Peak B collection containing a 20 mg/mL solution of equilin sulfate, sodium salt in mobile phase A may be prepared.

In this chromatographic separation for Peak A collection, a prep scale HPLC system equipped with an appropriate fraction collector, two 40 mm×100.0 mm radial compression $C_{18}$ column segments, a 40 mm×10 mm guard segment and a suitable UV detector for detection at 220 nm with the full scale absorbance set at 4.0 may be employed. The flow rate may be set for 50 mL/minute, the temperature is preferably ambient temperature, and the gradient elution profile may be as follows:

| Time | % Mobile Phase | |
|---|---|---|
| (Minutes) | A | B |
| 0.0 | 83 | 17 |
| 43.0 | 83 | 17 |
| 43.1 | 40 | 60 |
| 52.0 | 40 | 60 |
| 52.1 | 83 | 17 |

In this chromatographic separation for Peak B collection, a prep scale HPLC system equipped with an appropriate fraction collector, two 40 mm×100.0 mm radial compression C18 column segments, a 40 mm×10 mm guard segment and a suitable UV detector for detection at 220 nm with the full scale absorbance set at 4.0 may be employed. The flow rate may be set for 50 mL/minute, the temperature is preferably ambient temperature, and the gradient elution profile may be as follows:

| Time | % Mobile Phase | |
|---|---|---|
| (Minutes) | A | B |
| 0.0 | 80 | 20 |
| 35.0 | 80 | 20 |
| 35.1 | 40 | 60 |
| 41.0 | 40 | 60 |
| 41.1 | 80 | 20 |

An example of a chromatographic procedure for Peak A collection is as follows: 10 mL portions of the sample solution for Peak A were separately injected into the chromatograph until all of the sample solution had been injected. The fraction containing the peak at approximately 39 minutes was collected and labeled as Peak A.

An example of a chromatographic procedure for Peak B collection is as follows: 10 mL portions of the sample solution for Peak B were separately injected into the chromatograph until all of the sample solution had been injected. The fraction containing the peak at approximately 29 minutes was collected and labeled as Peak B.

Example 4

HPLC Chromatographic Assay Method 4 (Analytical Scale)

A Mobile Phase A (aqueous) containing 15 mM TEA in 0.125% concentrated HCl may be prepared by combining 4.2 mL of TEA with 2 L of water and mixing well. To the resulting solution, 2.5 mL of concentrated HCl is added and the pH is adjusted to approximately 3.0 with 1 N HCl or 1 N NaOH.

A Mobile Phase B (organic) containing 15 mM TEA in 0.125% concentrated HCl in acetonitrile may be prepared by combining 4.2 mL of TEA with 2 L of acetonitrile and adding 2.5 mL of concentrated HCl. The resulting solution is then mixed well.

A mobile phase may be prepared using a gradient system or by manually preparing a mixture of 80% (v/v) Mobile Phase A and 20% (v/v) Mobile Phase B.

A sample solution containing approximately 0.06 mg/mL conjugated estrogens in mobile phase may be prepared by transferring one 1.25 mg tablet into a 25 mL volumetric flask. A 6 mL volume of Mobile Phase B is added to the flask and the flask is mechanically shaken for 10 minutes. The resulting solution is diluted to volume with Mobile Phase A and then mixed well. A portion of the solution is filtered through a 0.45 μm PTFE filter.

In this chromatographic analysis, an HP1100 HPLC system with a column heater equipped with a 3 μm, 15.0 cm×4.6 mm $C_{18}$ column and suitable UV detector for detection at 220 nm and diode array was employed. The flow rate may be set for 1.5 mL/minute and the column temperature may be set for 25° C.

An example of a chromatographic procedure is as follows: Equal volumes of the standard solution and the sample preparations were separately injected into the chromatographic systems. Peaks A and B were integrated and evaluated based on the peak area response for the chromatogram (area percent).

Examples 5 and 6

Characterization of Peaks A and B

Figure 2:
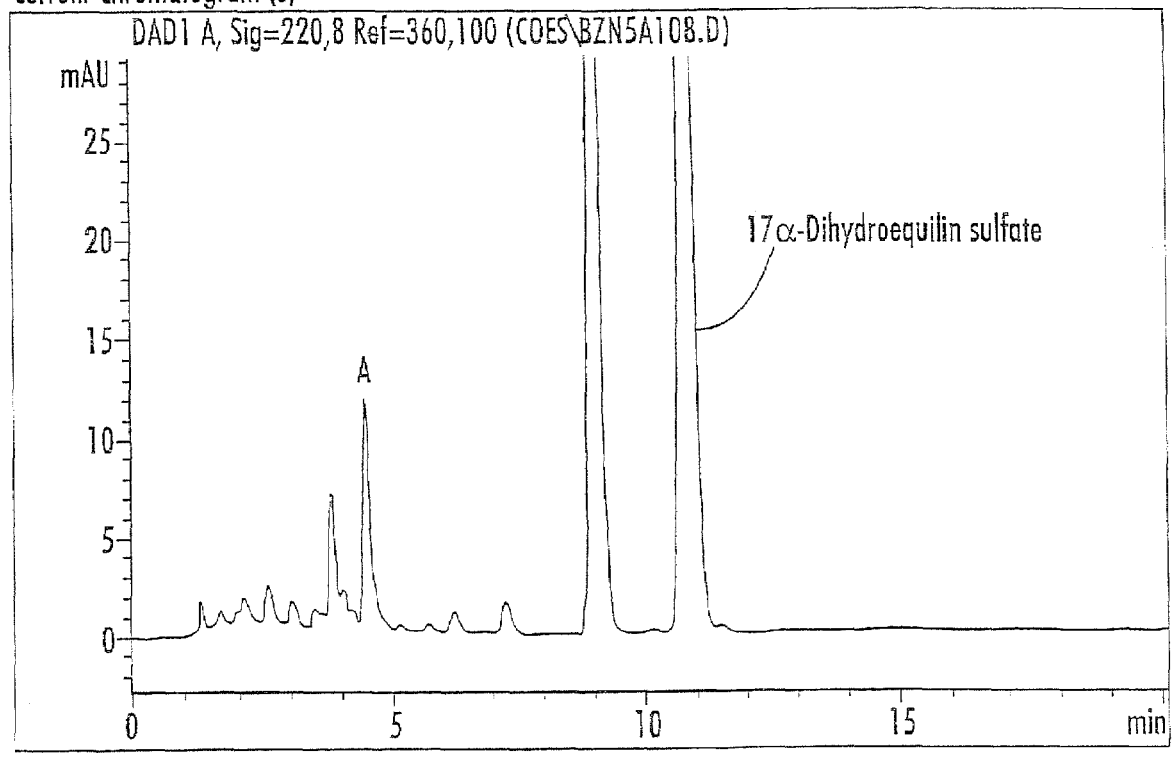
FIG. 2 is a HPLC Chromatogram using chromatographic method 1 showing Peak A in the 17α-dihydroequilin sulfate, sodium salt standard.
Figure 3:
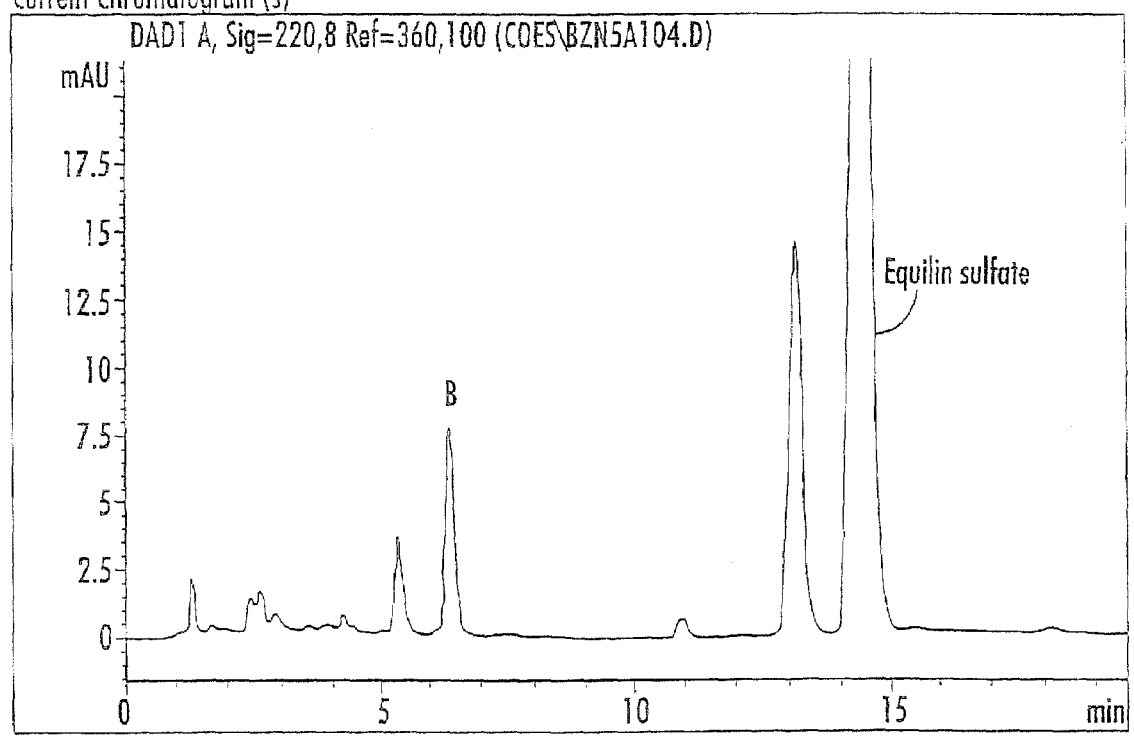
FIG. 3 is a HPLC Chromatogram using chromatographic method 1 showing Peak B in the Equilin sulfate, sodium salt standard.

Examples 5 and 6 detail the characterization of Peaks A and B found in the Endeavor Pharmaceuticals 10-Component Conjugated Estrogens drug product (FIG. 1). These compounds were also found to be present in certain estrogen standards which were evaluated. Peak A was found to be present in the 17α-dihydroequilin sulfate, sodium salt standard (FIG. 2) and Peak B was found to be present in the equilin sulfate, sodium salt standards (FIG. 3). Due to the simplicity of the standard materials, the individual peaks were collected by chromatographic fraction collection from the corresponding standard and upon purification, were isolated as yellowish amorphous materials.

The fractioned samples were analyzed using techniques such as mass spectrometry (MS), and one-dimensional (1D) and two-dimensional (2D) nuclear magnetic resonance (NMR) spectrometry. Mass spectrometry utilized both low and high resolution fast atom bombardment mass spectrometry (FAB-MS) to determine the accurate molecular weight and empirical formula of the compounds. For the NMR analyses, samples were dissolved in deuterated dimethyl sulfoxide ($d_6$-DMSO), which permitted the hydroxylprotons to be visible during analysis. NMR techniques included $^1$H-NMR (proton), $^{13}$C-NMR (carbon), homonuclear correlation spectroscopy (COSY), distortionless enhancement by polarization transfer (DEPT), heteronuclear multiple quantum coherence (HMQC), and heteronuclear multiple bond correlation (HMBC). 2D COSY analyses helped determine the correlation of neighboring protons to one another, while DEPT analyses determined the assignment of carbon type. 2D HMQC analyses provided information about what protons are attached to what carbons, and 2D HMBC analyses showed longer range coupling of the proton and carbon atoms (usually 2 to 4 bonds away).

Example 5

Peak A Characterization

Separation and Isolation

Figure 4:
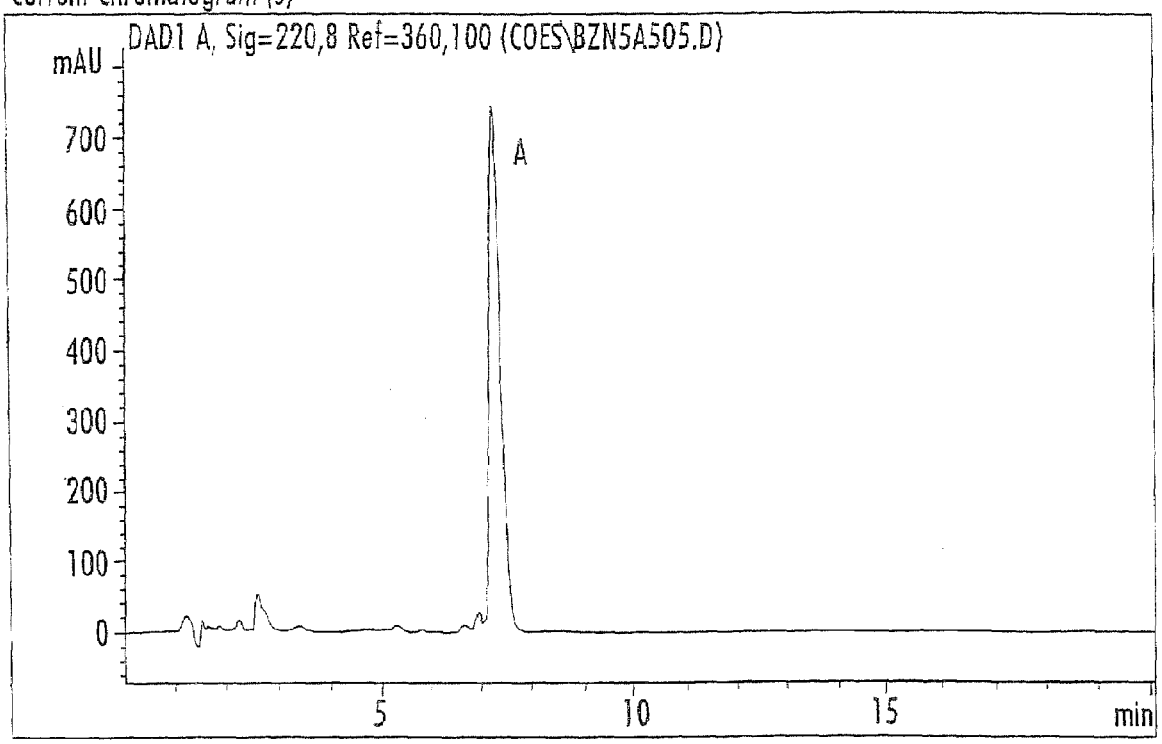
FIG. 4 is a HPLC Chromatogram using chromatographic method 4 showing re-injection of Peak A to determine its approximate purity.

Peak A was isolated as a triethyl ammonium salt due to the ion-pairing agent of the mobile phase of the HPLC chromatographic method described above in Example 2. After the fraction was collected, most of the ACN was removed by rotary evaporation, and the fraction was further concentrated using a $C_{18}$ SPE cartridge, washed with water, and eluted with approximately 10 mL of methanol. The fraction was then brought to dryness under a stream of dry nitrogen. Using the HPLC method described in above Example 4, a small portion of the 5.3 mg of Peak A isolated for testing by MS and NMR was redissolved in mobile phase and injected into the HPLC system to determine the purity of the fraction. This injection of Peak A showed a purity of about 89% (FIG. 4).

Mass Spectral Analyses

Figure 5:
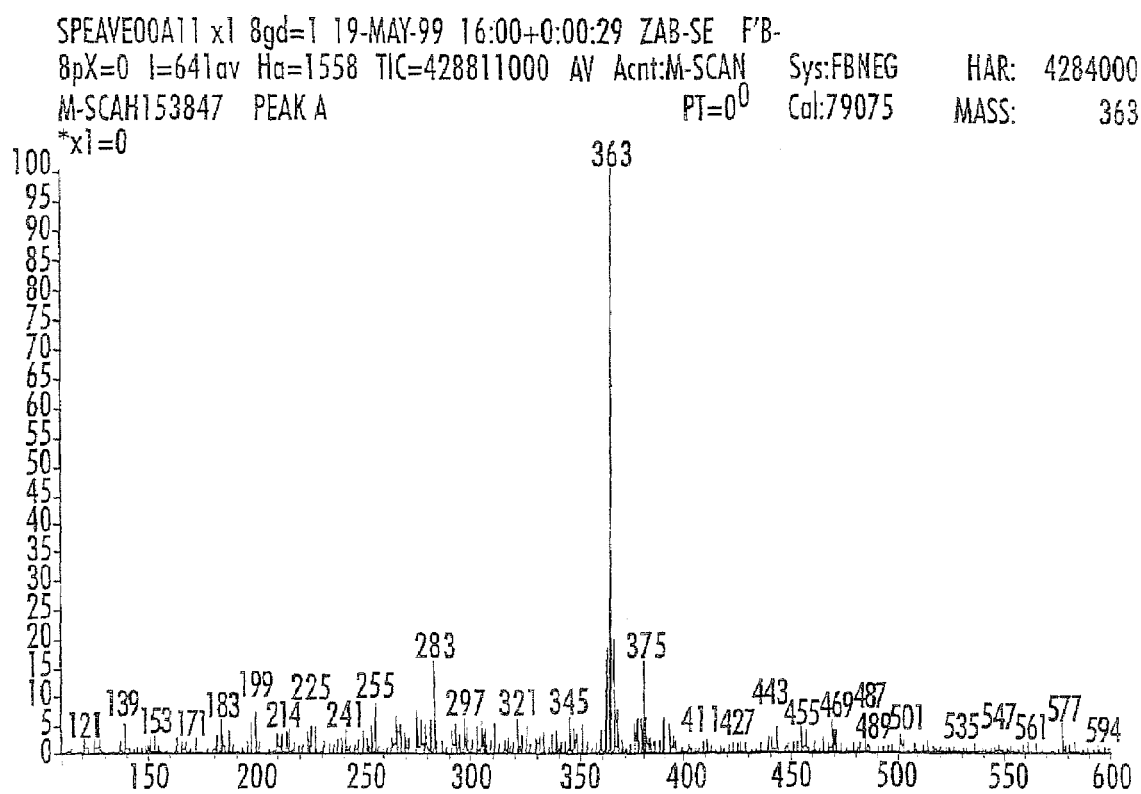
FIG. 5 is a low resolution negative ion FAB-MS spectrum of Peak A.
Figure 6:
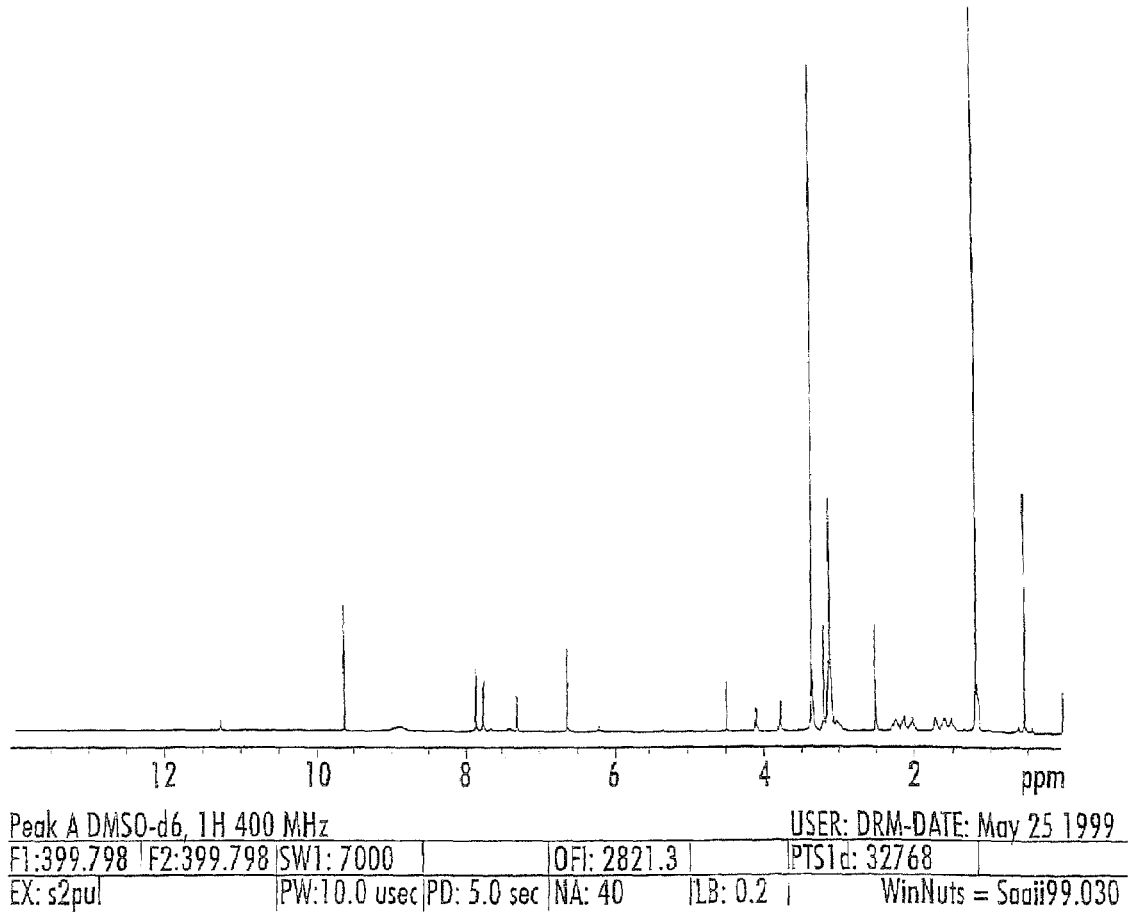
FIG. 6 is a full range 400 MHz $^1$H-NMR spectrum of Peak A in $d_6$-DMSO.
Figure 7:
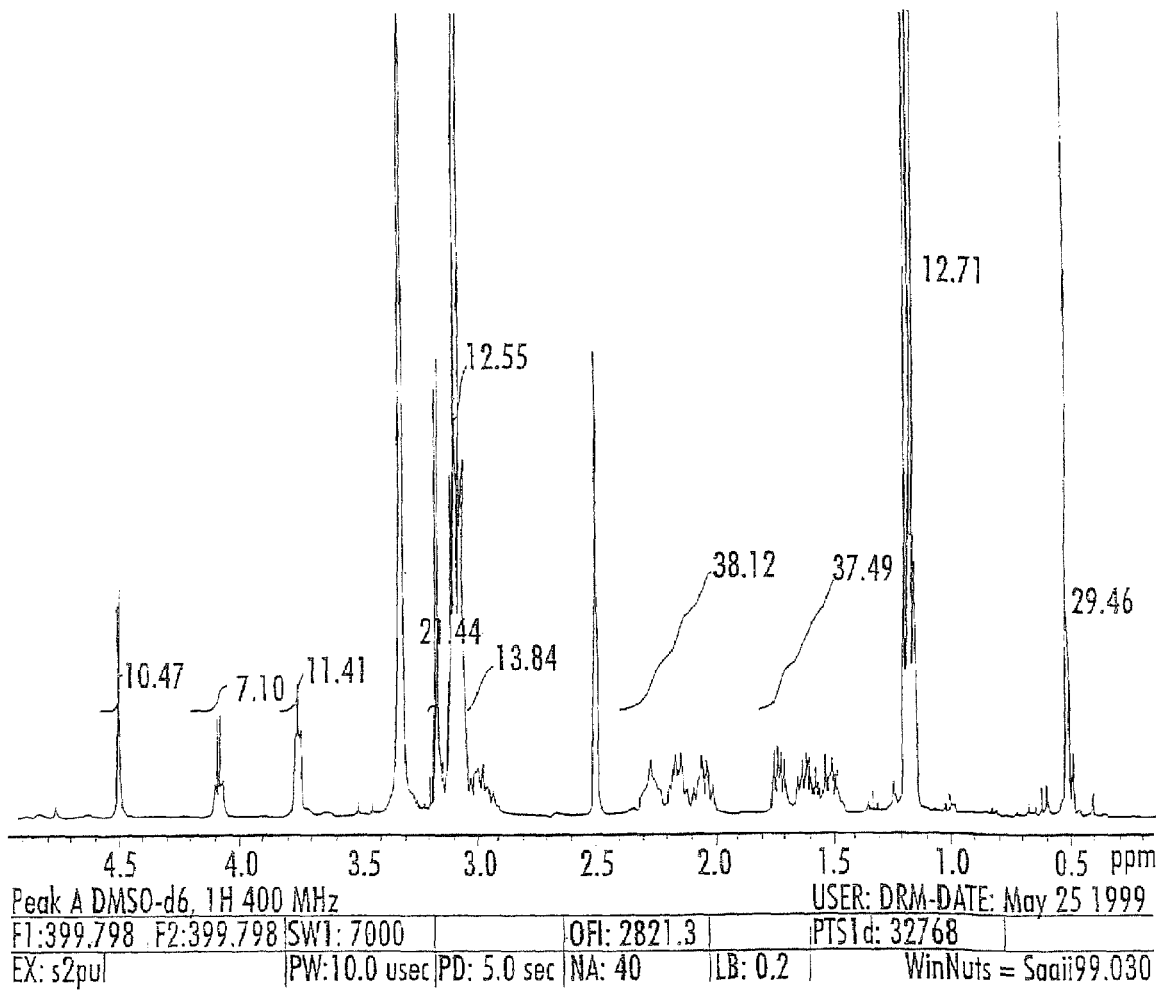
FIG. 7 is a 400 MHz $^1$H-NMR spectrum of the aliphatic region of Peak A in $d_6$-DMSO.

Preliminary negative ion FAB-MS spectral data of the isolated fraction of Peak A indicated that the molecular weight was approximately 363 m/z (FIG. 5). A negative ion HR-MS study indicated a mass of 363.0909 amu that compares well with the calculated mass of 363.0902 amu for the proposed molecular formula of $C_{18}H_{19}O_6S_1$ for Peak A.

Proton ($^1$H) and 2D COSY Nuclear Magnetic Resonance Spectroscopy

The $^1$H-NMR and the 2D COSY spectra of Peak A in deuterated dimethyl sulfoxide ($d_6$-DMSO) are shown in FIGS. 6-8 and 9-11, respectively. The peak assignments, based upon the proton NMR spectra and COSY spectral couplings, are shown in Table 1 and are consistent with the proposed structure of Peak A.

Carbon ($^{13}$C), 2D HMQC, and 2D HMBC Nuclear Magnetic Resonance

The $^{13}$C-NMR, HMQC, and HMBC spectra of Peak A in deuterated dimethyl sulfoxide ($d_6$-DMSO) are shown in FIGS. 12-15, 16-19, and 20-24, respectively. In order to collect the data more quickly and with a greater signal to noise ratio, the $^{13}$C-NMR spectrum was obtained non-quantitatively, and integrations were not performed. Peak assignments based upon the carbon NMR, HMQC, and HMBC spectral interpretations are shown in Table 2 and were consistent with the proposed structure of Peak A. 2D HMBC data can be more difficult to interpret, since it is possible that all crosspeaks are not observed. HMBC signals may typically occur with H—C connectivities that are 2 to 4 bonds removed, but also can detect some 1 to 2 bond connections.

TABLE 1

Summary Table of Proton NMR and COSY Band Assignments

| Chemical Shift Tentative (ppm) | Multiplicty* | Number Of Protons | COSY Couplings** | Assignment |
|---|---|---|---|---|
| 0.52 | s | 3 | 12b | 18 |
| 1.17 | t | 9 | 19 | 20 |
| 1.52 | m | 1 | 14, 15b, 16a, 16b | 15a |
| 1.60 | m | 1 | 15a, 15b, 16b | 6a |
| 1.73 | m | 1 | 11a, 11b, 12b | 12a |
| 2.04 | m | 1 | 11a, 11b, 12a, 18 | 12b |
| 2.16 | m | 1 | 14, 15a, 16a | 15b |
| 2.27 | m | 1 | 15a, 16a, 17 | 16b |
| 2.50 | — | — | — | solvent-DMSO |
| 2.99 | m | 1 | 12a, 12b, 11b | 11a |
| 3.09 | q | 6 | 20 | 19 |
| 3.10 | d | 1 | 15a, 15b | 14 |
| 3.13 | m | 1 | 12a, 12b | 11b |
| 3.17 | — | — | — | solvent-MeOH |
| 3.33 | — | — | — | solvent-H$_2$O |
| 3.76 | t | 1 | 16b, 17-OH | 17 |
| 4.09 | — | — | — | solvent-MeOH |
| 4.50 | d(w) | 1 | 17 | 17(OH) |
| 6.62 | s | 1 | — | 7 |
| 7.30 | d of d | 1 | 1, 4 | 2 |
| 7.75 | d | 1 | 2 | 1 |
| 7.85 | d(w) | 1 | 2 | 4 |
| 8.90 | bs | 1 | — | NH$^+$ |
| 9.64 | s | 1 | — | 6(OH) |

*s-singlet, d-doublet, t-triplet, q-quartet, m-multiplet, b-broad, w-weak
**weaker couplings are underlined

TABLE 2

Summary Table of Carbon NMR, HMQC, and HMBC Peak Assignments

| Chemical Shift Tentative (ppm) | Number Of Carbons | HMQC Couplings | HMBC Couplings | Assignments |
|---|---|---|---|---|
| 8.6 | 3 | 1.17 | — | 20 |
| 15.8 | 1 | 0.52 | 12, 13, 17 | 18 |
| 23.4 | 1 | 2.99, 3.13 | 8, 9, 13 | 11 |
| 24.6 | 1 | 1.52, 2.16 | 8, 13, 16 | 15 |
| 29.2 | 1 | 1.73, 2.04 | 9, 11, 13, 18 | 12 |
| 32.9 | 1 | 1.60, 2.27 | 15, 17 | 16 |
| 39-40 | — | — | — | solvent-DMSO |
| 44.4 | 1 | — | — | 13 |
| 44.5 | 1 | 3.10 | 8, 9, 12, 13, 15, 18 | 14 |
| 45.7 | 1 | 3.09 | — | 19 |
| 48.5 | — | — | — | solvent-MeOH |
| 77.3 | 1 | 3.76 | 13, 15, 18 | 17 |
| 107.5 | 1 | 6.62 | 5, 6, 9, 14 | 7 |
| 111.7 | 1 | 7.85 | 2, 3, 6, 10 | 4 |
| 119.9 | 1 | — | — | 9 |
| 121.5 | 1 | 7.30 | 10 | 2 |
| 123.6 | 1 | 7.75 | 3, 5, 9, 10 | 1 |
| 123.7 | 1 | — | — | 5 |
| 129.4 | 1 | — | — | 10 |
| 136.0 | 1 | — | — | 8 |
| 149.4 | 1 | — | — | 3 |
| 150.7 | 1 | — | — | 6 |
| — | — | 4.50 | 13, 16, 17 | 17(OH) |
| — | — | 9.64 | 5, 6, 7 | 6(OH) |

1D and 2D NMR Spectral Interpretation

Peak A is a derivative of dihydroequilenin, which contains five aromatic protons and ten aliphatic protons. The $^1$H-NMR spectrum exhibits the ten expected aliphatic protons, but only four main signals were observed in the aromatic region (6.5-8.0 ppm) of the $^1$H-NMR (FIG. 8) that corresponded to a 1:1:1:1 ratio. Based upon the splitting expected from the proposed structure for Peak A, these signals were consistent with a dihydroequilenin based ring structure substituted at one of the aromatic protons. The four aromatic $^1$H-NMR signals showed a strong singlet and a strong doublet, and a second singlet and doublet, which are weakly split into doublets.

Substitution at each of the possible aromatic positions may create a distinct splitting pattern. Substitution at the 1-position may create a single pair of strong doublets (H6 and H7) with a strong COSY correlation and a pair of singlets (H4 and H2) which may exhibit a weak COSY correlation and be weakly split by each other. Substitution at the 2-position may create but a single pair of strong doublets (H6 and H7) with a strong COSY correlation and a pair of singlets (H4 and H1). Substitution of the aromatic ring system at the 4-position may create a pattern of 2 strong pairs of doublets with strong COSY correlations in the spectrum. Substitution at the 6- or 7-position may create but a single pair of strong doublets (H1 and H2) with a strong COSY correlation and a pair of singlets (H4 and H6 or H7). The H4 proton may be expected to interact weakly with the H2 proton exhibiting a weak COSY correlation and causing the H2 doublet and the H4 singlet to be weakly split by each other.

Figure 11:
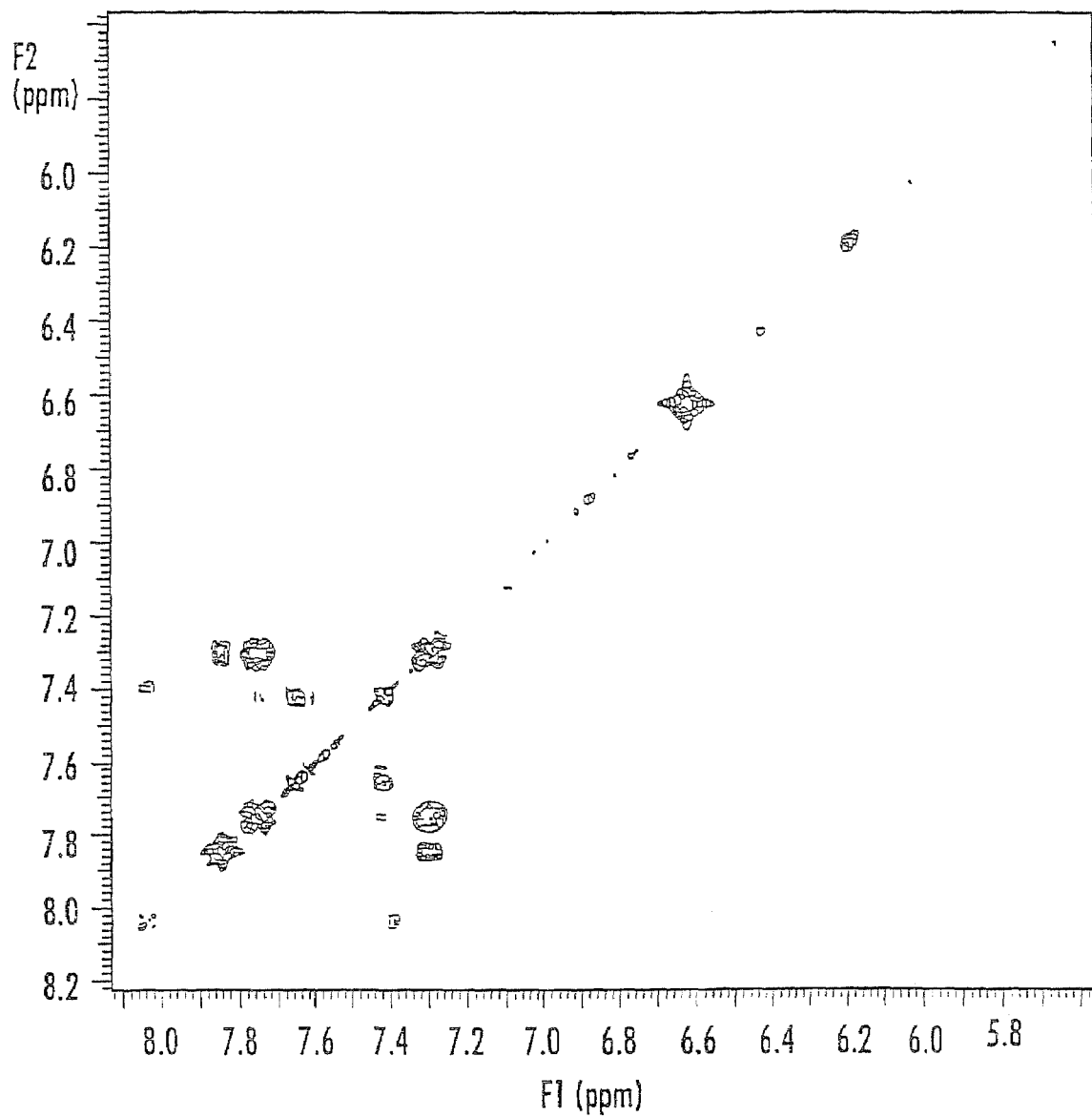
FIG. 11 is a 400 MHz 2D COSY $^1$H-NMR spectrum of the aromatic region of Peak A in $d_6$-DMSO.
Figure 12:
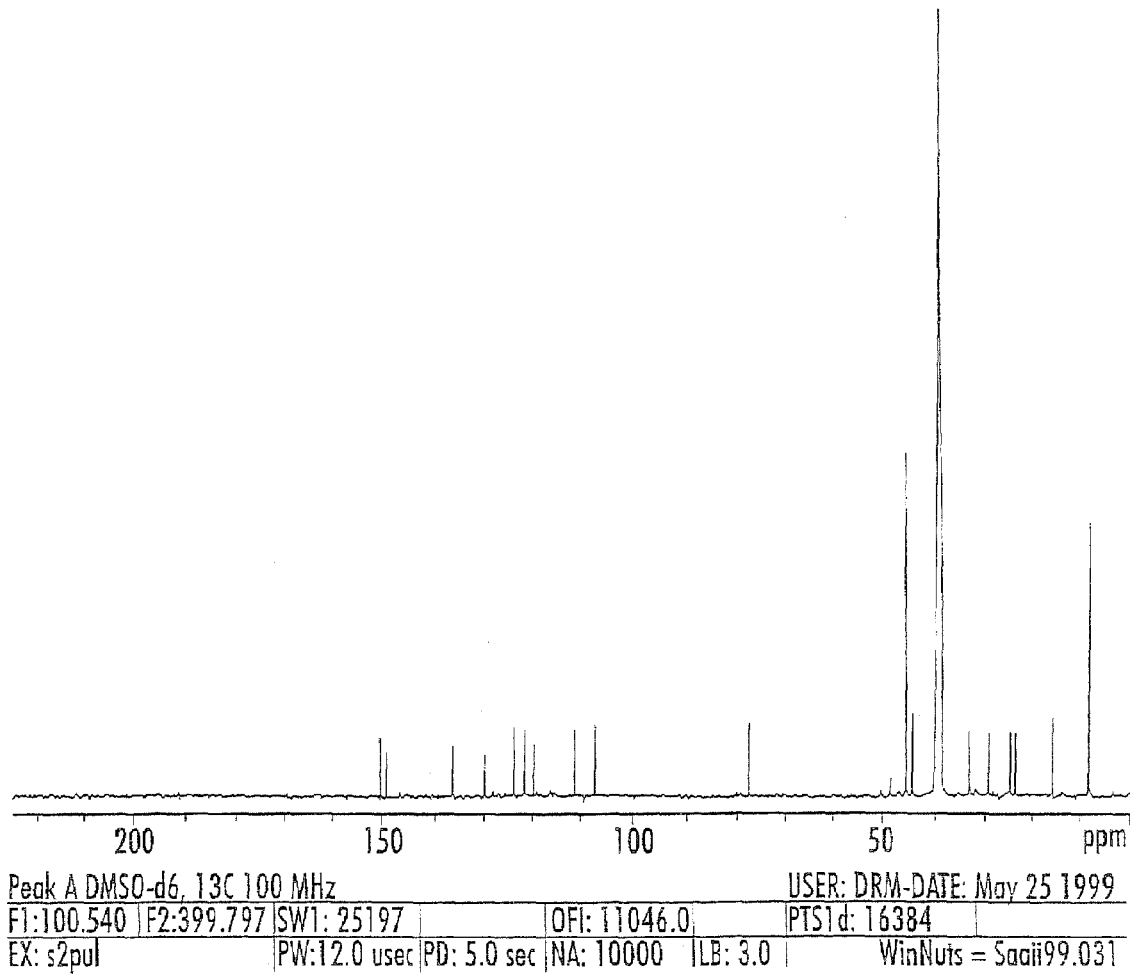
FIG. 12 is a full range 100 MHz $^{13}$C-NMR spectrum of Peak A in $d_6$-DMSO.
Figure 13:
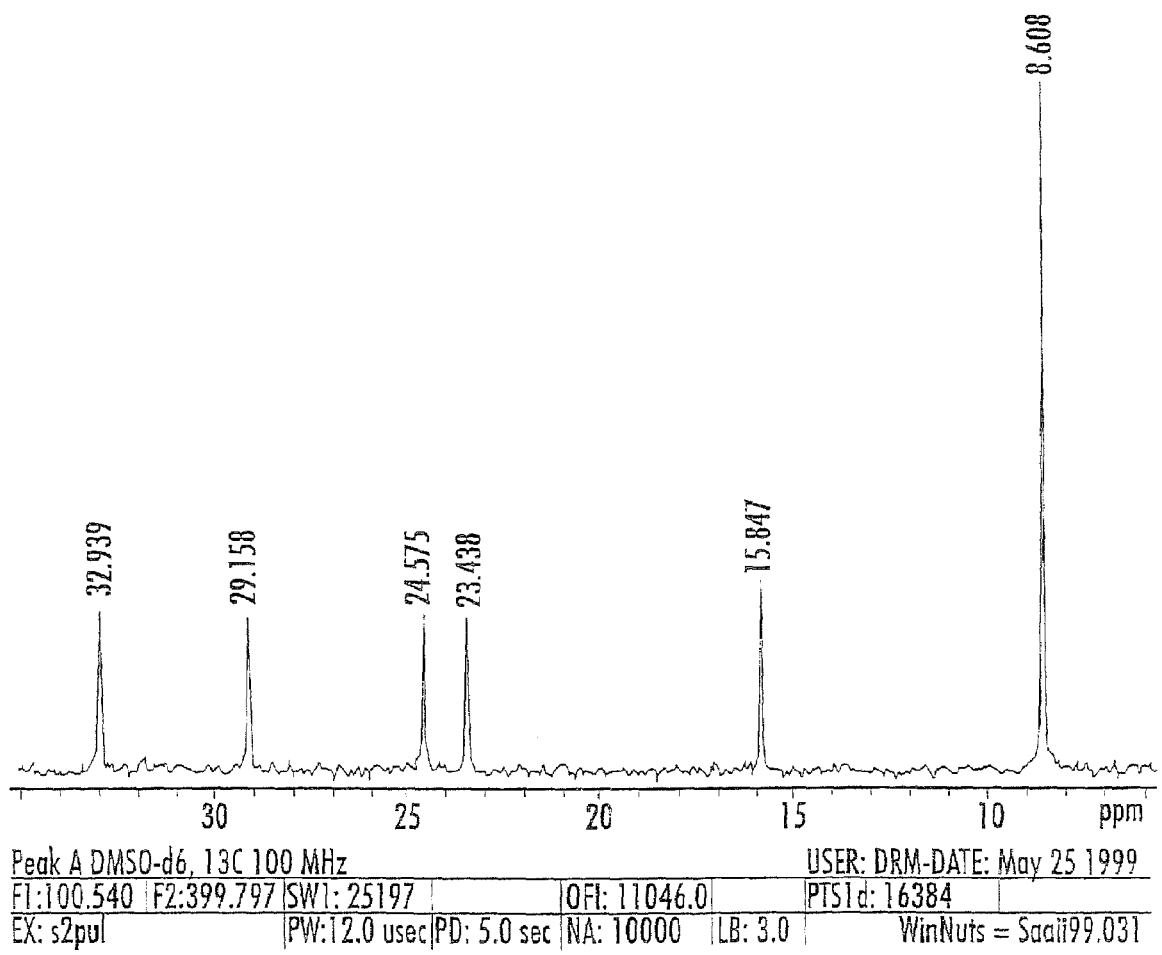
FIG. 13 is a 100 MHz $^{13}$C-NMR spectrum of the aliphatic region (0-40 ppm) of Peak A in $d_6$-DMSO.
Figure 14:
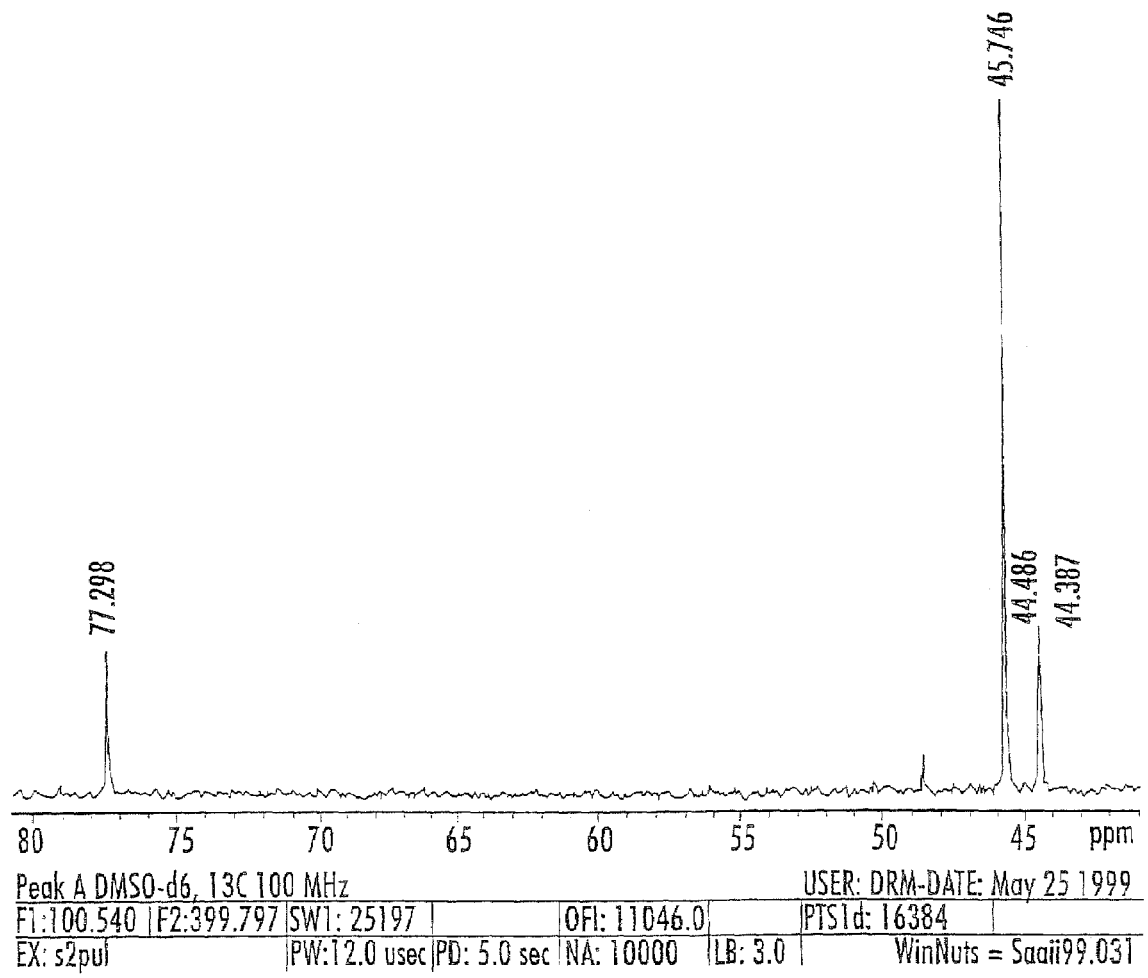
FIG. 14 is a 100 MHz $^{13}$C-NMR spectrum of the aliphatic region (40-80 ppm) of Peak A in $d_6$-DMSO.
Figure 15:
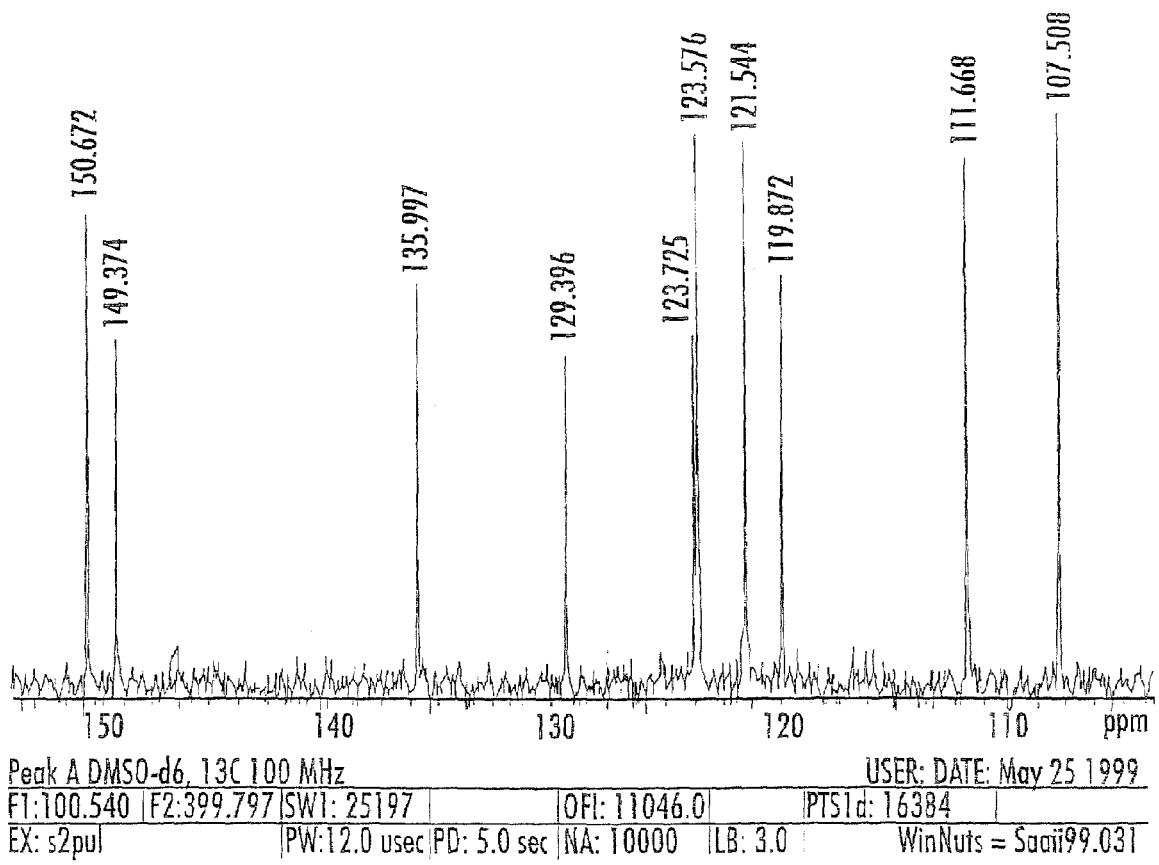
FIG. 15 is a 100 MHz $^{13}$C-NMR spectrum of the aromatic region of Peak A in $d_6$-DMSO.
Figure 16:
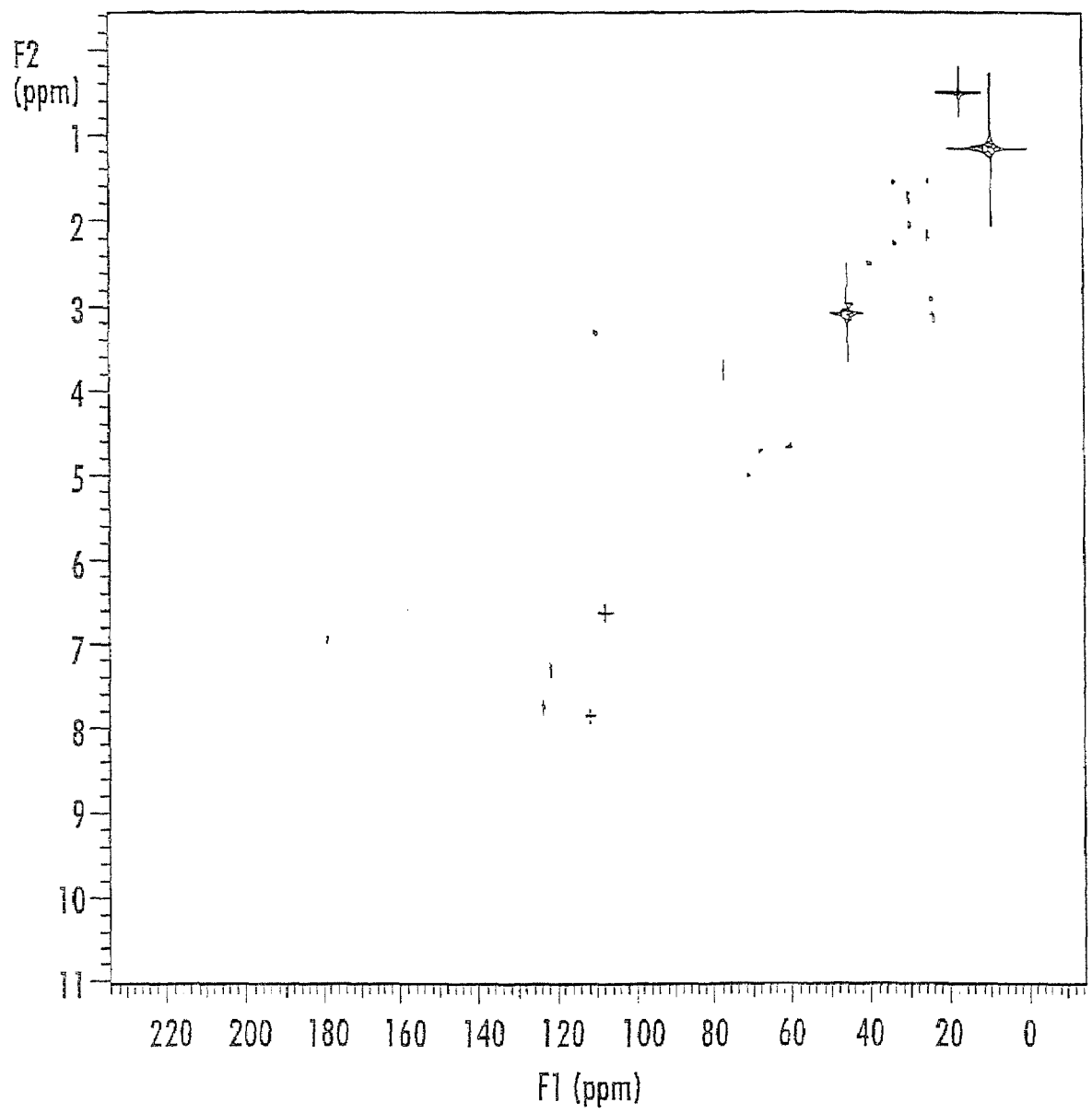
FIG. 16 is a full range 2D HMQC spectrum of the correlations of the protons and carbons of Peak A in $d_6$-DMSO.
Figure 19:
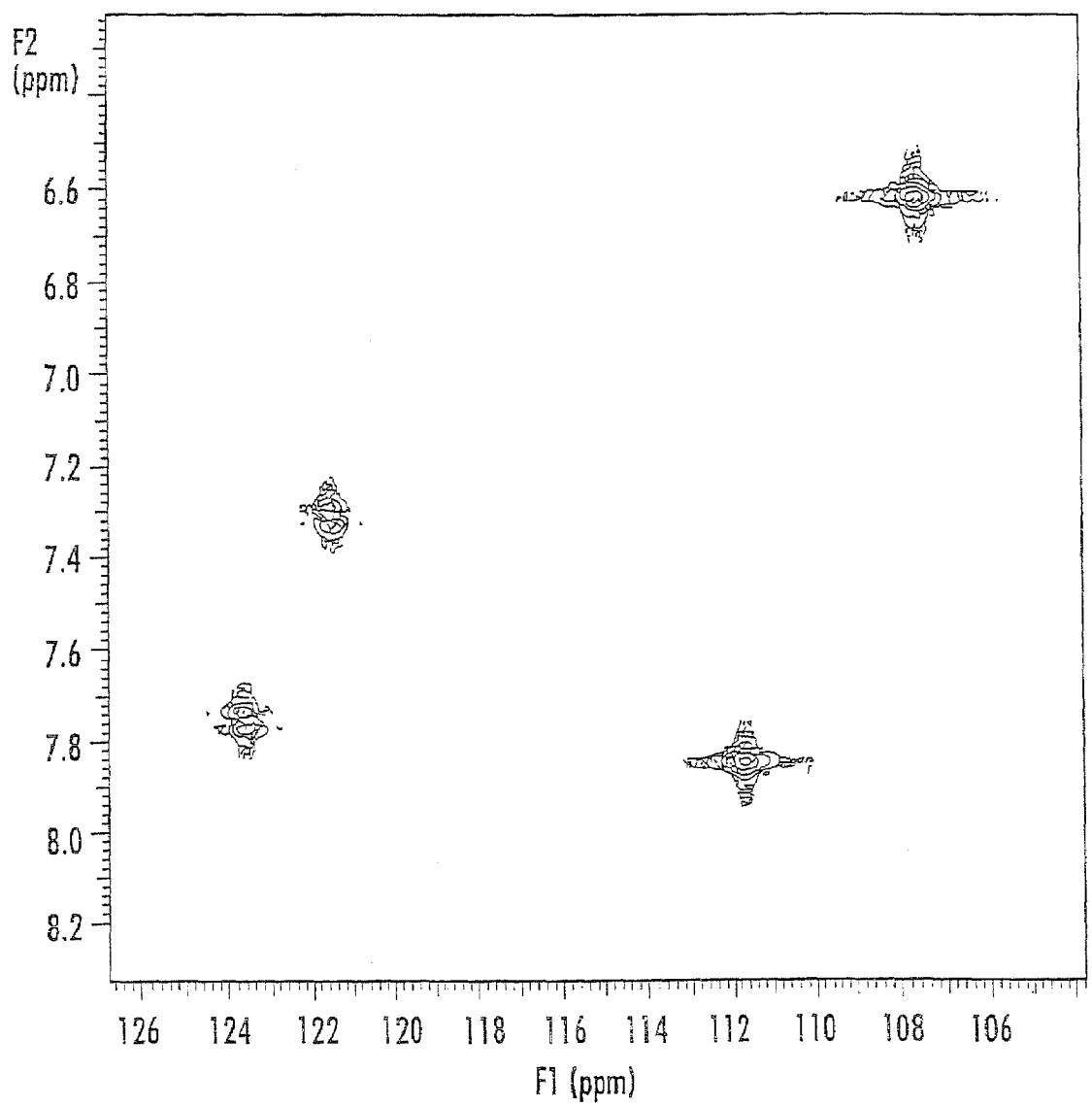
FIG. 19 is a 2D HMQC spectrum of the correlations of the aromatic protons and carbons in Peak A in $d_6$-DMSO.
Figure 20:
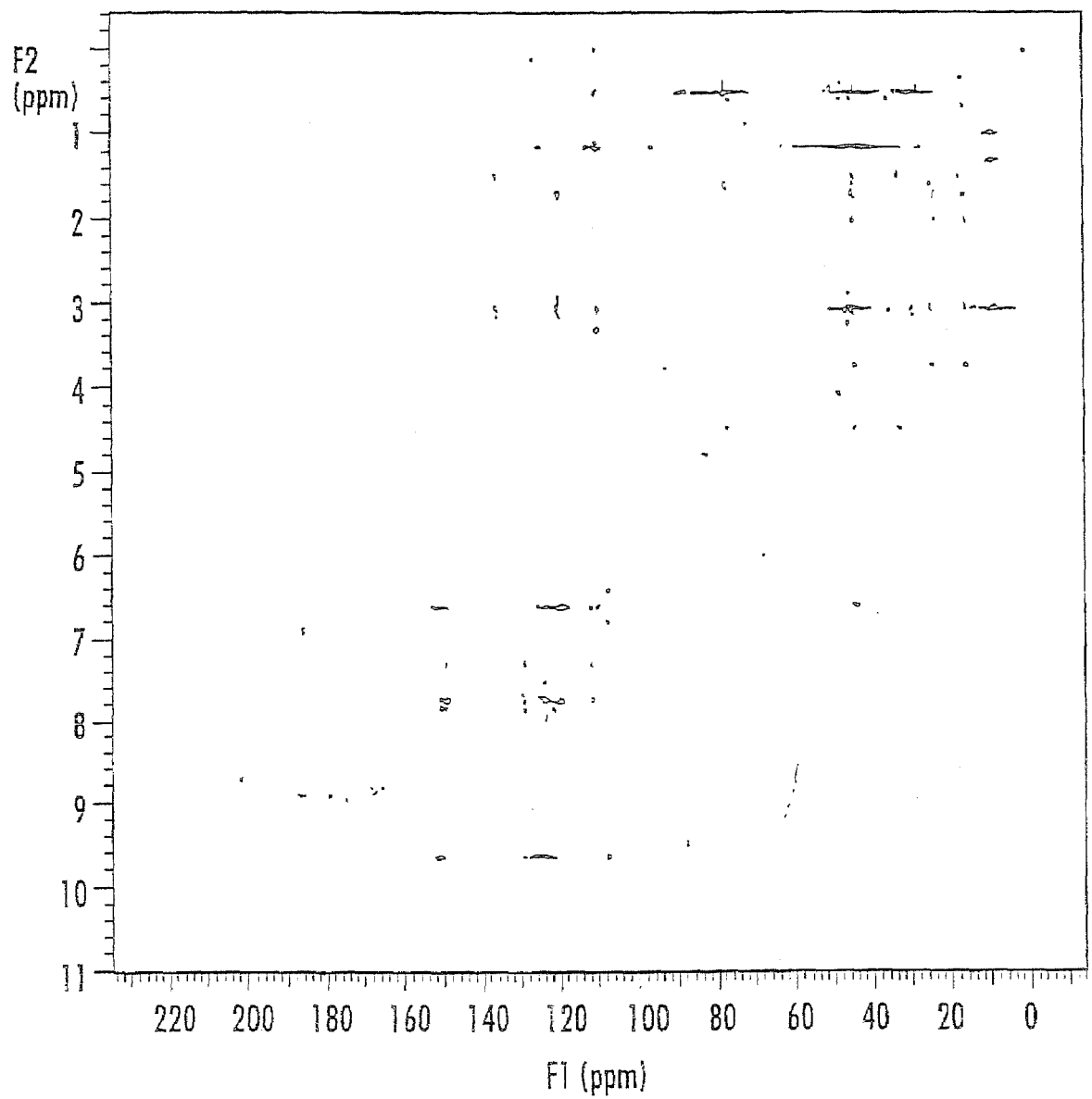
FIG. 20 is a full range 2D HMBC spectrum of the correlations of the protons and carbons in Peak A in $d_6$-DMSO.

Based upon the splitting pattern of the aromatic protons, substitution of the hydroxyl group in Peak A may be at either the H6 or H7 position. The pair of doublets at 7.75 and 7.30 ppm for H1 and H2, respectively, is shown to be adjacent from the 2D COSY spectrum (FIG. 11). H2 and H4 at 7.85 ppm exhibited a weak COSY correlation that caused H2 to appear as a doublet of doublets due to splitting by both H1 and H4; and H4 as a strong singlet weakly split to a doublet. The assignments of the corresponding carbons C1, C2, and C4 were based upon the HMQC spectra (FIG. 19) at 123.6, 121.5, and 111.7 ppm, respectively. The other aromatic ring contains only one proton at 6.62 ppm for H6 or H7, which was observed as a singlet as expected since no other protons are nearby to cause splitting. The corresponding carbon signal was assigned from the HMQC correlations at 107.5 ppm (FIG. 19).

In the $^{13}$C-NMR aromatic region (100-170 ppm) (FIG. 15), there were four large signals and six smaller signals. Protonated carbons may typically have larger signals than non-protonated carbons and that was used in differentiating among the aromatic carbon atoms. This was verified by observation of only four HMQC signals in this region, which occur only for carbons with directly attached protons, in the aromatic region (FIG. 19). The remaining six aromatic carbon signals did not have HMQC peaks, and are therefore, non-protonated.

Figure 23:
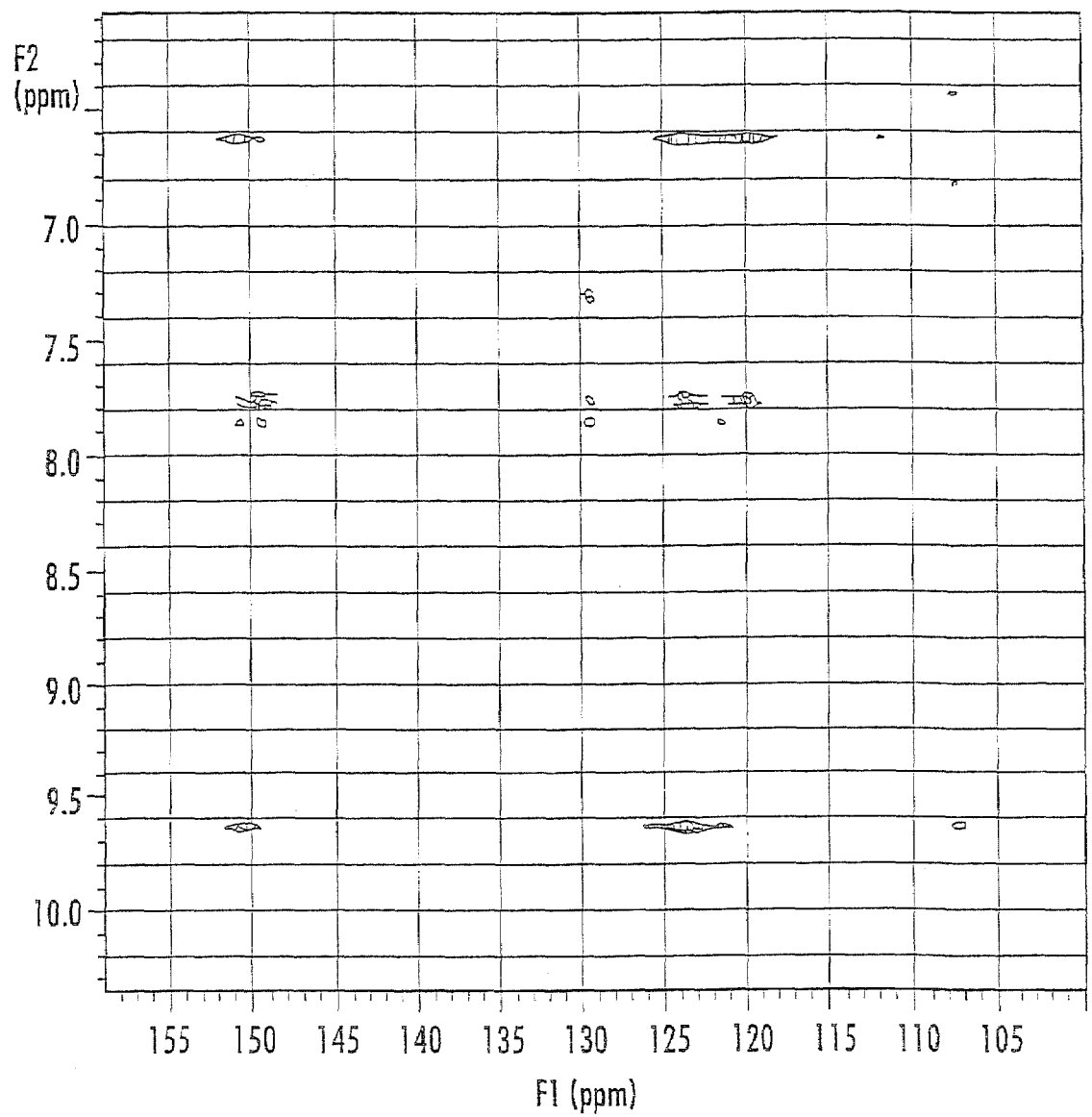
FIG. 23 is a 2D HMBC spectrum of the correlations of the aromatic protons and carbons in Peak A in $d_6$-DMSO.
Figure 24:
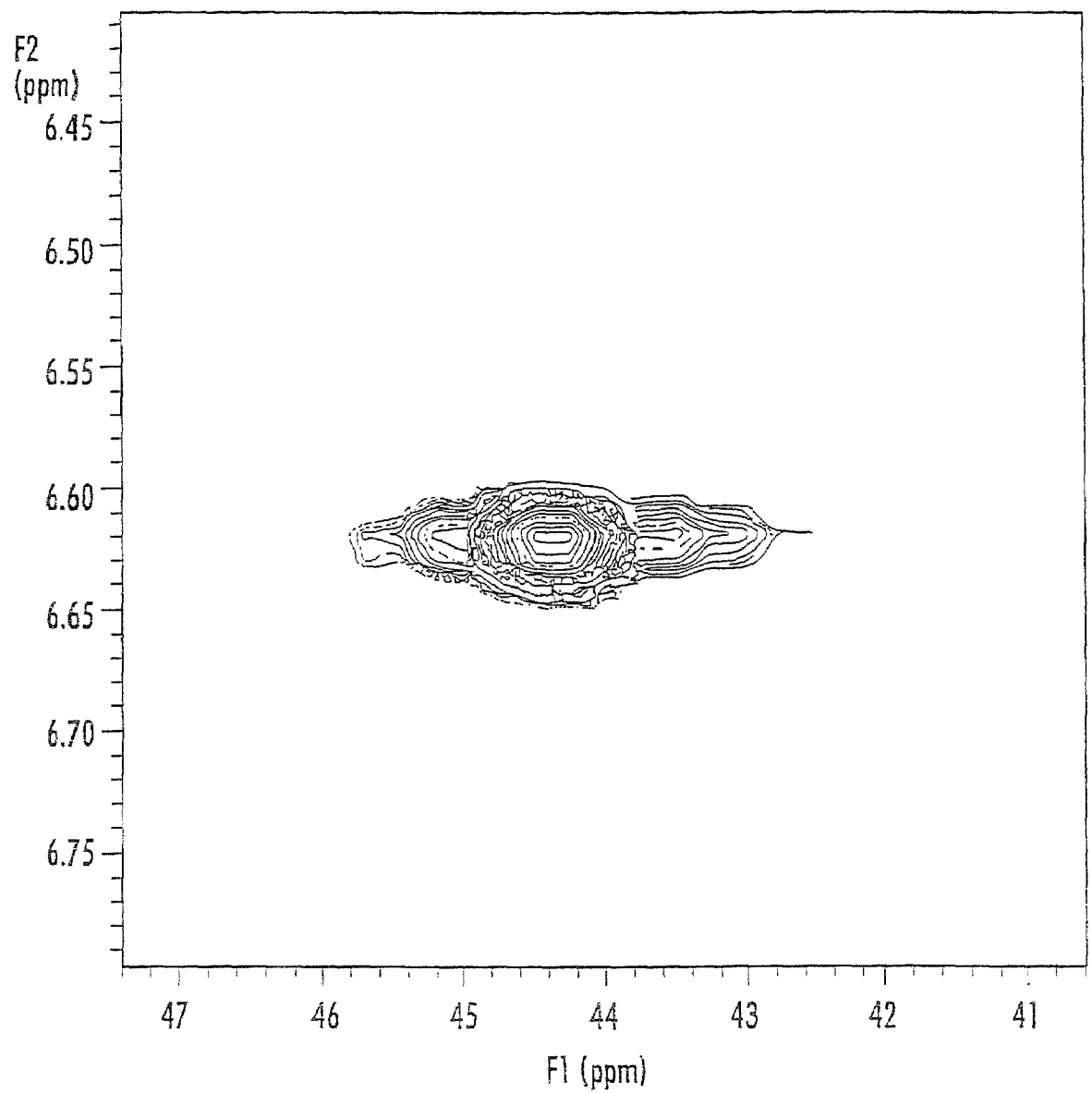
FIG. 24 is a 2D HMBC spectrum of the correlations of the aromatic protons and aliphatic carbons in Peak A in $d_6$-DMSO.

Two of the six non-protonated signals are shifted downfield to about 150 ppm (149.4 and 150.7 ppm), which may be typical of aromatic carbon atoms attached to an oxygen atom. This fits the proposed structure with the normal 3-position hydroxy sulfate ester and the proposed hydroxyl substitution on an aromatic position. The HMBC spectrum (FIG. 23) shows correlations of the carbon signals at 149.4 ppm to H1 and H4 and the carbon signal at 150.7 ppm to H4 and either H6 or H7. Based upon those correlations the signal at 149.4 ppm must be C3. The signal at 150.7 ppm must be C6 or the H4 correlation would have been a weak 4-bond correlation. Thus, the substitution is at the 6-position and the aromatic proton at 6.62 ppm and the aromatic carbon at 107.5 ppm are assigned H7 and C7, respectively. The remaining four non-protonated carbon atoms (119.9, 123.7, 129.4, and 136.0 ppm) match the number of bridging non-protonated carbon atoms expected for the proposed structure. Assignment of these four signals can be made from HMBC correlations (FIG. 23). H2 shows a single strong 3-bond correlation to the carbon signal at 129.4 ppm and is assigned C10 being the only bridging carbon atom within 3 bonds of H2. H1 exhibits three strong 3-bond correlations at 119.9, 123.7, and 149.4 (C3) ppm and one weak 2-bond correlation to 129.4 (C10) ppm. H4 exhibits HMBC correlations to 121.5 (C2), 129.4 (C10), 149.4 (C3), and 150.7 (C6) ppm. H7 exhibits HMBC correlations to aromatic signals at 119.9, 123.7, and 150.7 (C6) ppm. Based upon these correlations, the carbon signals at 119.9 and 123.7 ppm are for C5 and C9, but their exact assignments are not yet established.

Figure 8:
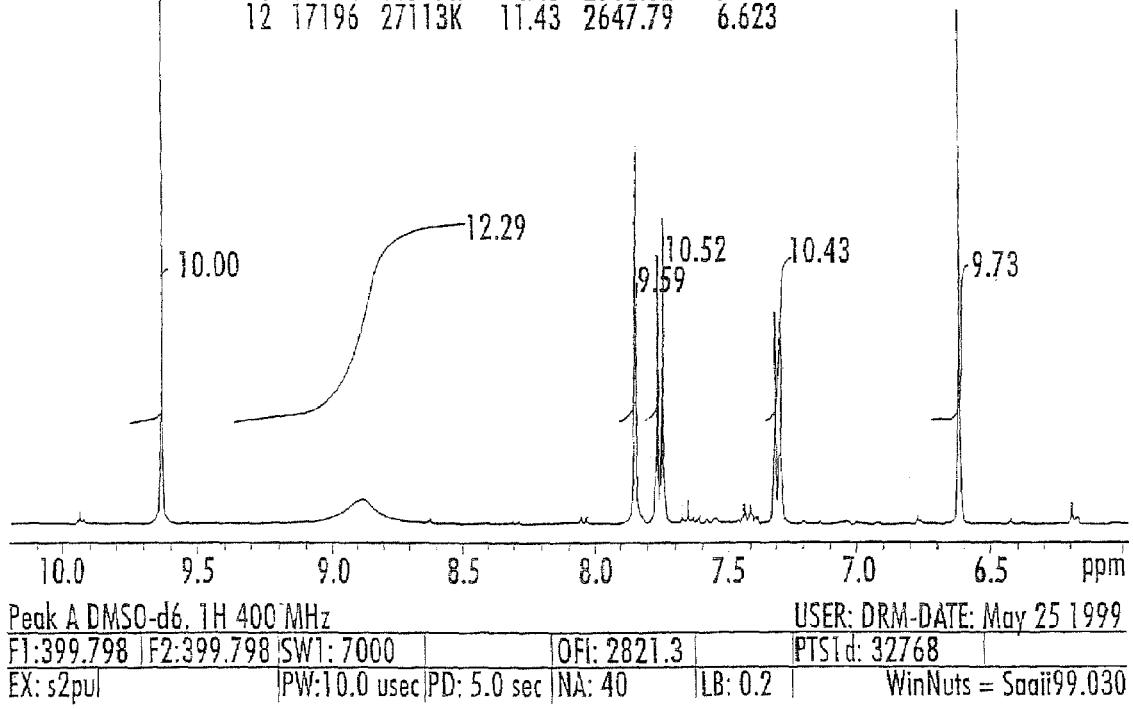
FIG. 8 is a 400 MHz $^1$H-NMR spectrum of the aromatic region of Peak A in $d_6$-DMSO.
Figure 9:
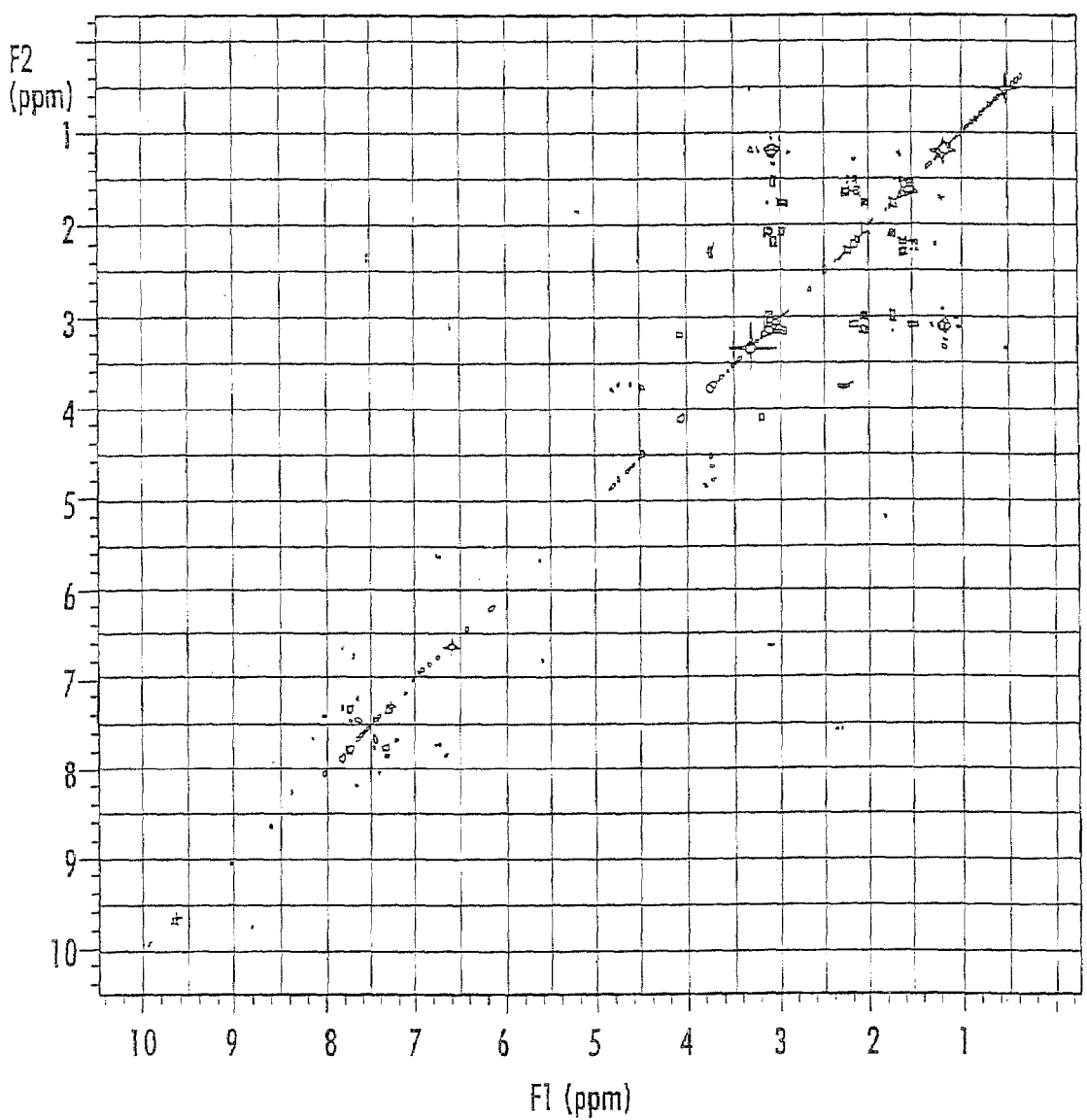
FIG. 9 is a full range 400 MHz 2D COSY $^1$H-NMR spectrum of Peak A in $d_6$-DMSO.

There is a single strong signal downfield in the $^1$H-NMR spectrum at 9.64 ppm (FIG. 8). This region is typical of aromatic phenolic protons and this signal is assigned as H6(OH). HMBC spectrum for this proton exhibits correlations at 107.5 (C7), 123.7, and 150.7 (C6) ppm (FIG. 23). Based upon these correlations and the relationships of the other protons the signal at 123.7 ppm must be C5 and thus the signal at 119.9 ppm must be C9. This leaves only the aromatic carbon signal at 136.0 ppm unassigned. Thus, the remaining aromatic signal by process of elimination was assigned as C8.

Figure 10:
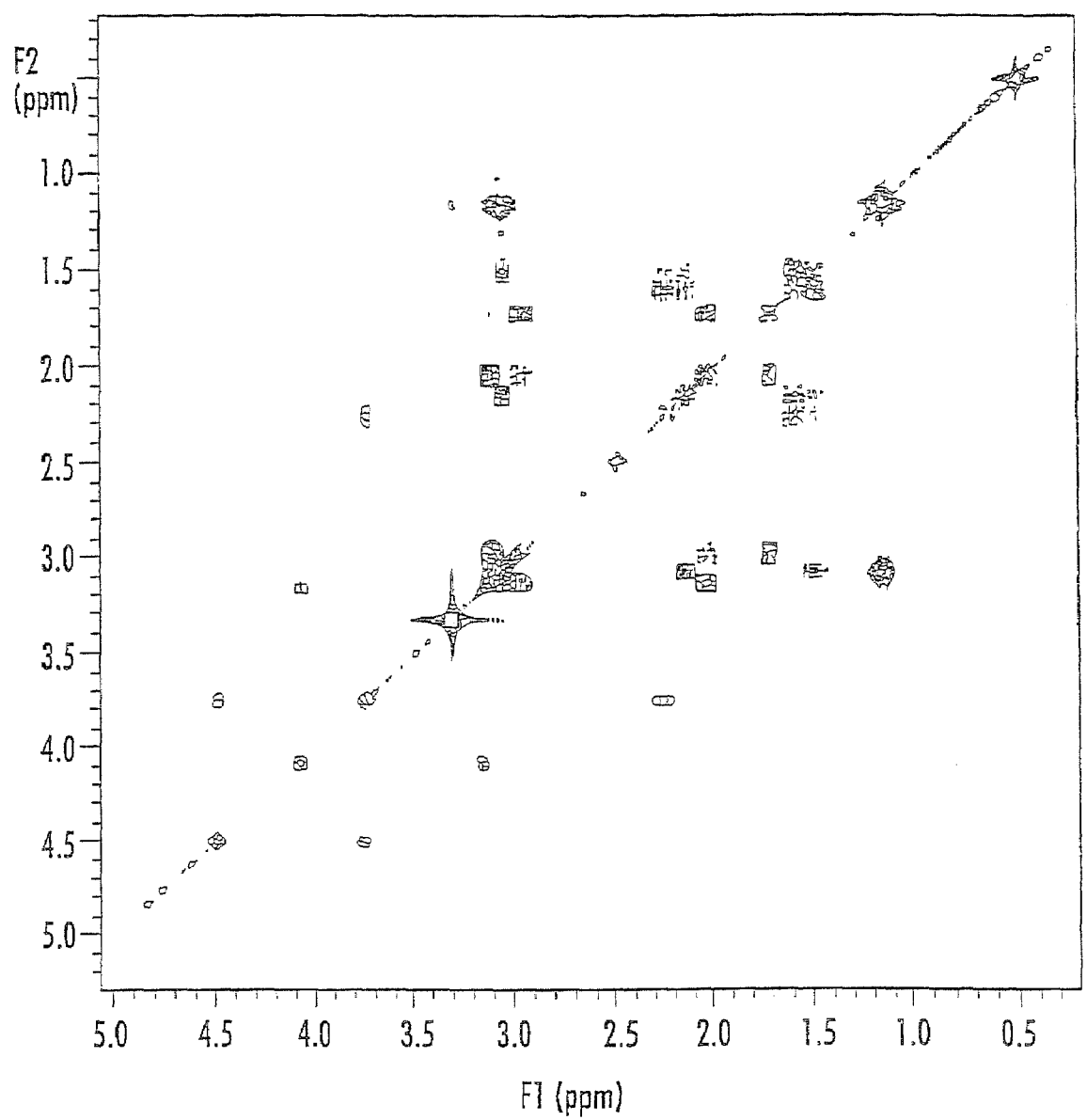
FIG. 10 is a 400 MHz 2D COSY $^1$H-NMR spectrum of the aliphatic region of Peak A in $d_6$-DMSO.

The methyl region (0.5 to 1.5 ppm) of the $^1$H-NMR spectrum (FIG. 7) shows a strong methyl signal split into a triplet at 1.17 ppm that is indicative of the methyl proton (H20) of the triethyl ammonium cation. This signal shows a strong COSY correlation to the quartet signal at 3.09 ppm for the protons (H19) of the methylene group (FIG. 10). The HMQC correlation spectrum (FIG. 17) showed corresponding carbon atoms at 8.6 and 45.7 ppm for C20 and C19, respectively. The amine proton (NH$^+$) of the cation was expected to have a $^1$H-NMR chemical shift of about 8.0 to 9.5 ppm; however, amines have the problem of slow exchange and often are not seen, or are only seen as a small broad peak in this region. The NH proton in the $^1$H-NMR spectrum was observed as a single broad signal at about 8.90 ppm for this compound (FIG. 8).

Figure 17:
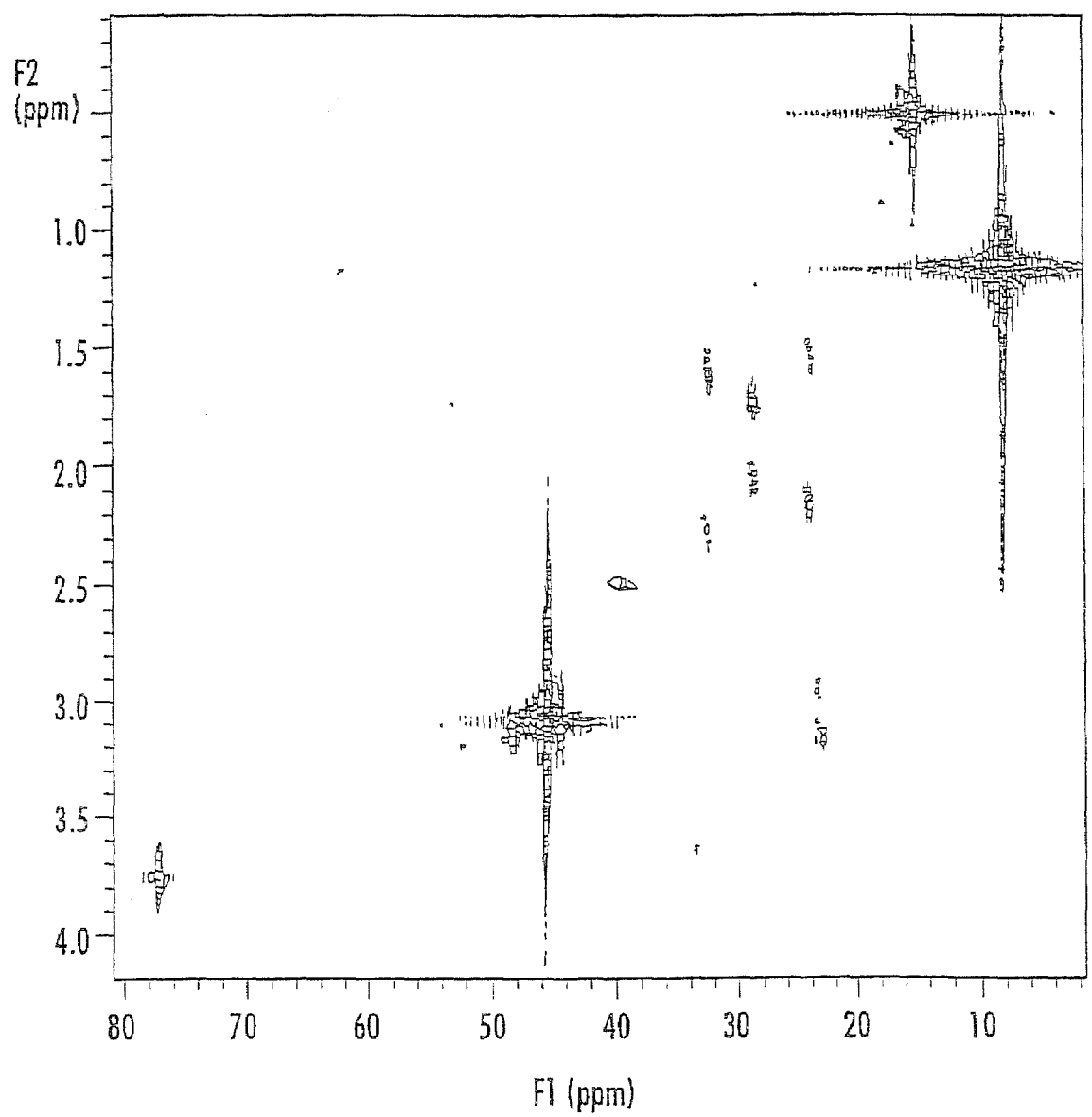
FIG. 17 is a 2D HMQC spectrum of the correlations of the aliphatic protons and carbons in Peak A in $d_6$-DMSO.
Figure 18:
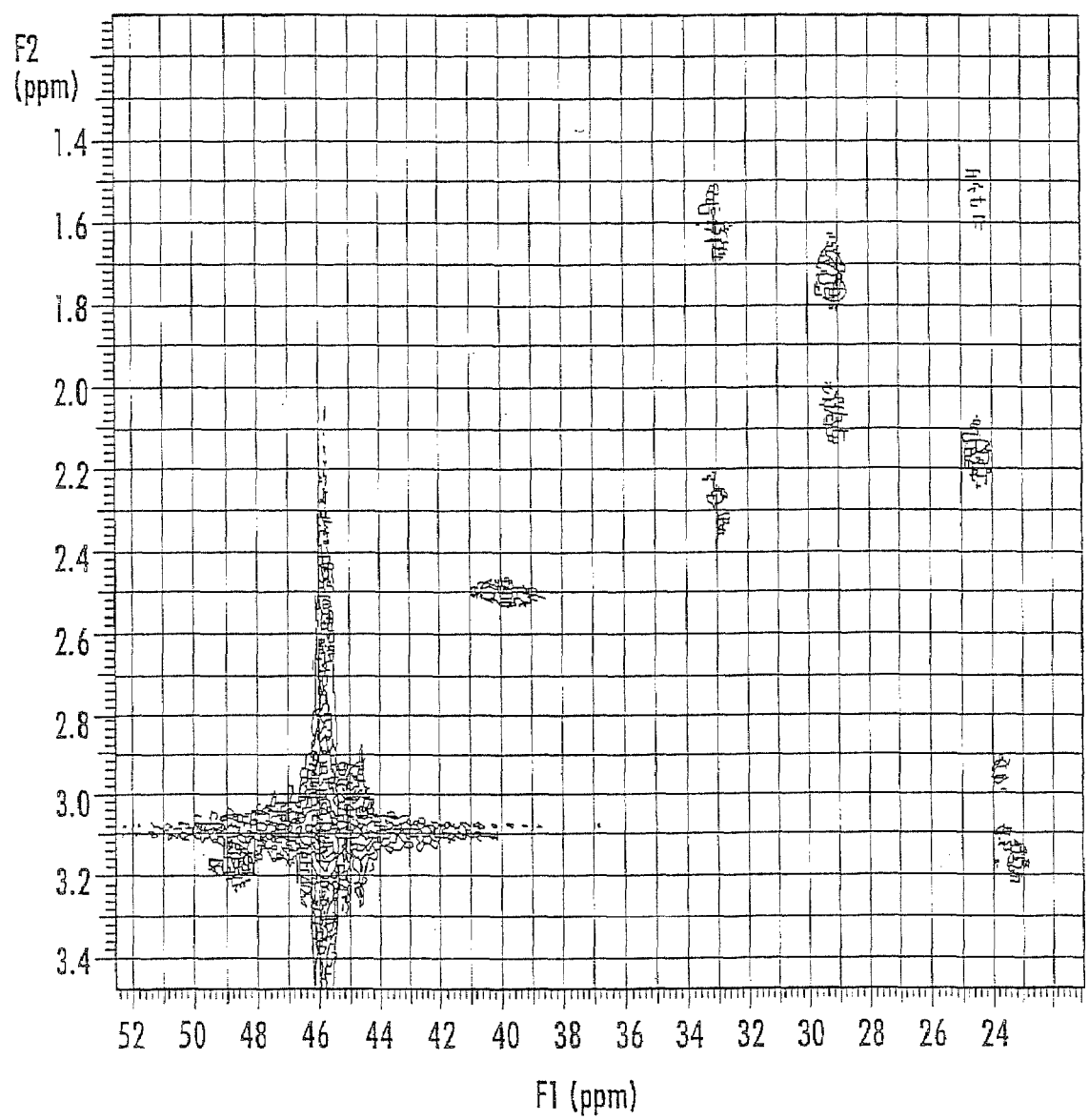
FIG. 18 is a 2D HMQC spectrum of the correlations of the aliphatic protons and carbons (Zoom-in of FIG. 17) in Peak A in $d_6$-DMSO.

In the $^{13}$C-NMR aliphatic region (0-100 ppm) (FIGS. 13-14), there were two strong signals at 8.6 and 45.7 ppm for the triethyl ammonium cation, and eight signals for the aliphatic carbons of Peak A. The proposed structure for Peak A contains eight aliphatic carbon atoms. The eight aliphatic carbon signals were observed at 15.8, 23.4, 24.6, 29.2, 32.9, 44.4, 44.5, and 77.3 ppm. Seven of the eight signals show HMQC correlations to proton signals (FIGS. 17-18). Only the carbon signal at 44.4 ppm did not exhibit a correlation to any proton signal and was considered a bridging carbon. The proposed structure has one bridging aliphatic carbon atom, and thus the peak at 44.4 ppm was assigned as C13. The three carbon signals at 15.8, 44.5, and 77.3 ppm each correlated to a single proton signal whereas the other four carbon signals observed at 23.4, 24.6, 29.2, and 32.9 ppm each correlated to two proton signals. This may be the case in saturated aliphatic ring systems since the two protons of the methylene groups are present in differing electronic environments and thus, exhibit different chemical shifts.

Inspection of the three carbon signals with a single proton HMQC correlation shows that the signal at 15.8 ppm is in the expected methyl region for $^{13}$C-NMR and correlates by HMQC to the proton signal at 0.52 ppm. These protons exhibited the expected integration ratio for a methyl group of 3:1 relative to the individual aromatic protons and are assigned as H18 based on the chemical shift and the HMQC correlations and is the only methyl group in the proposed structure for Peak A. The signal for the carbon atom (C17) attached to the hydroxyl group is expected to shift downfield relative to the other aliphatic signals, as described for the aromatic carbon signals. Thus, the carbon signal observed at 77.3 ppm was assigned as C17 based upon chemical shift and the HMQC correlated proton signal at 3.76 ppm was assigned as H17. There is only one remaining carbon atom with one proton, thus, the signal at 44.5 ppm was assigned as C14 and the proton signal at 3.10 ppm correlated to it by HMQC was H14.

The remaining four aliphatic carbon signals each exhibited two HMQC correlations to proton signals. The carbon signal at 23.4 ppm correlates to the protons at 2.99 and 3.13 ppm. The COSY spectrum (FIG. 10) of these two protons show that they couple to the proton signals at 1.73 and 2.04 ppm indicating the two sets are adjacent. The HMQC spectrum (FIG. 17) shows these protons both correlate to the carbon signal at 29.2 ppm. The carbon signal at 24.6 ppm correlates to the protons at 1.52 and 2.16 ppm. The COSY spectrum of these two protons show that they couple to the proton signals at 1.60 and 2.27 ppm, indicating the two sets are adjacent. The HMQC spectrum shows these protons both correlate to the carbon signal at 32.9 ppm. These observations are consistent with the proposed structure of Peak A that has two sets of adjacent methylene groups at C11 and C12, and at C15 and C16.

Figure 21:
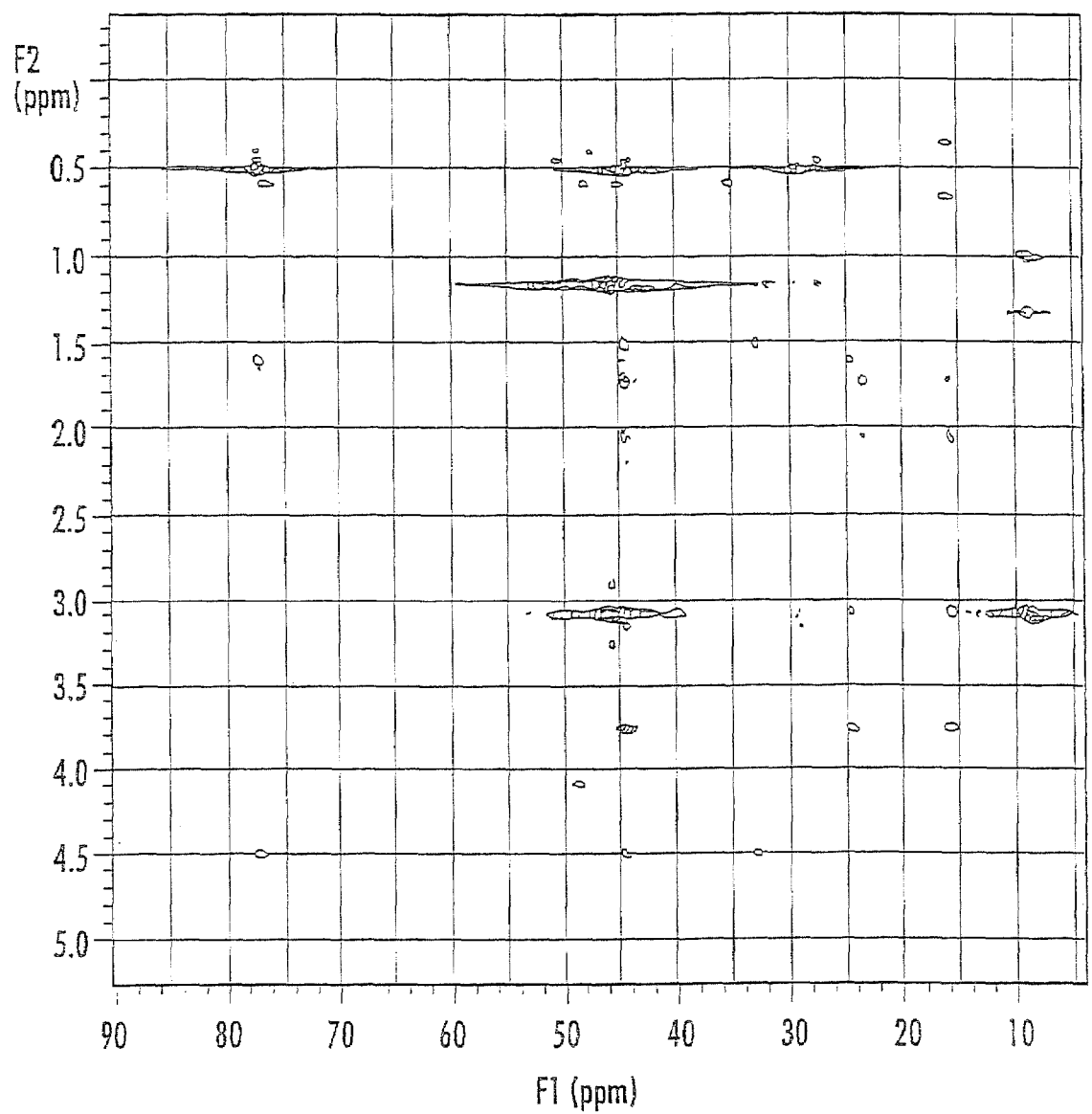
FIG. 21 is a 2D HMBC spectrum of the correlations of the aliphatic protons and carbons in Peak A in $d_6$-DMSO.
Figure 22:
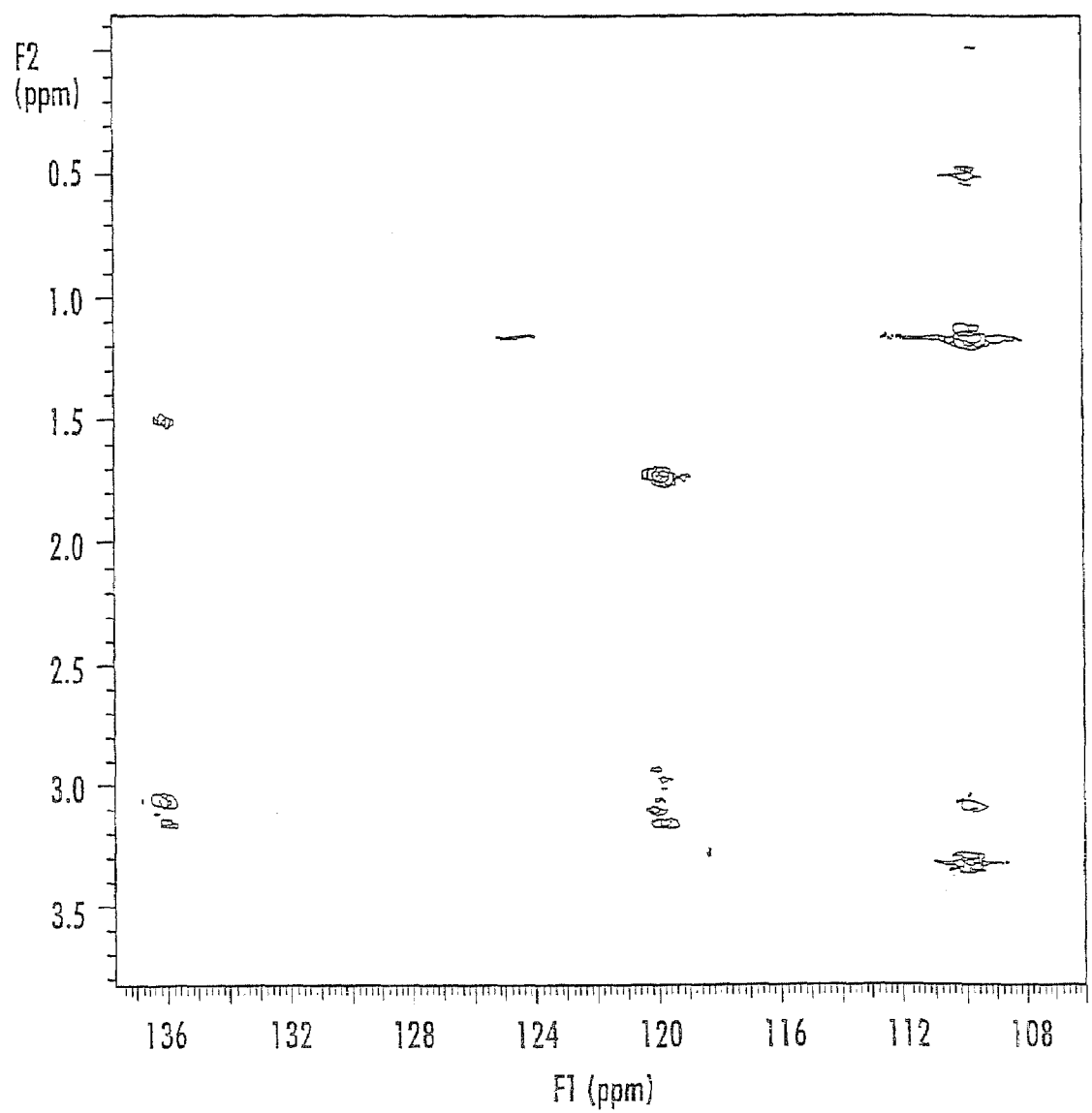
FIG. 22 is a 2D HMBC spectrum of the correlations of the aliphatic protons and aromatic carbons in Peak A in $d_6$-DMSO.

HMBC couplings (FIGS. 21-22) can be used to ascertain the identity and position of each of the four methylene groups. The bridging carbon at 119.9 (C9) ppm correlates to only the protons of, the carbon signals at 23.4 and 29.2 ppm (FIG. 22). This observation verifies that the carbon signals at 23.4 and 29.2 ppm must be assigned as C11 and C12 and that the other two carbon signals at 24.6 and 32.9 ppm must be assigned as C15 and C16, but their exact assignments have not yet been established. The proton at 0.52 (H18) ppm shows a HMBC correlation to the carbon signals at 29.2, 44.4 (C13), and 77.3 (C17) ppm (FIG. 21). Based upon this, the carbon signal at 29.2 ppm was assigned as C12 and thus, the carbon signal at 23.4 ppm must be C11. Based upon the HMQC correlations (FIG. 18) of each of these carbon signals, the proton signals at 2.99 and 3.13 ppm can be assigned as H11a and H12b, respectively, and the protons at 1.73 and 2.04 ppm can be assigned as H12a and H12b, respectively. The proton at 3.76 (C17) ppm shows COSY correlations to the protons at 2.27 ppm and 4.50 ppm (FIG. 10). Based upon the COSY correlations of the proton signal at 2.27, it must be adjacent to H17 and thus the carbon signal at 32.9 ppm must be C16 and the carbon signal at 24.6 ppm must be C15. Based upon the HMQC correlations (FIG. 18) of each of the carbon signals, the proton signals at 1.52 and 2.16 ppm can be assigned as H15a and H15b, respectively, and the protons at 1.60 and 2.27 ppm can be assigned as H16a and H16b, respectively. The proton at 4.50 ppm adjacent to the 3.76 (C17) ppm proton must be H17(OH), which would be expect to shift downfield being directly attached to an oxygen atom. HMBC correlations of the proton at 4.50 ppm (H17(OH)) exhibit correlations to 32.9 (C16), 44.4 (C13), and 77.3 (C17) ppm carbon signals (FIG. 21). Other HMBC correlations are detailed in Table 2 above and are consistent with the proposed structure of Peak A.

Additional signals in the proton NMR spectrum (FIGS. 7-8) were observed from water at 3.33 ppm, DMSO at 2.50 ppm, a small amount of methanol at 3.17 and 4.09 ppm, and other assorted small, unidentified aromatic and aliphatic "impurity" signals.

In addition to the expected aromatic and aliphatic signals of Peak A, there are two other significant HMQC signals (FIG. 17). The solvent (d$_6$-DMSO) was observed at 39.5 ppm (HMQC peak at 2.50 ppm), and the methanol was observed at 48.5 ppm (HMQC peak at 3.17 ppm).

Based on the observed NMR data the structure of Peak A corresponds well to the proposed structure.

Example 6

Peak B Characterization

Separation and Isolation

Figure 25:
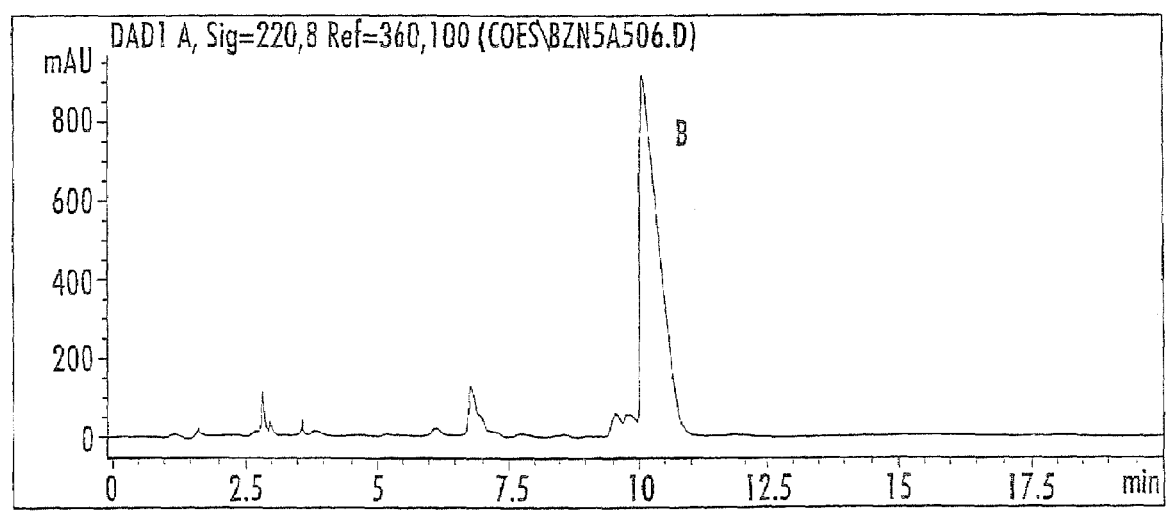
FIG. 25 is a HPLC Chromatogram using chromatographic method 4 showing re-injection of Peak B to determine its approximate purity.

Peak B was isolated as a triethyl ammonium salt due to the ion-pairing agent of the mobile phase of the HPLC chromatographic method described above in Example 3. After the fraction was collected, most of the ACN was removed by rotary evaporation, and the fraction was further concentrated using a $C_{18}$ SPE cartridge, washed with water, and eluted with approximately 10 mL of methanol. The fraction was then brought to dryness under a stream of dry nitrogen. Using the HPLC method described in Example 4, a small portion of the 20.2 mg of Peak B isolated for testing by MS and NMR was redissolved in mobile phase and injected on the HPLC system to determine the purity of the fraction. This injection of Peak B showed a purity of about 82% (FIG. 25).

Mass Spectral Analyses

Figure 26:
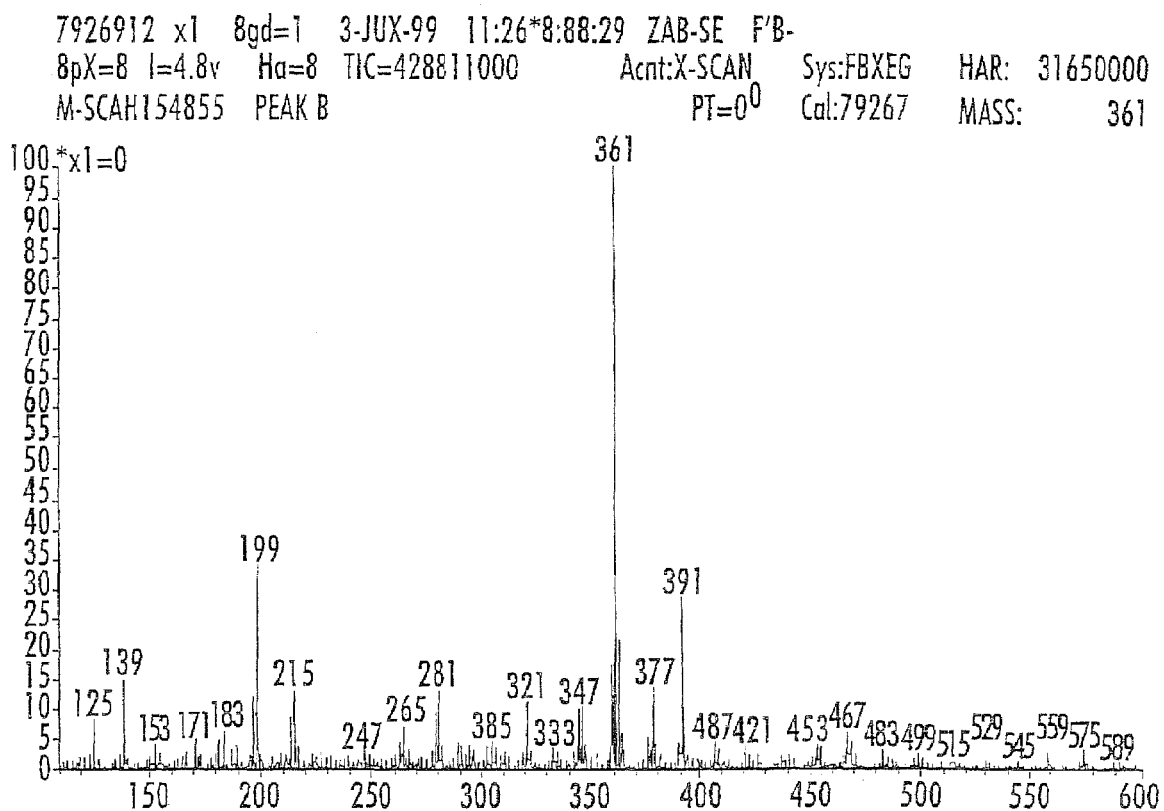
FIG. 26 is a low resolution negative ion FAB-MS spectrum of Peak B.
Figure 27:
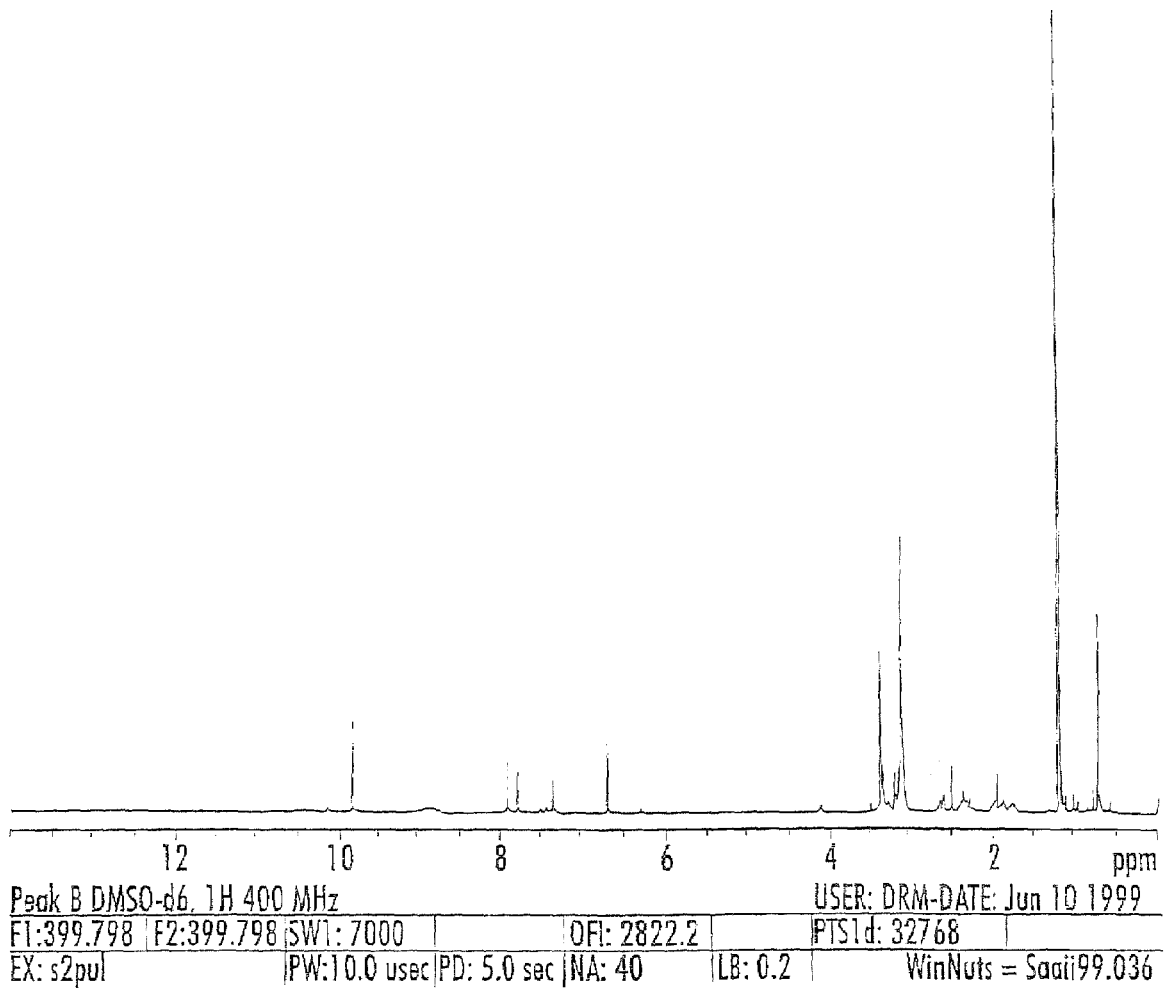
FIG. 27 is a full range 400 MHz $^1$H-NMR spectrum of Peak B in $d_6$-DMSO.
Figure 28:
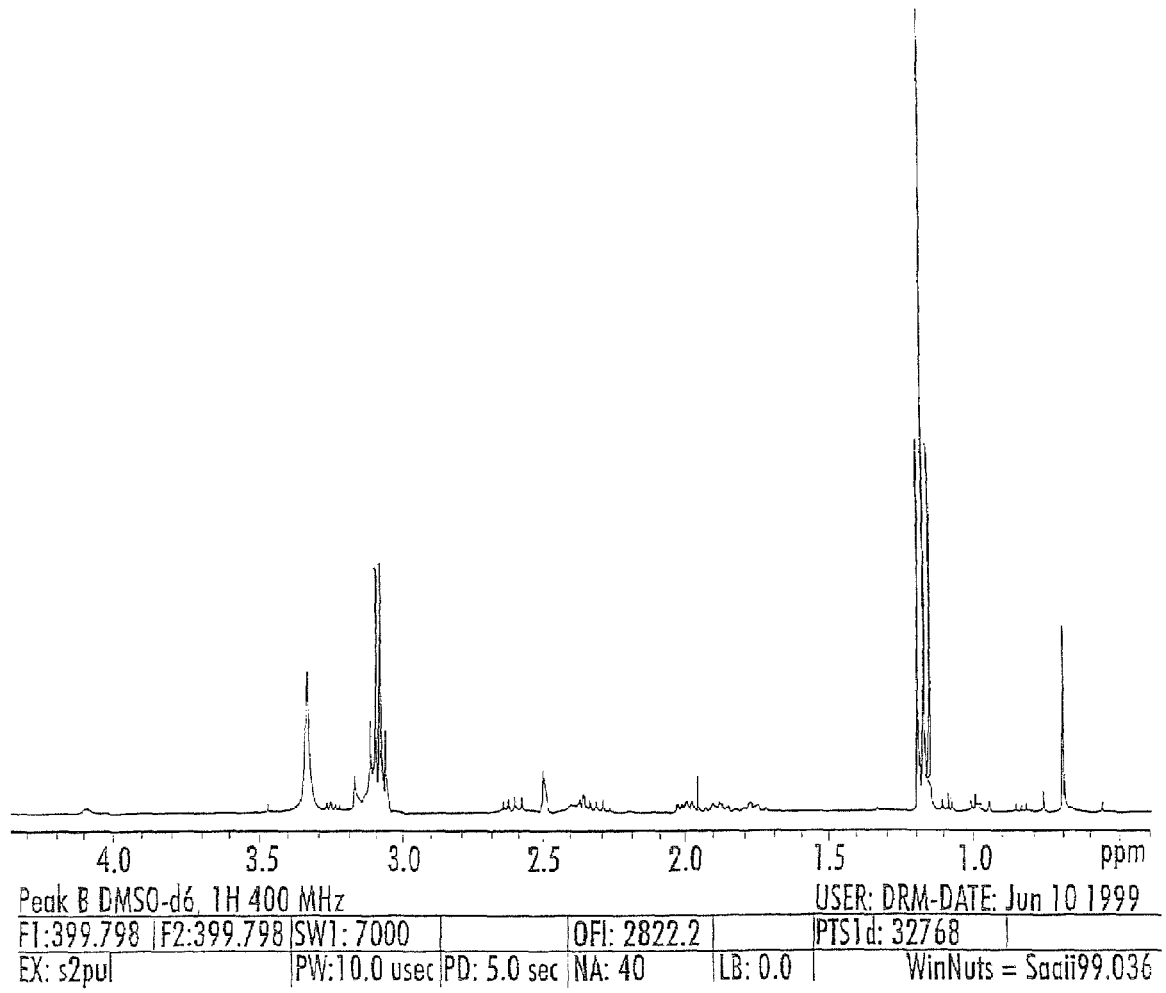
FIG. 28 is a 400 MHz $^1$H-NMR spectrum of the aliphatic region of Peak B in $d_6$-DMSO.

Preliminary negative ion FAB-MS spectral data of the isolated fraction of Peak B indicated that the molecular weight was approximately 361 m/z (FIG. 26). A negative ion HR-MS study indicated a mass of 361.0744 amu that compares well with the calculated mass of 361.0746 amu for the proposed molecular formula of $C_{18}H_{17}O_6S_1$ for Peak B.

Proton ($^1$H) and 2D COSY Nuclear Magnetic Resonance Spectroscopy

The $^1$H-NMR and the 2D COSY spectra of Peak B in deuterated dimethyl sulfoxide (d6-DMSO) are shown in FIGS. 27-29 and 30-32, respectively. The peak assignments, based upon the proton NMR spectra and COSY spectral couplings, are shown in Table 3 and are fully consistent with the structure of Peak B.

Carbon ($^{13}$C), 2D HMQC, and 2D HMBC Nuclear Magnetic Resonance

The $^{13}$C-NMR, HMQC, and HMBC spectra of Peak B in deuterated dimethyl sulfoxide ($d_6$-DMSO) are shown in FIGS. 33-37, 38-41, and 42-47, respectively. In order to collect the data more quickly and with a greater signal to noise ratio, the $^{13}$C-NMR spectrum was obtained non-quantitatively, and integrations were not performed. Peak assignments based upon the carbon NMR, HMQC, and HMBC spectral interpretations are shown in Table 4, and are fully consistent with the proposed structure of Peak B. 2D HMBC data can be more difficult to interpret, since it is possible that all crosspeaks are not observed. HMBC signals typically occur with H—C connectivities that are 2 to 4 bonds removed, but also can detect some 1 to 2 bond connections.

TABLE 3

Summary Table of Proton NMR and COSY Band Assignments

| Chemical Shift Tenative (ppm) | Multiplicty* | Number Of Protons | COSY Couplings** | Assignment |
|---|---|---|---|---|
| 0.70 | s | 3 | — | 18 |
| 1.17 | t | 9 | 19 | 20 |
| 1.78 | m | 1 | 11b, 12b | 12a |
| 1.88 | m | 1 | 14, <u>15b</u>, 16b | 15a |
| 2.00 | m | 1 | 11a, 12a | 12b |
| 2.32 | m | 1 | 16b | 16a |
| 2.39 | m | 1 | 14, <u>15a</u> | 15b |
| 2.50 | — | — | — | solvent-DMSO |
| 2.62 | m | 1 | 15a, 16a | 16b |
| 3.08 | m | 1 | 12b | 11a |
| 3.10 | q | 6 | 20 | 19 |
| 3.12 | m | 1 | 12a | 11b |
| 3.14 | d | 1 | <u>15a</u>, 15b | 14 |
| 3.18 | — | — | — | solvent-MeOH |
| 3.34 | — | — | — | solvent-H$_2$O |
| 4.10 | — | — | — | solvent-MeOH |
| 6.69 | s | 1 | — | 7 |
| 7.33 | d of d | 1 | 1, <u>4</u> | 2 |
| 7.77 | d | 1 | <u>2</u> | 1 |
| 7.89 | d(w) | 1 | <u>2</u> | 4 |
| 8.88 | bs | 1 | — | NH$^+$ |
| 9.83 | s | 1 | — | 6(OH) |

*s-singlet, d-doublet, t-triplet, q-quartet, m-multiplet, b-broad, w-weak
**weaker couplings are underlined

TABLE 4

Summary Table of Carbon NMR, HMQC, and HMBC Peak Assignments

| Chemical Shift Tenative (ppm) | Number Of Carbons | HMQC Couplings | HMBC Couplings | Assignments |
|---|---|---|---|---|
| 8.6 | 3 | 1.17 | — | 20 |
| 12.7 | 1 | 0.70 | 12, 13, 14, 17 | 18 |
| 21.4 | 1 | 1.88, 2.39 | 13, 14, 17 | 15 |
| 22.9 | 1 | 3.08, 3.12 | 8, 9, 12, 13 | 11 |
| 28.8 | 1 | 1.78, 2.00 | 9, 11, 13, 14 | 12 |
| 36.1 | 1 | 2.32, 2.62 | 14, 15, 17 | 16 |
| 39-40 | — | — | — | solvent-DMSO |
| 45.7 | 1 | 3.10 | — | 19 |
| 45.9 | 1 | 3.14 | 8, 9, 12, 13, 15, 18 | 14 |
| 46.9 | 3 | — | — | 13 |
| 48.5 | — | — | — | solvent-MeOH |
| 106.0 | 1 | 6.69 | 4, 5, 6, 9, 14 | 7 |
| 111.7 | 1 | 7.89 | 2, 3, 6, 10 | 4 |
| 120.1 | 1 | — | — | 9 |
| 121.8 | 1 | 7.33 | 3, 4, 10 | 2 |
| 123.7 | 1 | 7.77 | 3, 4, 5, 6, 9, 10 | 1 |
| 124.2 | 1 | — | — | 5 |
| 129.4 | 1 | — | — | 10 |
| 133.3 | 1 | — | — | 8 |
| 149.7 | 1 | — | — | 3 |
| 151.2 | 1 | — | — | 6 |
| 218.9 | 1 | — | — | 17 |
| — | — | 9.83 | 5, 6, 7, 10 | 6(OH) |

1D and 2D NMR Spectral Interpretation

Peak B is a derivative of equilenin, which contains five aromatic protons and ten aliphatic protons. The $^1$H-NMR spectrum exhibits the ten expected aliphatic protons, but only four main signals were observed in the aromatic region (6.5-8.0 ppm) of the $^1$H-NMR (FIG. 29) that corresponded to a 1:1:1:1 ratio. Based upon the splitting expected from the proposed structure for Peak B, these signals were consistent with an equilenin based ring structure substituted at one of the aromatic protons. The four aromatic $^1$H-NMR signals showed a strong singlet and a strong doublet, and a second singlet and doublet, which are weakly split into doublets.

Substitution at each of the possible aromatic positions would create a distinct splitting pattern. Substitution at the 1-position would create a single pair of strong doublets (H6 and H7) with a strong COSY correlation and a pair of singlets (H4 and H2) which would exhibit a weak COSY correlation and be weakly split by each other. Substitution at the 2-position would create but a single pair of strong doublets (H6 and H7) with a strong COSY correlation and a pair of singlets (H4 and H1). Substitution of the aromatic ring system at the 4-position would create a pattern of 2 strong pairs of doublets with strong COSY correlations in the spectrum. Substitution at the 6- or 7- position would create but a single pair of strong doublets (H1 and H2) with a strong COSY correlation and a pair of singlets (H4 and H6 or H7). The H4 proton would be expected to interact weakly with the H2 proton exhibiting a weak COSY correlation and causing the H2 doublet and the H4 singlet to be weakly split by each other.

Figure 32:
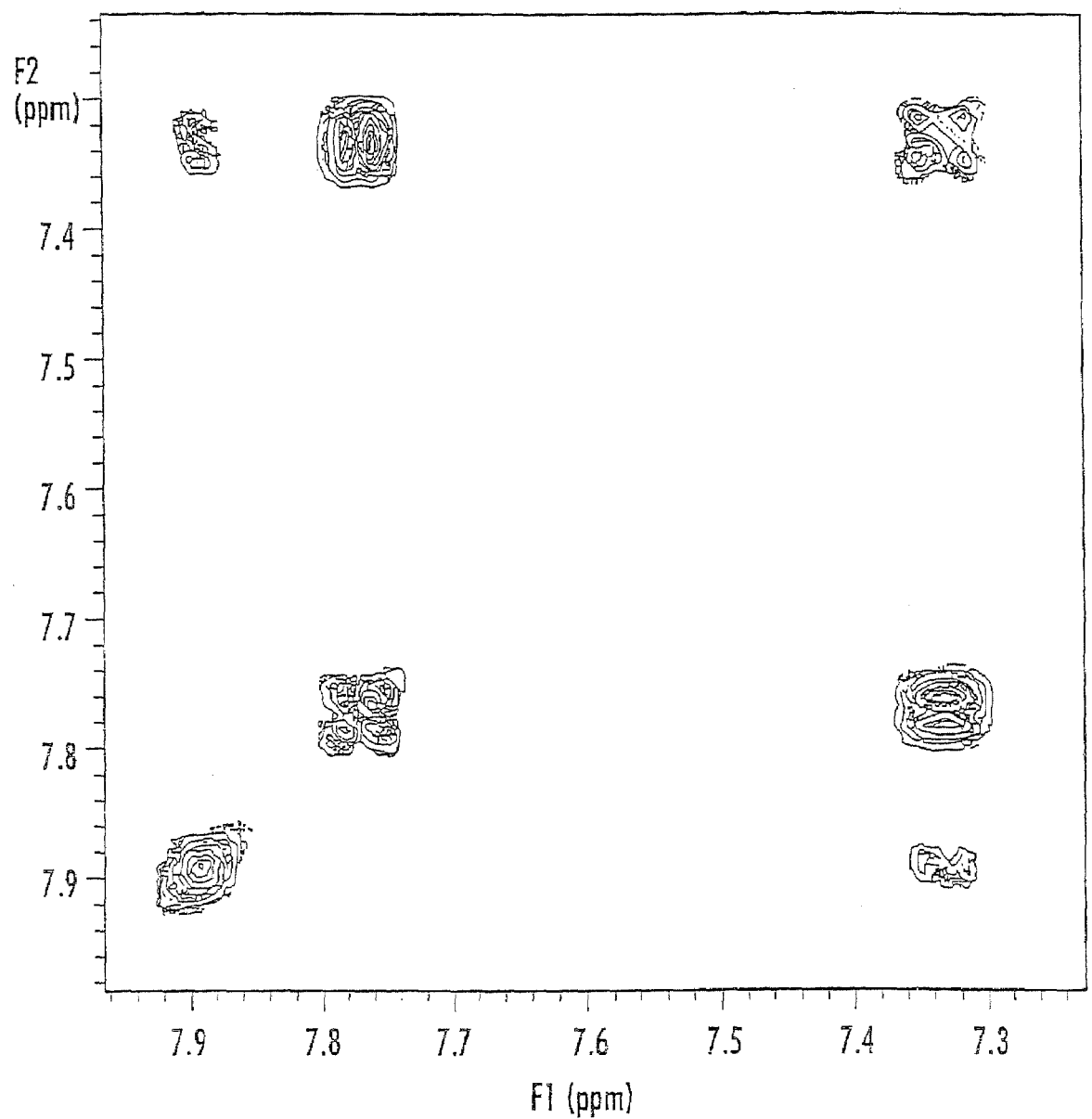
FIG. 32 is a 400 MHz 2D COSY $^1$H-NMR spectrum of the aromatic region of Peak B in $d_6$-DMSO.
Figure 33:
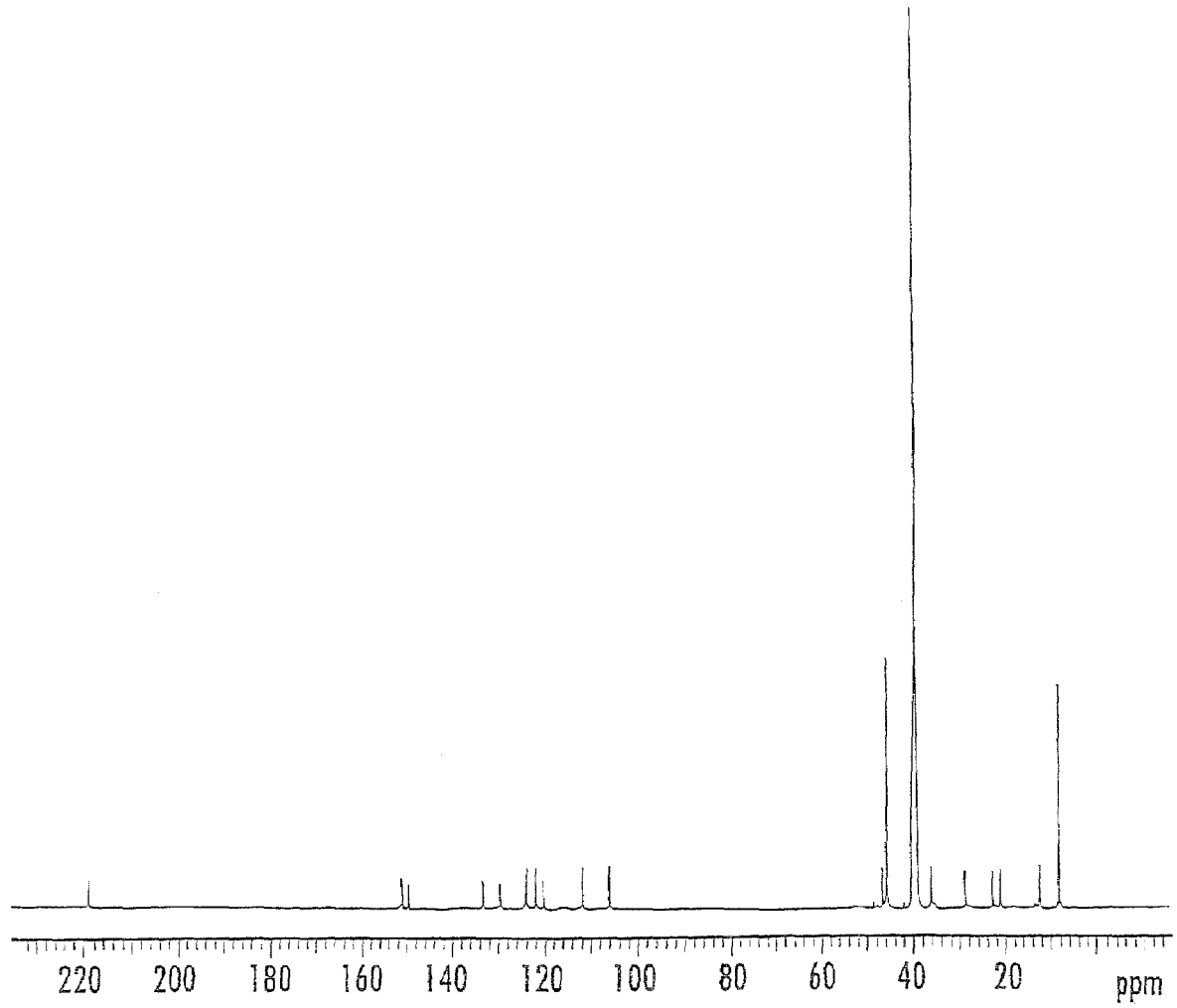
FIG. 33 is a full range 100 MHz $^{13}$C-NMR spectrum of Peak B in $d_6$-DMSO.
Figure 34:
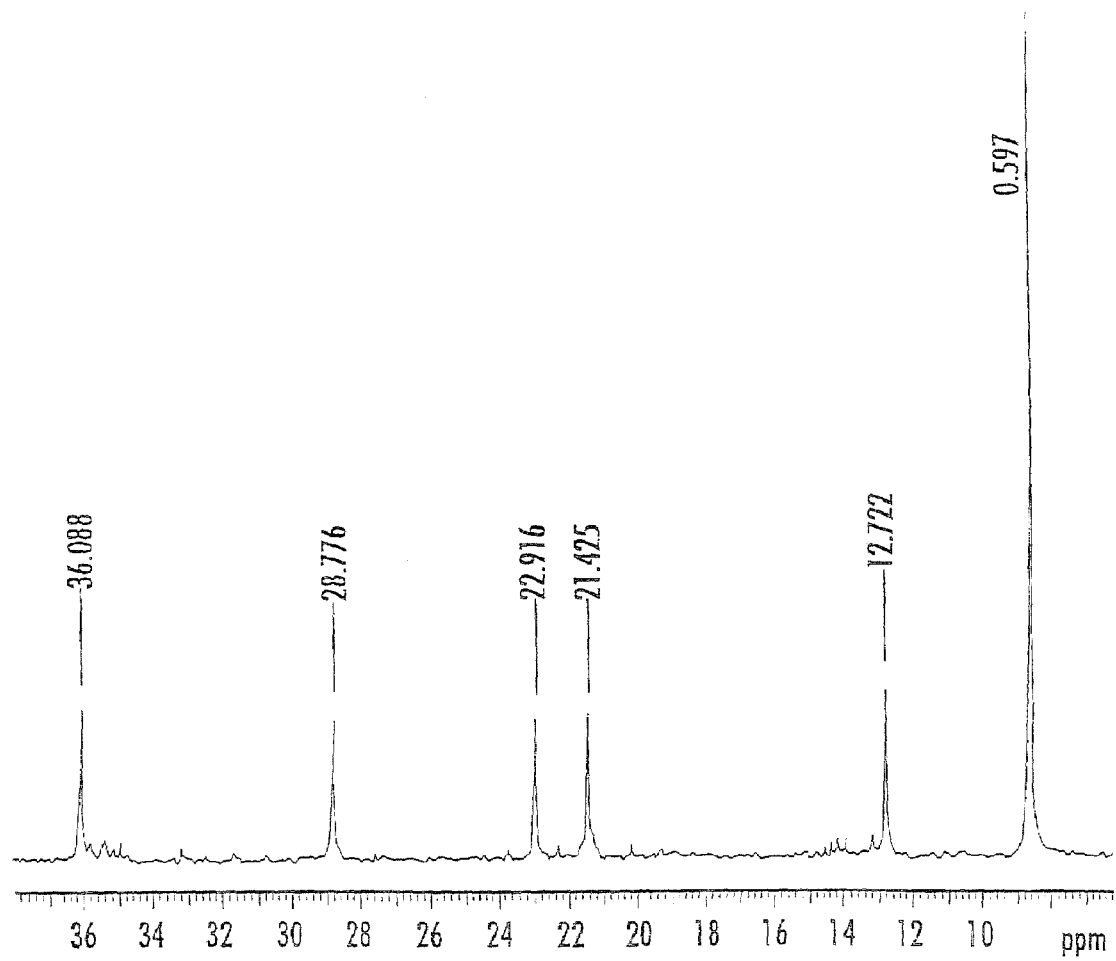
FIG. 34 is a 100 MHz $^{13}$C-NMR spectrum of the aliphatic region (0-38 ppm) of Peak B in $d_6$-DMSO.
Figure 35:
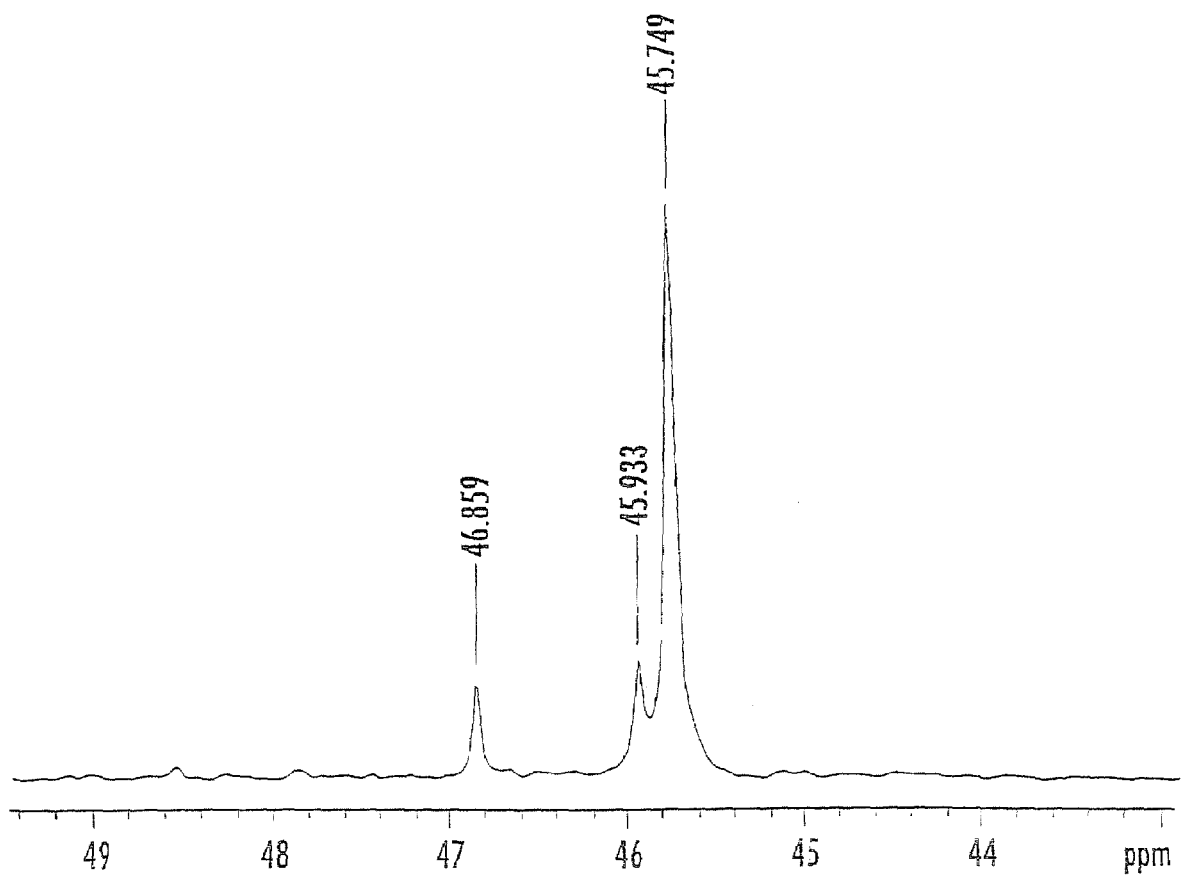
FIG. 35 is a 100 MHz $^{13}$C-NMR spectrum of the aliphatic region (43-50 ppm) of Peak B in $d_6$-DMSO.
Figure 36:
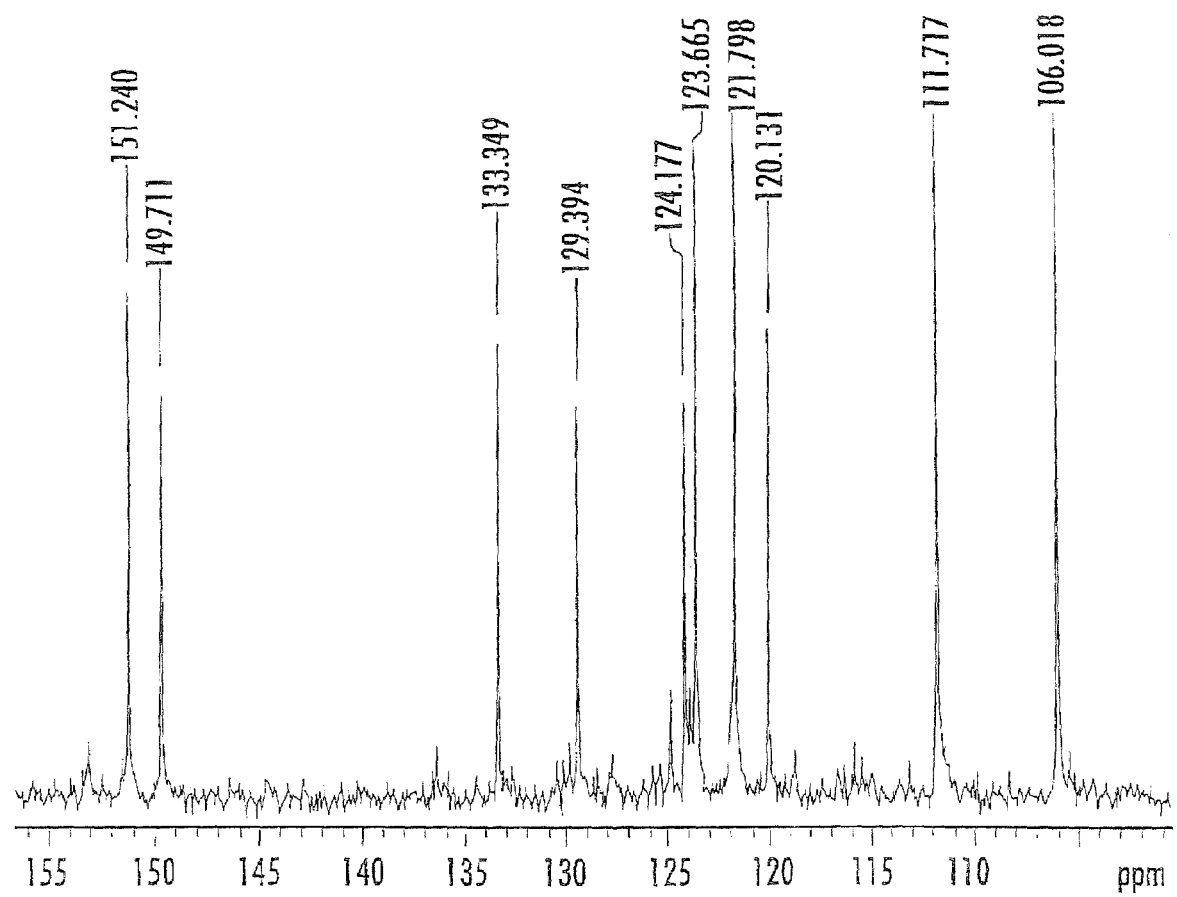
FIG. 36 is a 100 MHz $^{13}$C-NMR spectrum of the aromatic region of Peak B in $d_6$-DMSO.
Figure 41:
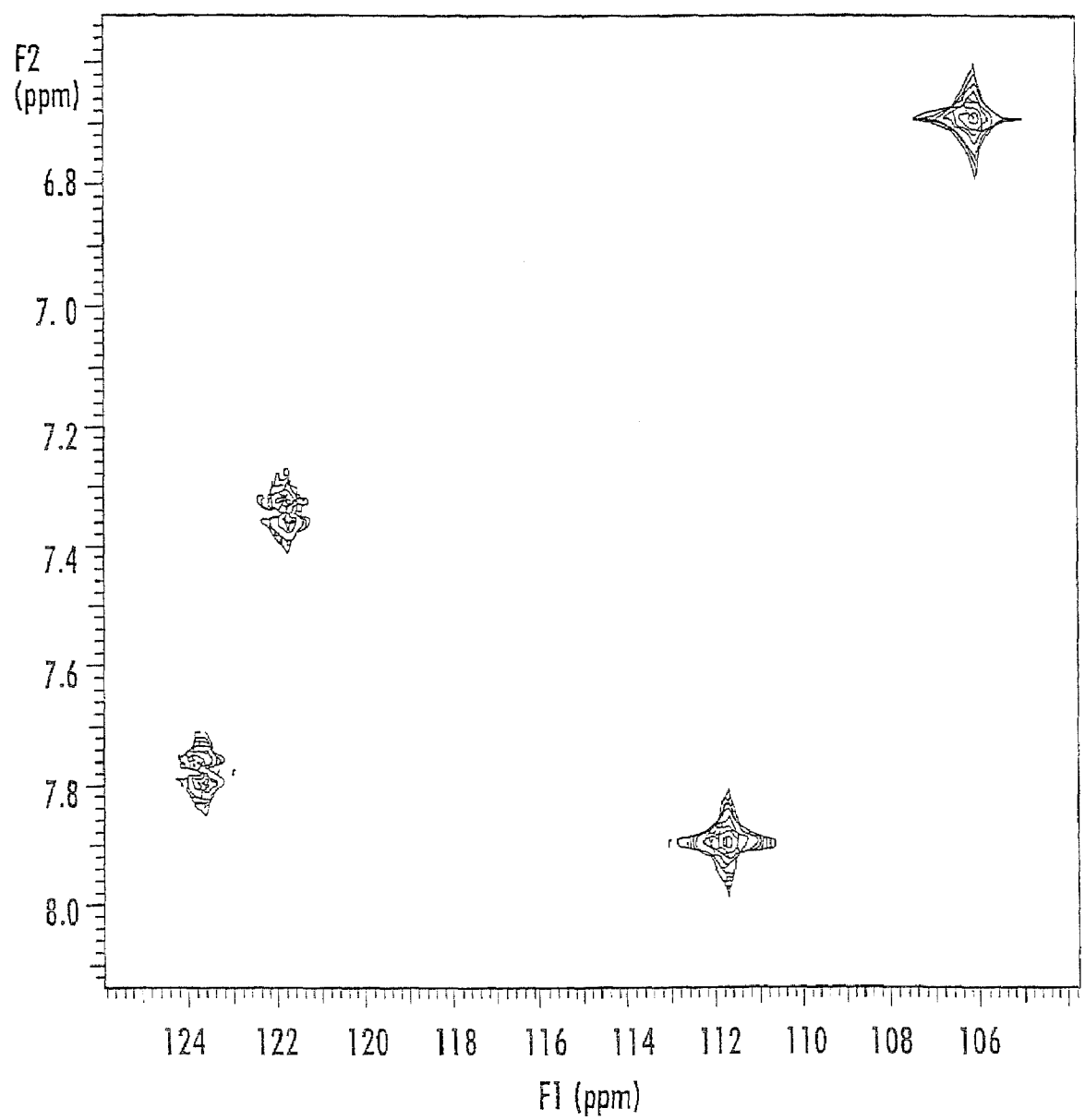
FIG. 41 is a 2D HMQC spectrum of the correlations of the aromatic protons and carbons in Peak B in $d_6$-DMSO.
Figure 42:
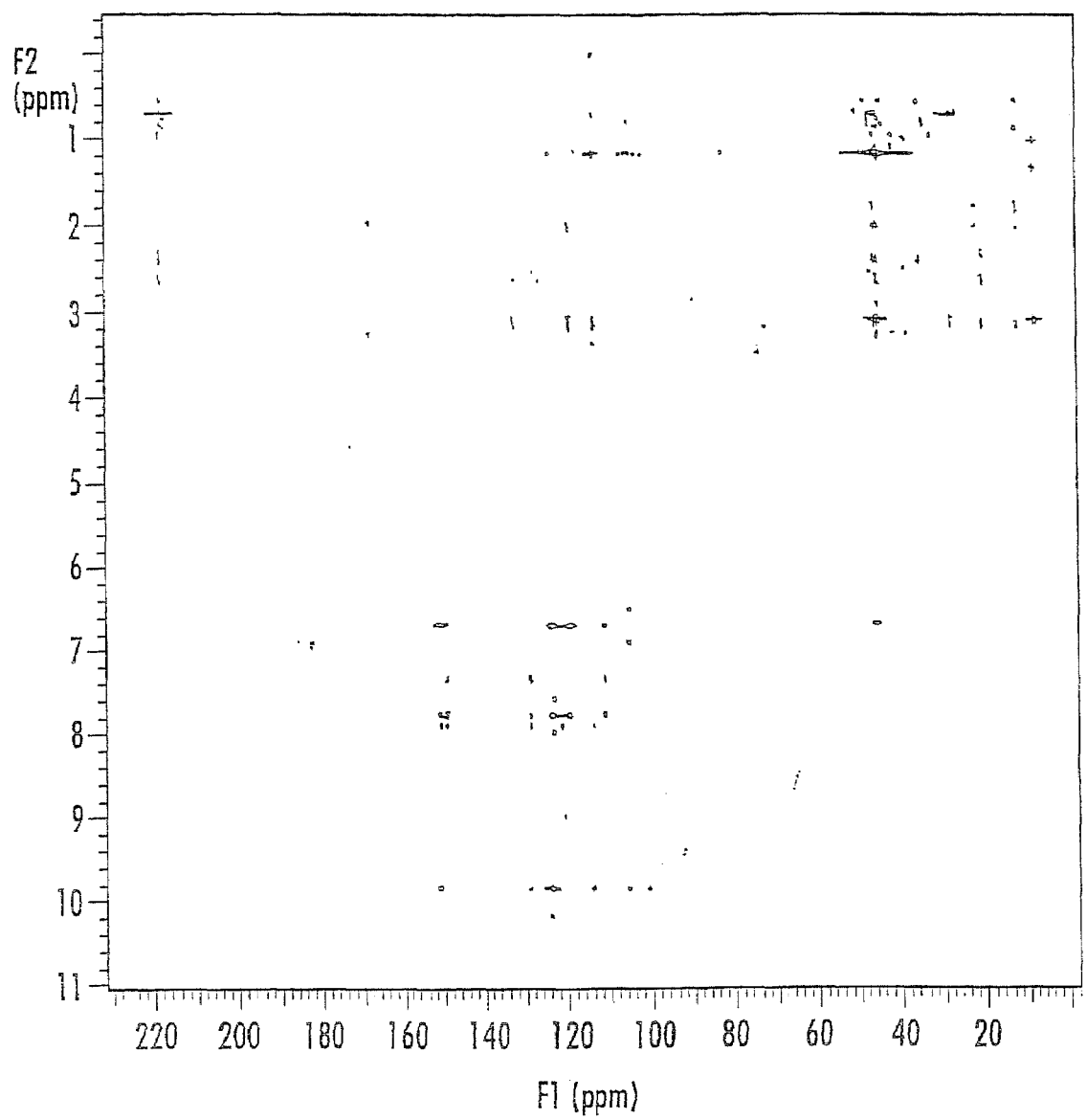
FIG. 42 is a full range 2D HMBC spectrum of the correlations of the protons and carbons in Peak B in $d_6$-DMSO.

Based upon the splitting pattern of the aromatic protons, substitution of the hydroxyl group in Peak B must be at either the H6 or H7 position. The pair of doublets at 7.77 and 7.33 ppm for H1 and H2, respectively, is shown to be adjacent from the 2D COSY spectrum (FIG. 32). H2 and H4 at 7.89 ppm exhibited a weak COSY correlation that caused H2 to appear as a doublet of doublets due to splitting by both H1 and H4; and H4 as a strong singlet weakly split to a doublet. The assignments of the corresponding carbons C1, C2, and C4 were based upon the HMQC spectra (FIG. 41) at 123.7, 121.8, and 111.7 ppm, respectively. The other aromatic ring contains only one proton at 6.69 ppm for H6 or H7, which was observed as a singlet as expected since no other protons are nearby to cause splitting. The corresponding carbon signal was assigned from the HMQC correlations at 106.0 ppm (FIG. 41).

In the $^{13}$C-NMR aromatic region (100-170 ppm) (FIG. 36), there were four large signals and six smaller signals. Protonated carbons typically have larger signals than non-protonated carbons and that was used in differentiating among the aromatic carbon atoms. This was verified by observation of only four HMQC signals in this region, which occur only for carbons with directly attached protons, in the aromatic region (FIG. 41). The remaining six aromatic carbon signals did not have HMQC peaks, and are therefore, non-protonated.

Figure 46:
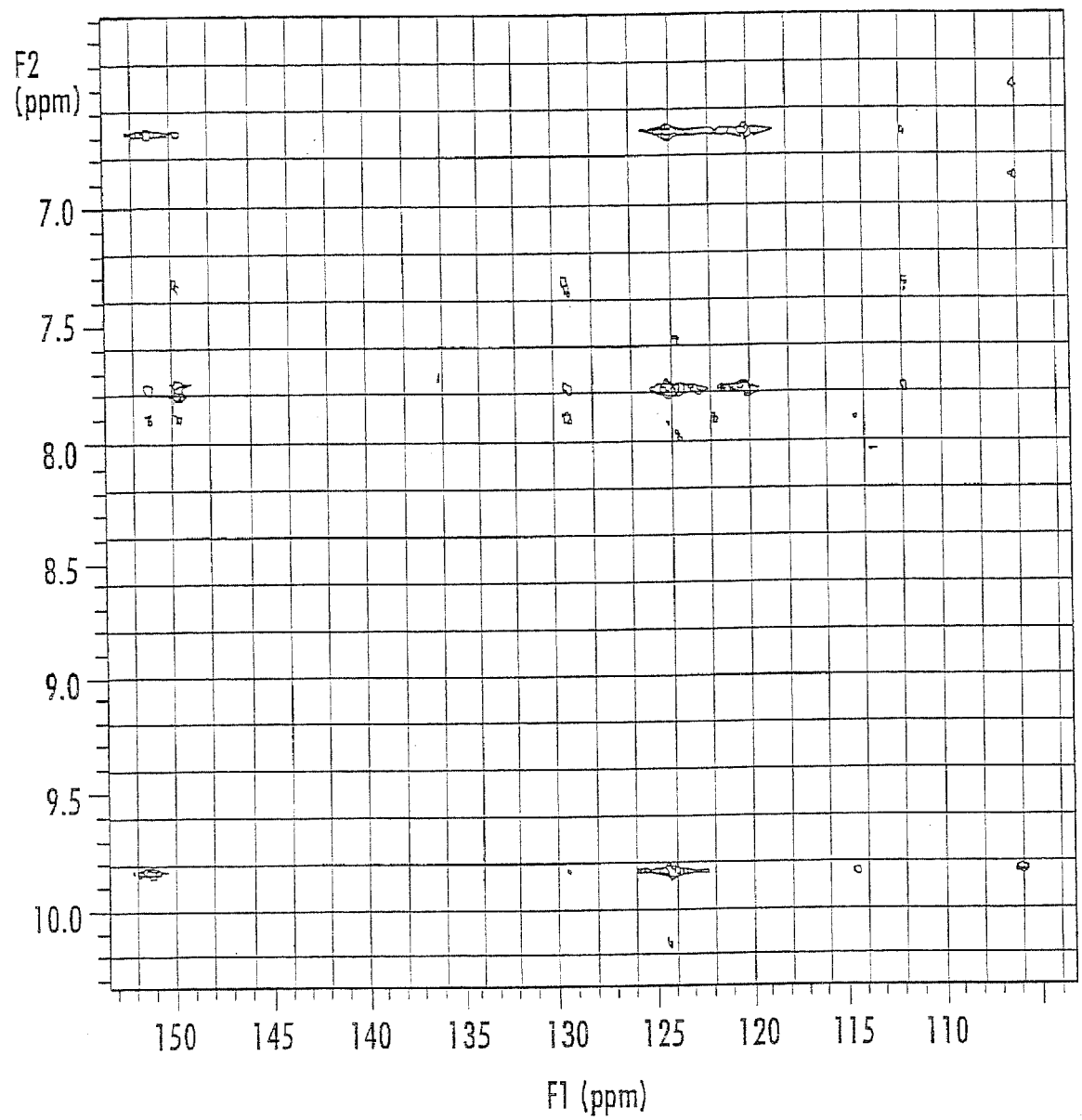
FIG. 46 is a 2D HMBC spectrum of the correlations of the aromatic protons and carbons in Peak B in $d_6$-DMSO.
Figure 47:
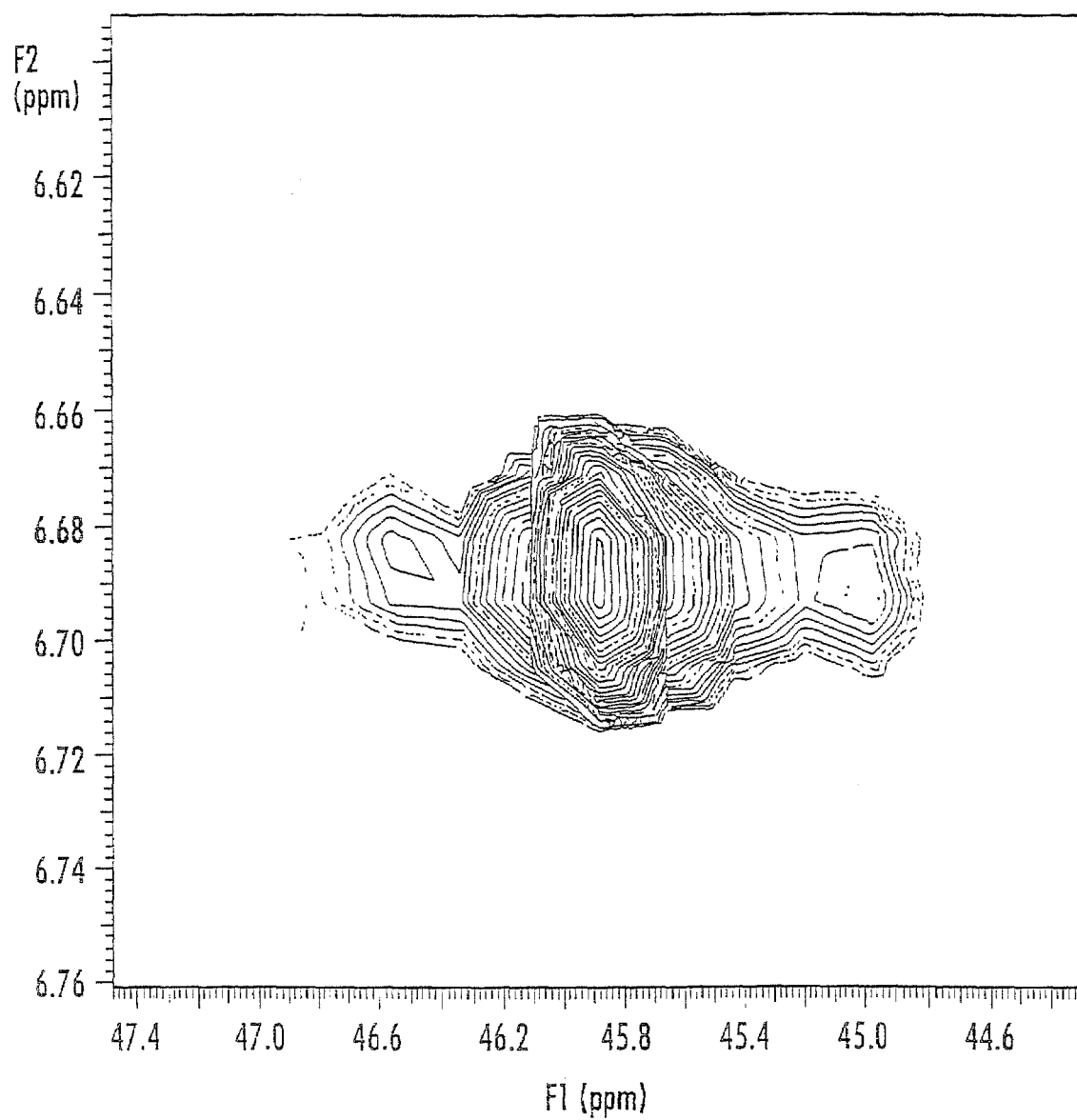
FIG. 47 is a 2D HMBC spectrum of the correlations of the aromatic protons and aliphatic carbons in Peak A in $d_6$-DMSO.

Two of the six non-protonated signals are shifted downfield to about 150 ppm (149.7 and 151.2 ppm), which is typical of aromatic carbon atoms attached to an oxygen atom. This fits the proposed structure with the normal 3-position hydroxy sulfate ester and the proposed hydroxyl substitution on an aromatic position. The HMBC spectrum (FIG. 46) shows strong correlations of the carbon signals at 149.7 ppm to H1 and H4 and the carbon signal at 151.2 ppm to H4 and either H6 or H7. Based upon those correlations the signal at 149.7 ppm must be C3. The signal at 151.2 ppm must be C6 or the H4 correlation would have been a weak 4-bond correlation. Thus, the substitution is at the 6-position and the aromatic proton at 6.69 ppm and the aromatic carbon at 106.0 ppm are assigned H7 and C7, respectively. The remaining four non-protonated carbon atoms (120.1, 124.2, 129.4, and 133.3 ppm) match the number of bridging non-protonated carbon atoms expected for the proposed structure. Assignment of these four signals can be made from HMBC correlations (FIG. 46). H2 showed correlations to the carbon signals at 111.7 (C4), 129.4, and 149.7 (C3) ppm. C10 was the only bridging carbon atom within 3 bonds of H2 and was assigned to the carbon signal at 129.4 ppm. H1 exhibits correlations at 111.7 (C4), 120.1, 124.2, 129.4 (C10), 149.7 (C3), and 151.2 (C6) ppm. H4 exhibits HMBC correlations to 121.8 (02), 129.4 (C10), 149.7 (C3), and 151.2 (C6) ppm. H7 exhibits HMBC correlations to aromatic signals at 111.7 (C4), 120.1, 124.2, and 151.2 (C6) ppm. Based upon these correlations, the carbon signals at 120.1 and 124.2 ppm must correspond to C5 and C9, but their exact assignments are not yet established.

Figure 29:
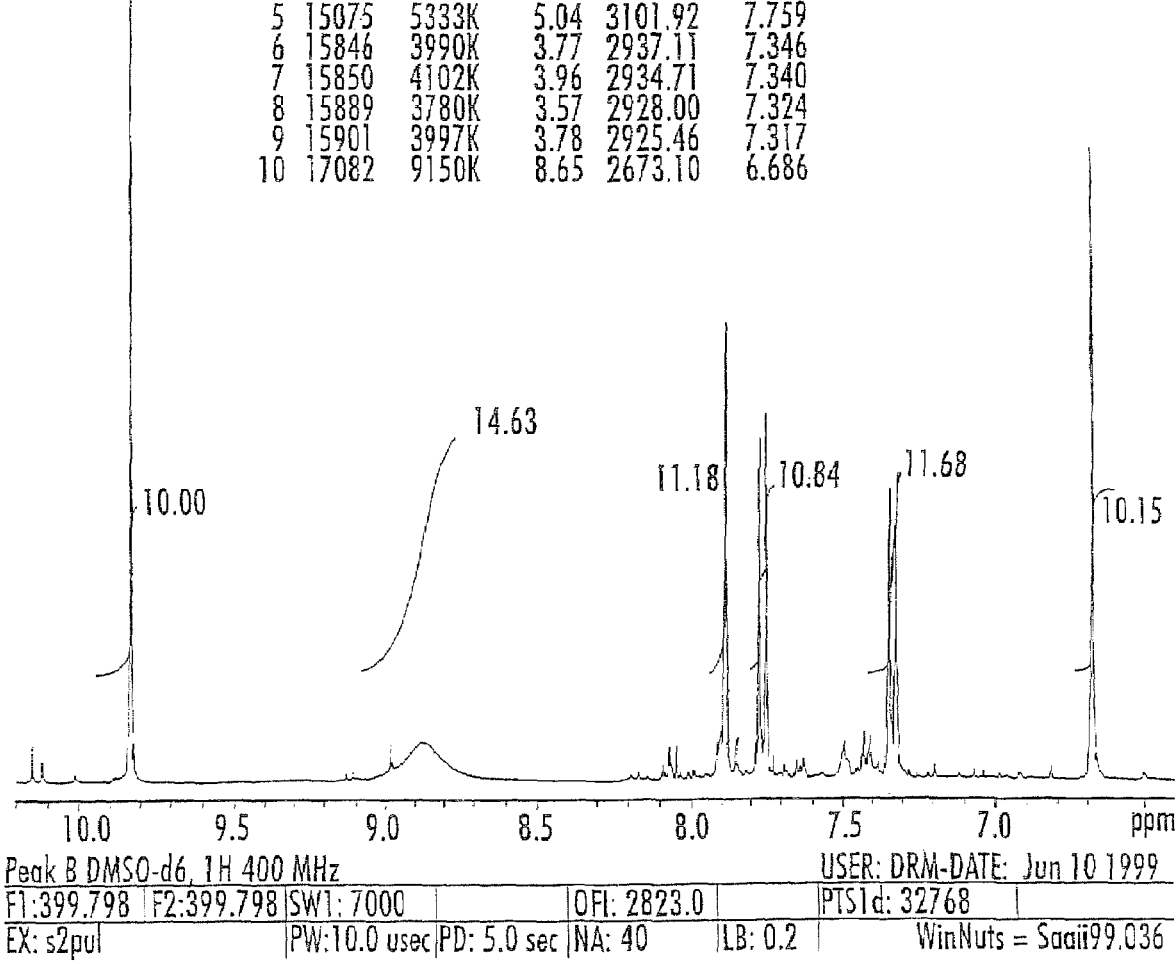
FIG. 29 is a 400 MHz $^1$H-NMR spectrum of the aromatic region of Peak B in $d_6$-DMSO.
Figure 30:
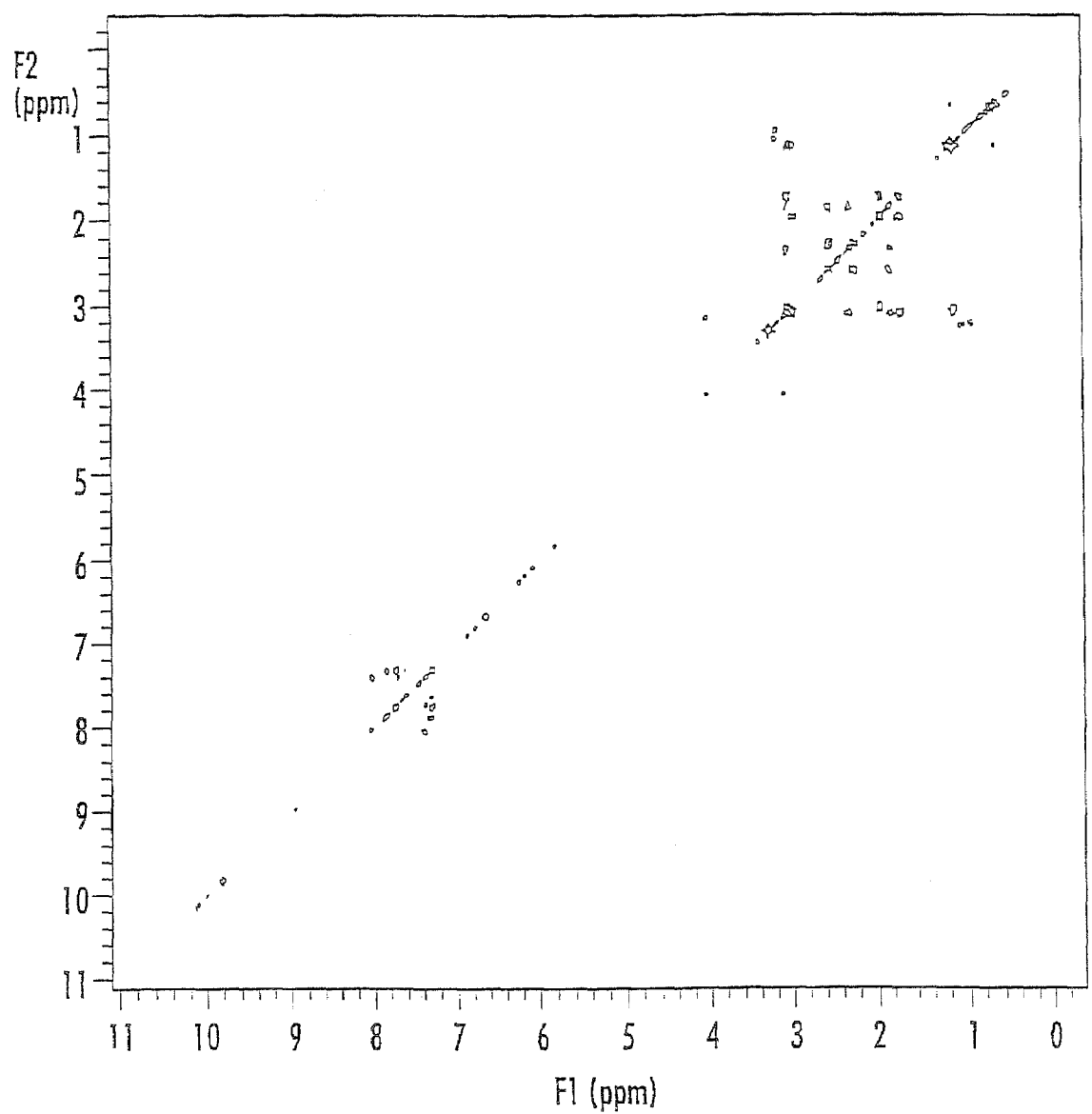
FIG. 30 is a full range 400 MHz 2D COSY $^1$H-NMR spectrum of Peak B in $d_6$-DMSO.

There is a single strong signal downfield in the $^1$H-NMR spectrum at 9.83 ppm (FIG. 29). This region is typical of aromatic phenolic protons and this signal is assigned as H6(OH). HMBC spectrum for this proton exhibits correlations at 106.0 (C7), 124.2, 129.4 (C10), and 151.2 (C6) ppm (FIG. 46). Based upon these correlations and the relationships of the other protons the signal at 124.2 ppm must be C5 and thus the signal at 120.1 ppm must be C9. This leaves only the aromatic carbon signal at 133.3 ppm unassigned. Thus, the remaining aromatic signal by process of elimination was assigned as C8.

Figure 31:
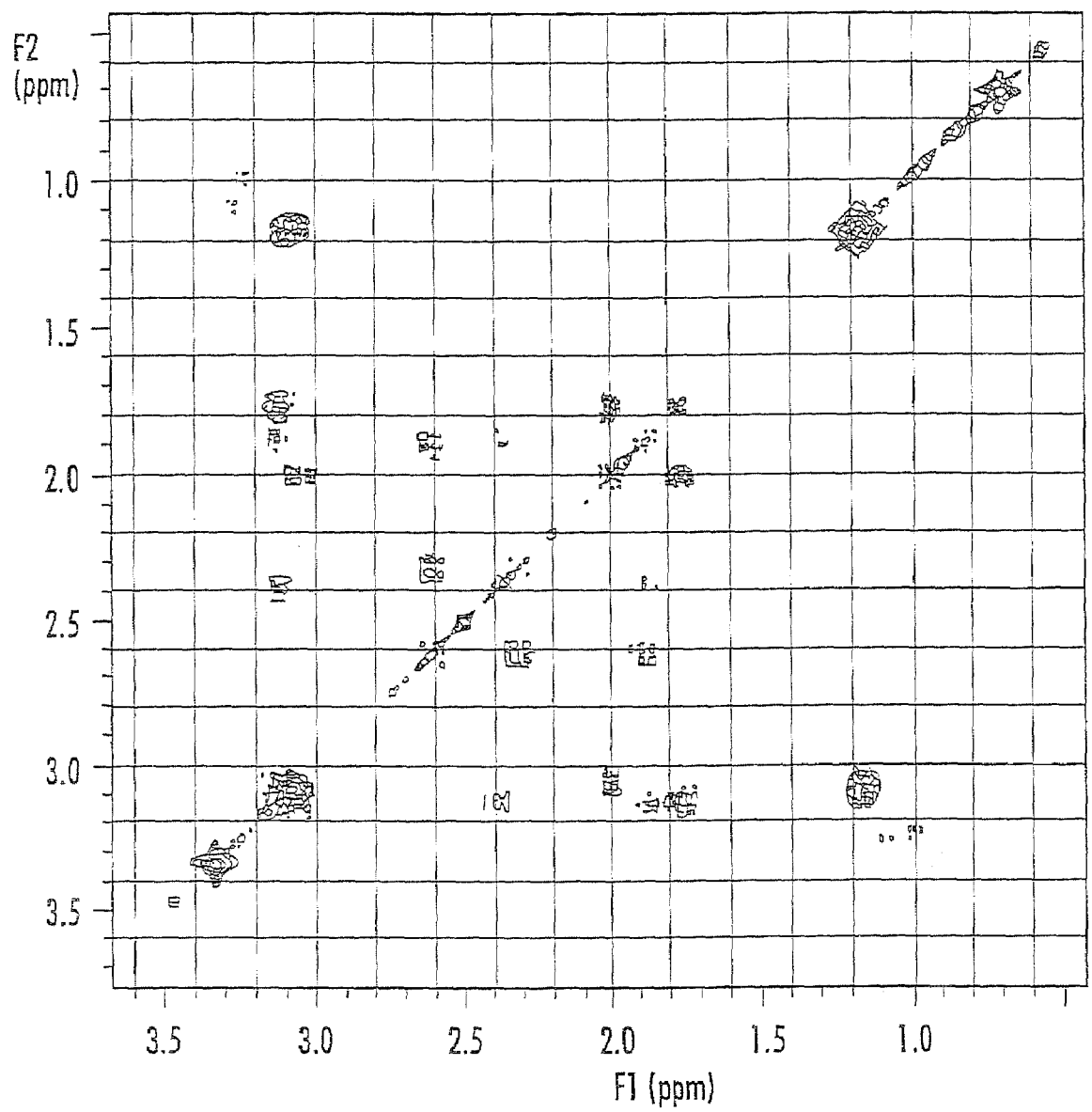
FIG. 31 is a 400 MHz 2D COSY $^1$H-NMR spectrum of the aliphatic region of Peak B in $d_6$-DMSO.

The methyl region (0.5 to 1.5 ppm) of the $^1$H-NMR spectrum (FIG. 28) shows a strong methyl signal split into a triplet at 1.17 ppm that is indicative of the methyl proton (H20) of the triethyl ammonium cation. This signal shows a strong COSY correlation to the quartet signal at 3.10 ppm for the protons (H119) of the methylene group (FIG. 31). The HMQC correlation spectrum (FIG. 39) showed corresponding carbon atoms at 8.6 and 45.7 ppm for C20 and C19, respectively. The amine proton (NH$^+$) of the cation was expected to have a $^1$H-NMR chemical shift of about 8.0 to 9.5 ppm; however, amines have the problem of slow exchange and often are not seen, or are only seen as a small broad peak in this region. The NH proton in the $^1$H-NMR spectrum was observed as a single broad signal at about 8.88 ppm for this compound (FIG. 29).

Figure 37:
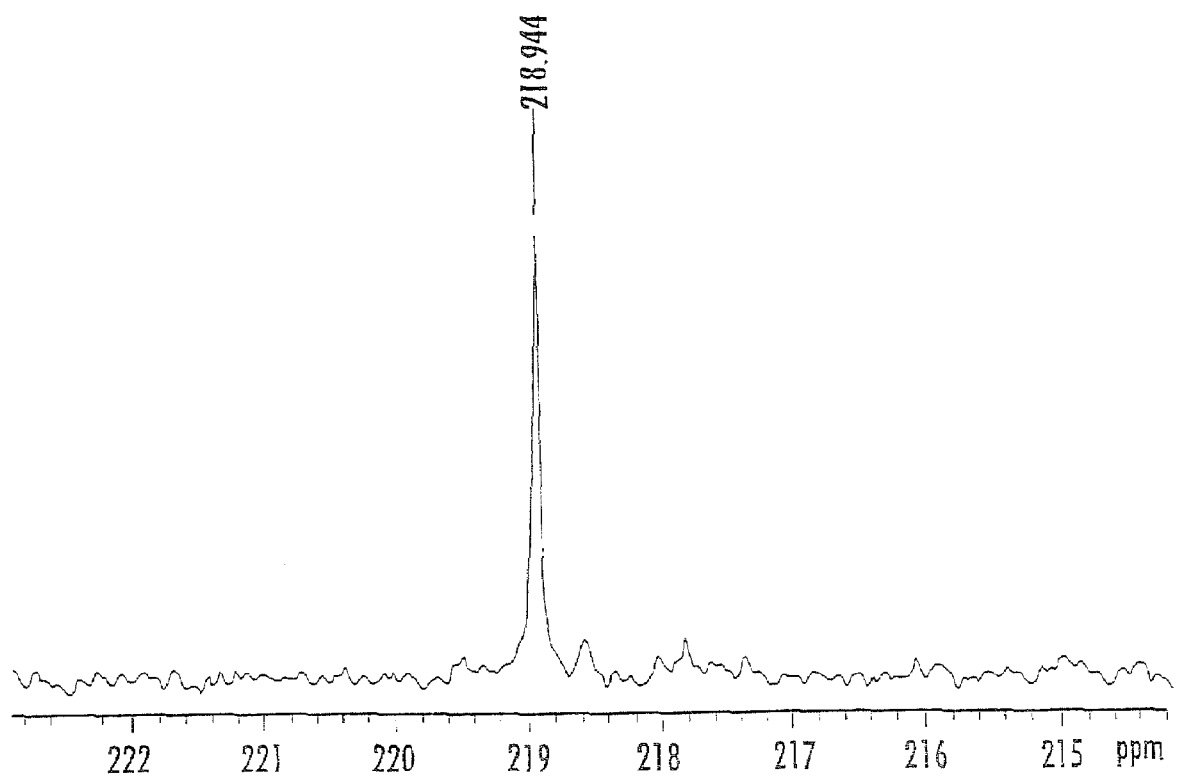
FIG. 37 is a 100 MHz $^{13}$C-NMR spectrum of the carbonyl region of Peak B in $d_6$-DMSO.
Figure 38:
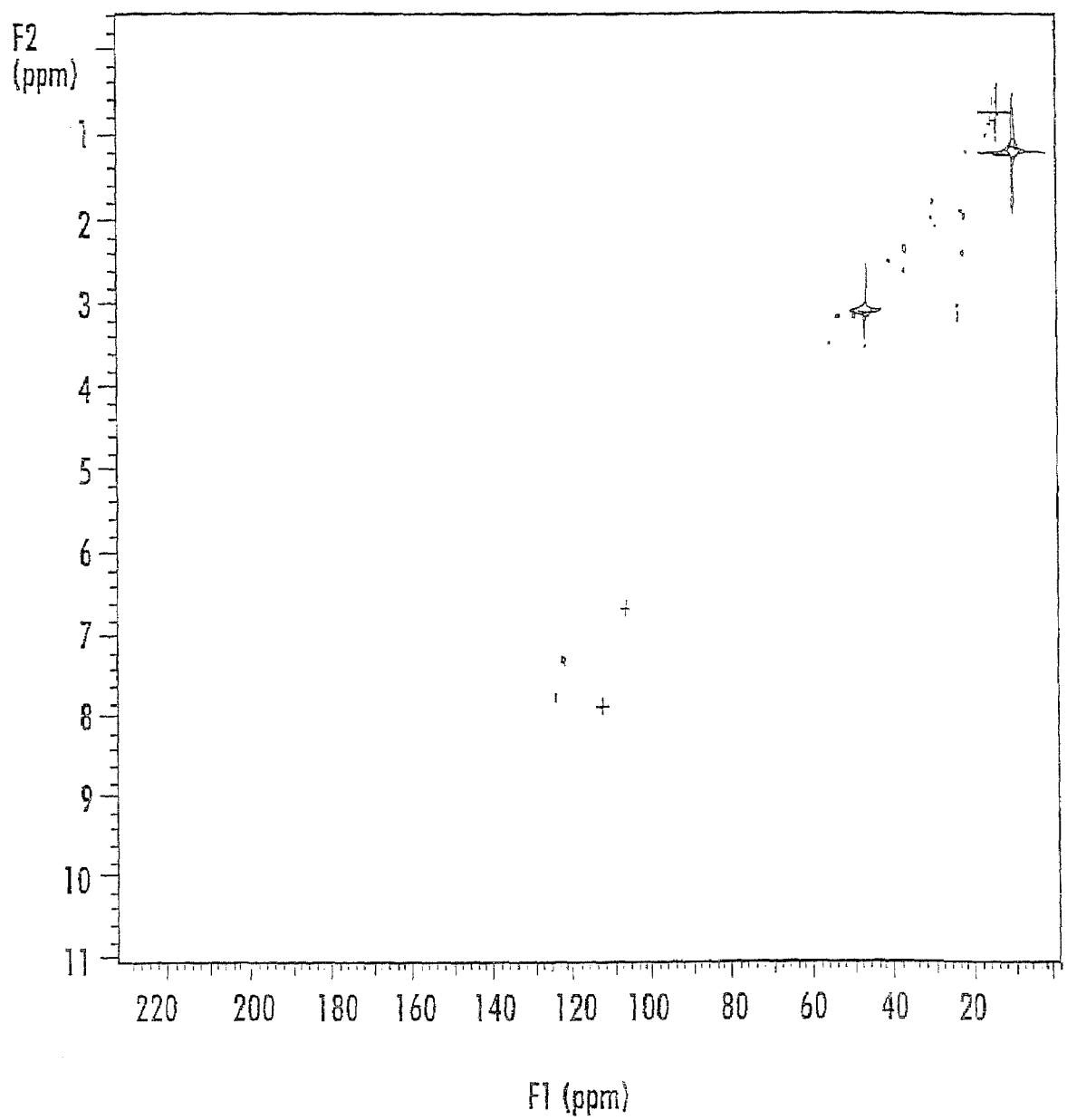
FIG. 38 is a full range 2D HMQC spectrum of the correlations of the protons and carbons of Peak B in $d_6$-DMSO.
Figure 39:
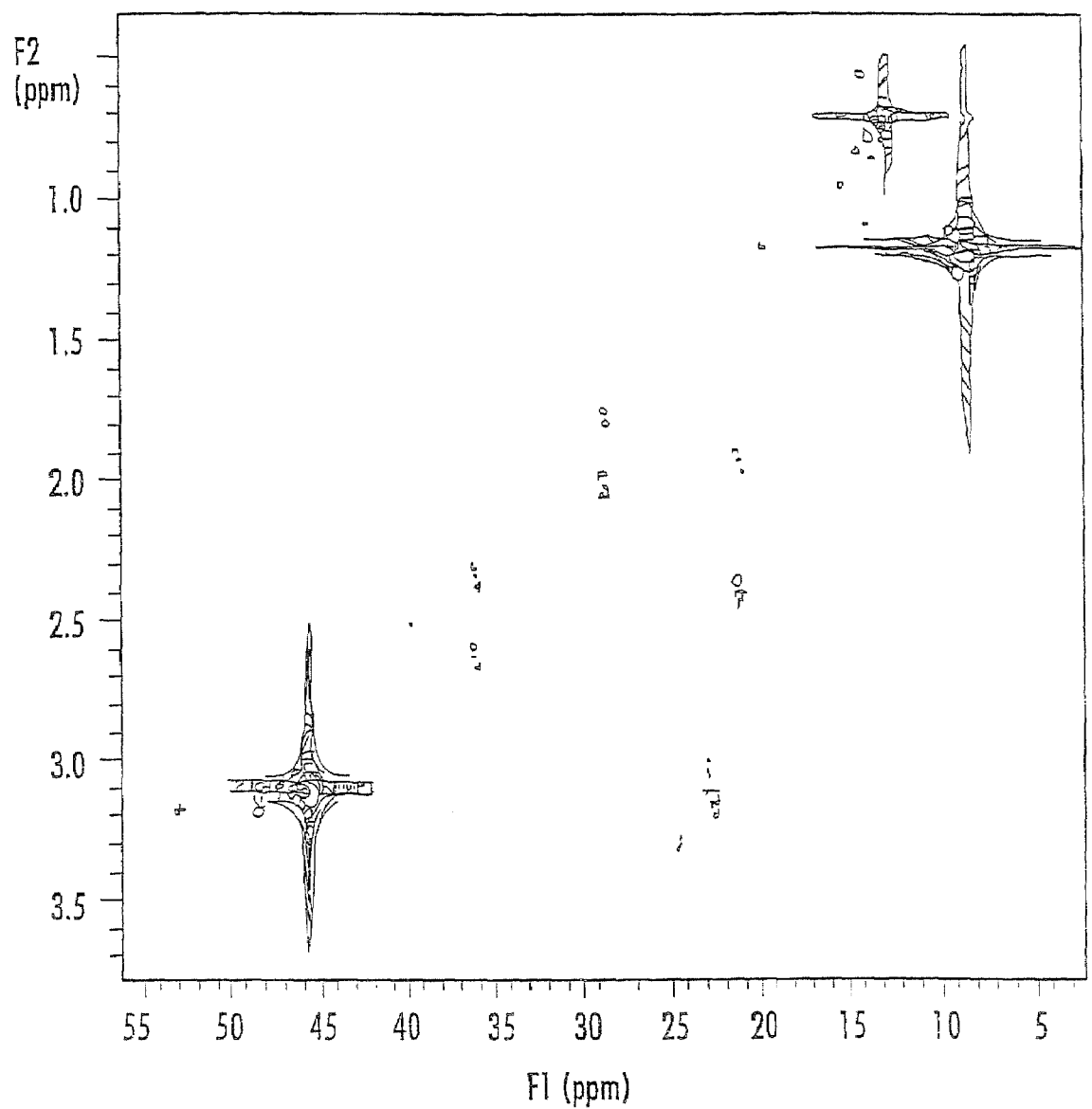
FIG. 39 is a 2D HMQC spectrum of the correlations of the aliphatic protons and carbons in Peak B in $d_6$-DMSO.
Figure 40:
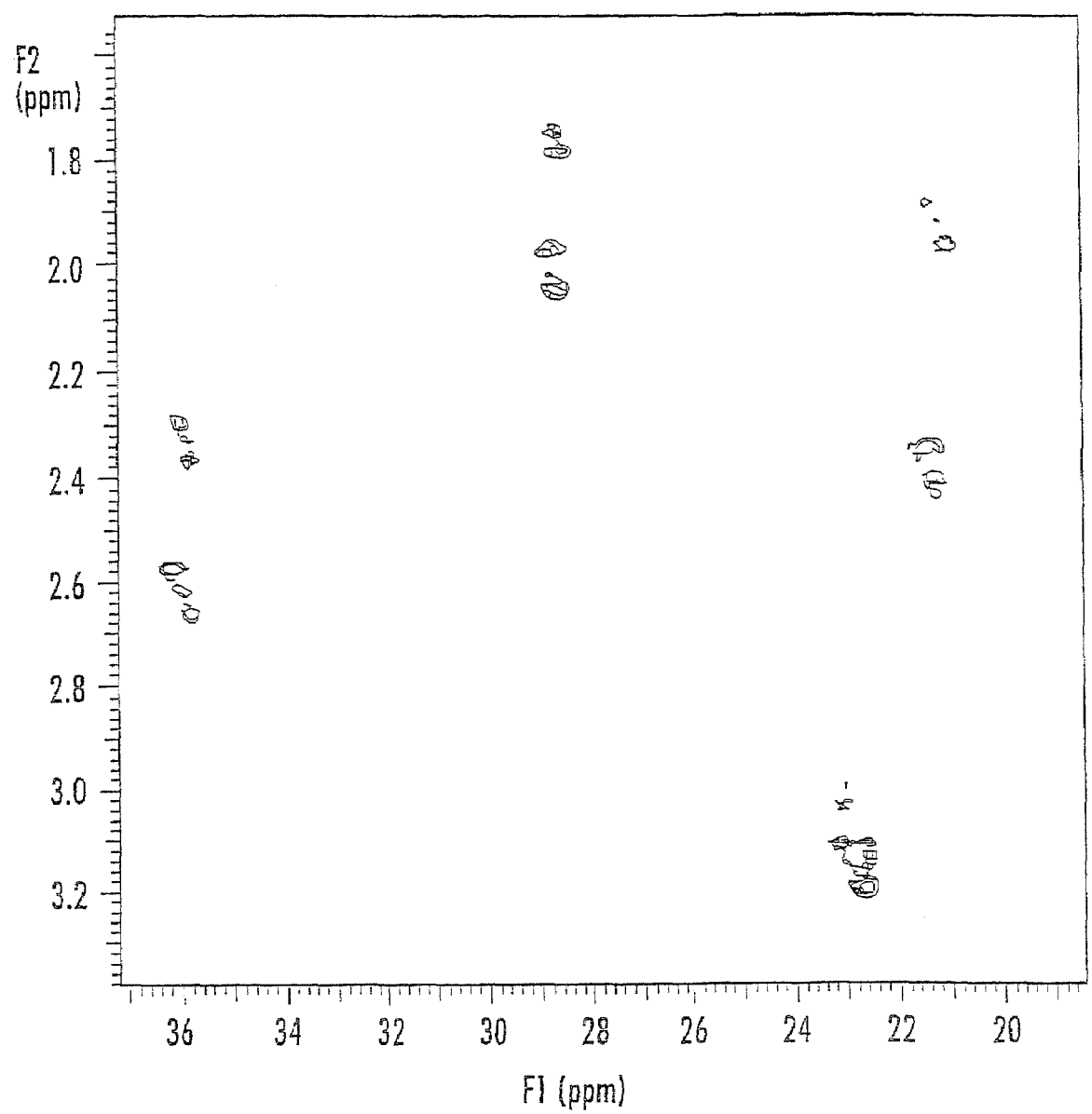
FIG. 40 is a 2D HMQC spectrum of the correlations of the aliphatic protons and carbons (Zoom in of FIG. 39) in Peak B in $d_6$-DMSO.

In the $^{13}$C-NMR aliphatic region (0-100 ppm) (FIGS. 34-35), there were two strong signals at 8.6 and 45.7 ppm for the triethyl ammonium cation, and seven signals for the aliphatic carbons of Peak B. The proposed structure for Peak B contains seven aliphatic carbon atoms and a ketone carbon. The seven aliphatic carbon signals were observed at 12.7, 21.4, 22.9, 28.8, 36.1, 45.9, and 46.9 ppm. Carbonyl carbon atoms are known to shift far downfield to above 200 ppm. FIG. 37 showed such a signal present at 218.9 ppm and was assigned C17. Six of the seven signals show HMQC correlations to proton signals (FIGS. 39-40). Only the carbon signal at 46.9 ppm did not exhibit a correlation to any proton signal and was considered a bridging carbon. The proposed structure has one bridging aliphatic carbon atom, and thus the peak at 46.9 ppm was assigned as C13. The carbon signals at 12.7 and 45.9 ppm each correlated to a single proton signal, whereas the other four carbon signals observed at 21.4, 22.9, 28.8, and 36.1 ppm each correlated to two proton signals. This is often the case in saturated aliphatic ring systems since the two protons of the methylene groups are present in differing electronic environments and thus, exhibit different chemical shifts.

Inspection of the two carbon signals with a single proton HMQC correlation shows that the signal at 12.7 ppm is in the expected methyl region for $^{13}$C-NMR and correlates by HMQC to the proton signal at 0.70 ppm. These protons at 0.70 ppm exhibited the expected integration ratio for a methyl group of 3:1 relative to the individual aromatic protons and are assigned as H18 based on the chemical shift and the HMQC correlations and is the only methyl group in the proposed structure for Peak B. The remaining carbon atom with one proton was observed at 45.9 ppm was assigned as C14. The proton signal at 3.14 ppm correlated to it by HMQC and was assigned H14.

The remaining four aliphatic carbon signals each exhibited two HMQC correlations to proton signals. The carbon signal at 22.9 ppm correlates to the protons at 3.08 and 3.12 ppm. The COSY spectrum of these two protons show that they couple to the proton signals at 1.78 and 2.00 ppm indicating the two sets are adjacent. The HMQC spectrum shows these protons both correlate to the carbon signal at 28.8 ppm. The carbon signal at 21.4 ppm correlates to the protons at 1.88 and 2.39 ppm. The COSY spectrum of these two protons show that they couple to the proton signals at 2.32 and 2.62 ppm, indicating the two sets are adjacent. The HMQC spectrum shows these protons both correlate to the carbon signal at 36.1 ppm. These observations are consistent with the proposed structure of Peak B that has two sets of adjacent methylene groups at C11 and C12, and at C15 and C16.

Figure 43:
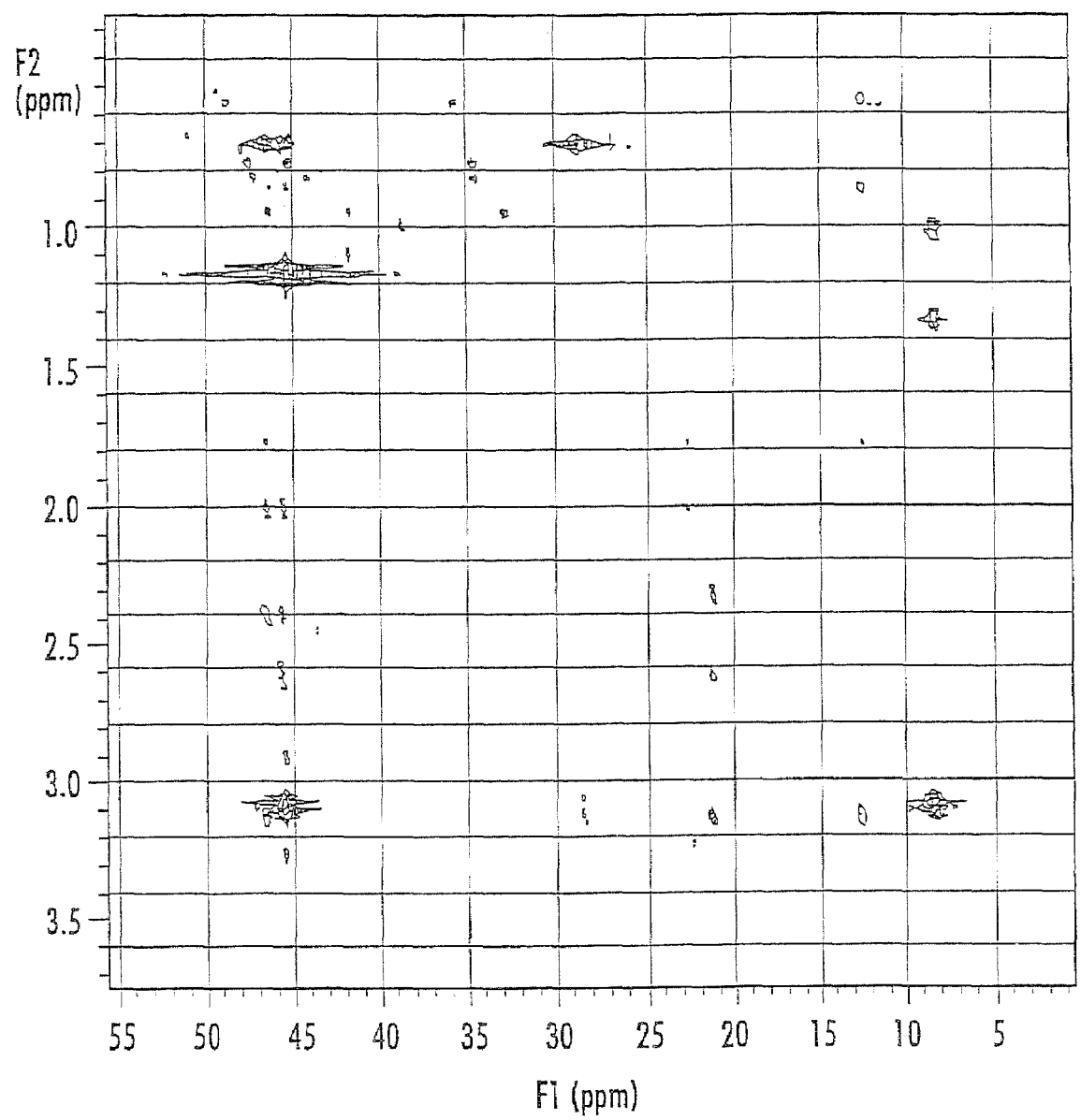
FIG. 43 is a 2D HMBC spectrum of the correlations of the aliphatic protons and carbons in Peak B in $d_6$-DMSO.
Figure 44:
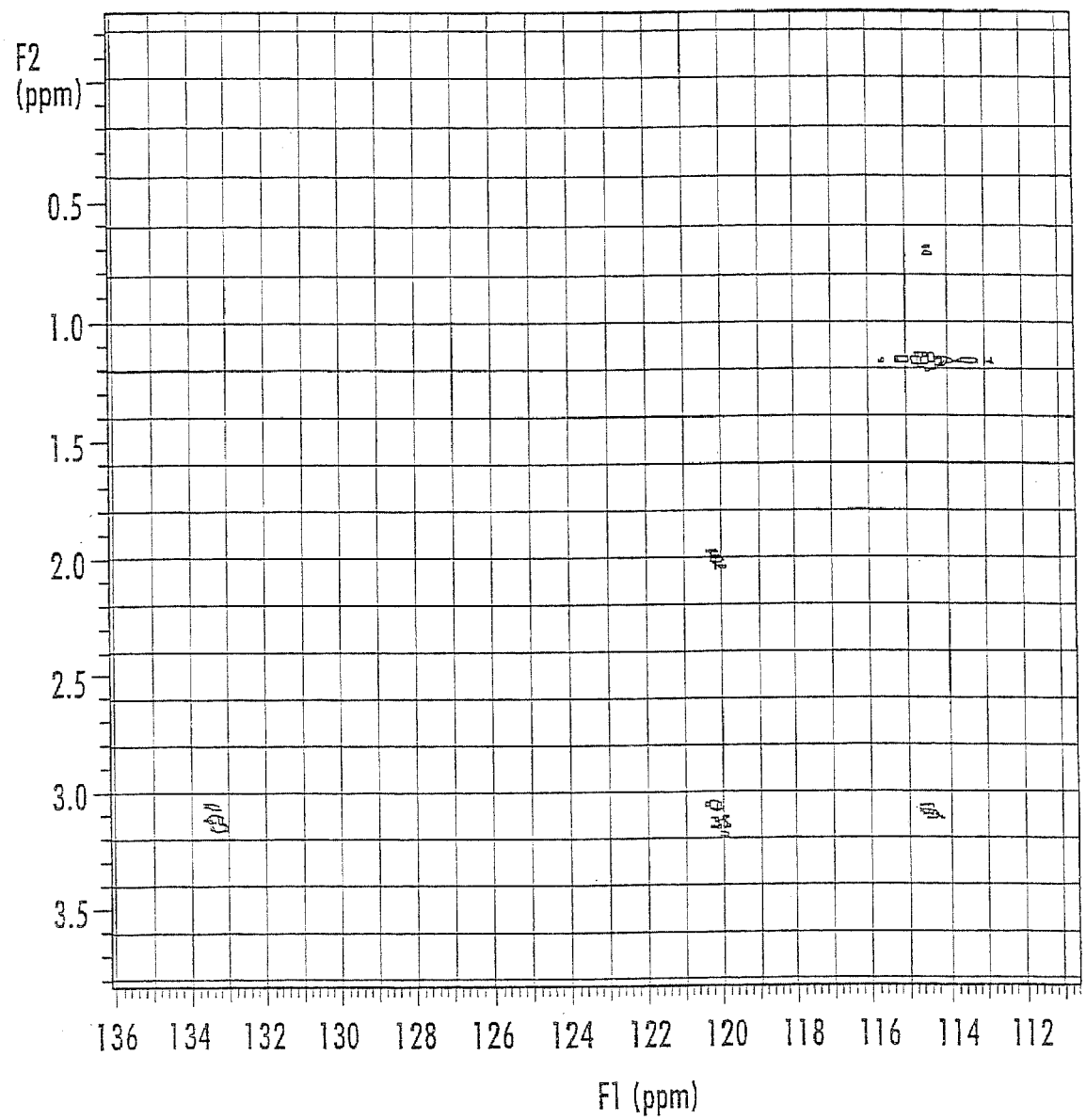
FIG. 44 is a 2D HMBC spectrum of the correlations of the aliphatic protons and aromatic carbons in Peak B in $d_6$-DMSO.
Figure 45:
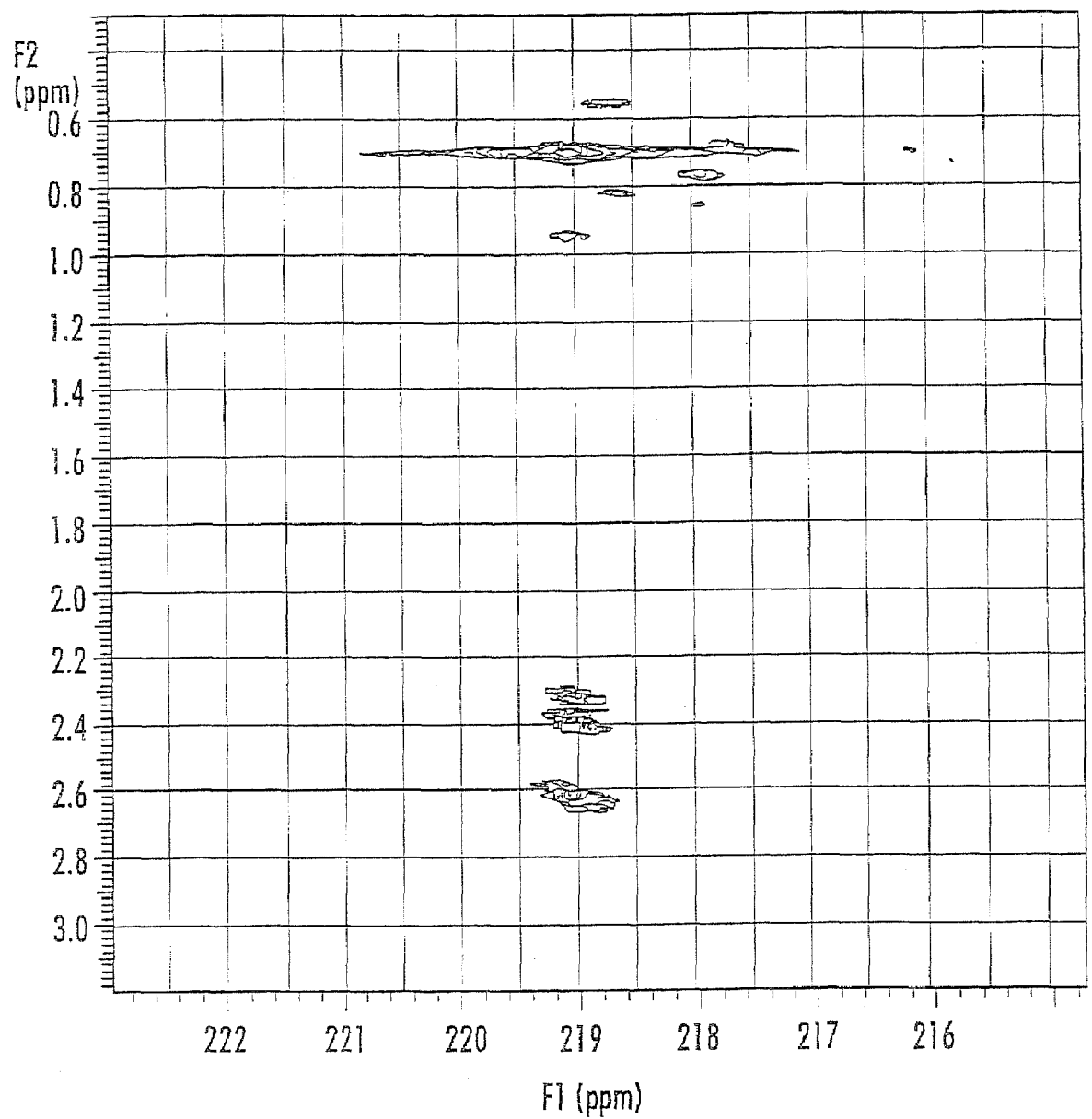
FIG. 45 is a 2D HMBC spectrum of the correlations of the aliphatic protons and carbonyl carbons in Peak B in $d_6$-DMSO.

HMBC couplings (FIGS. 43-44) can be used to ascertain the identity and position of each of the four methylene groups. The bridging carbon at 120.1 (09) ppm correlates to only the protons of the carbon signals at 22.9 and 28.8 ppm (FIG. 44). This observation verifies that the carbon signals at 22.9 and 28.8 ppm must be assigned as C11 and C12 and that the other two carbon signals at 21.4 and 36.1 ppm must be assigned as C15 and C16, but their exact assignments are not yet established. The proton at 0.70 (H18) ppm shows a HMBC correlation to the carbon signals at 28.8, 45.9 (014), 46.9 (C13), and 218.9 (C17) ppm (FIG. 43). Based upon this, the carbon signal at 28.8 ppm was assigned as C12 and thus, the carbon signal at 22.9 ppm must be C11. Based upon the HMQC correlations (FIG. 40) of each of these carbon signals, the proton signals at 3.08 and 3.12 ppm can be assigned as H11a and H11b, respectively, and the protons at 1.78 and 2.00 ppm can be assigned as H12a and H12b, respectively. The proton at 3.14(014) ppm shows COSY correlations to the protons at 1.88 and 2.39 ppm (FIG. 31). Based upon these COSY correlations of the proton signal at 2.14 ppm, it must be adjacent to H14 and thus the carbon signal at 21.4 ppm must be C15 and the carbon signal at 36.1 ppm must be C16. Based upon the HMQC correlations (FIG. 40) of each of the carbon signals, the proton signals at 1.88 and 2.39 ppm can be assigned as H15a and H15b, respectively, and the protons at 2.32 and 2.62 ppm can be assigned as H16a and H16b, respectively. Other HMBC correlations are detailed in Table 4 above and are consistent with the proposed structure of Peak B.

Additional signals in the proton NMR spectrum (FIGS. 28-29) were observed from water at 3.34 ppm, DMSO at 2.50 ppm, a small amount of methanol at 3.18 and 4.10 ppm, and other assorted small, unidentified aromatic and aliphatic "impurity" signals. In addition to the expected aromatic and aliphatic signals of Peak B (FIG. 38), methanol was observed at 48.5 ppm (HMQC peak at 3.18 ppm).

Based on the observed NMR data the structure of Peak B corresponds well to the proposed structure.

The present invention has been described herein with reference to its preferred embodiments. The embodiments do not serve to limit the invention, but are set forth for illustrative purposes. The scope of the invention is defined by the claims that follow.

What is claimed is:
1. A compound having the following structure:

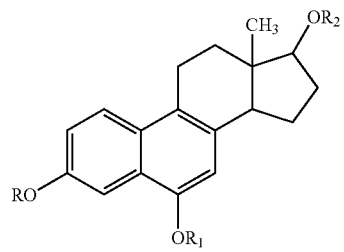

or pharmaceutically acceptable salts thereof
wherein:
R, $R_1$ and $R_2$ are each independently hydrogen, sulfate or glucuronide and said compound has the following physicochemical properties:
(a) a peak located at about 1.2 ppm in a $^1$H-NMR spectrum; and
(b) a peak located at about 45 ppm in a $^{13}$C-NMR spectrum.

2. The compound of claim 1, wherein the compound is a calcium salt thereof.

3. The compound of claim 2, wherein the calcium salt is selected from the group consisting of calcium citrate, calcium lactate, calcium fumurate, calcium acetate, calcium glycerophosphate, calcium chloride, calcium phosphate, calcium sulphate and calcium nitrate.

4. The compound of claim 1, wherein the compound is greater than about 95% pure.

5. A method of treating a subject in need of estrogen therapy, said method comprising administering an effective amount of a compound having the following structure:

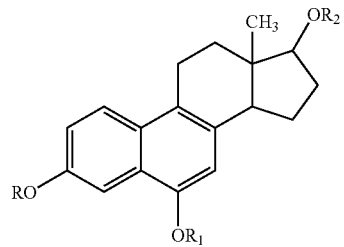

or pharmaceutically acceptable salts thereof
wherein:
R, $R_1$ and $R_2$ are each independently hydrogen, sulfate or glucuronide and said compound has the following physicochemical properties:
(a) a peak located at about 1.2 ppm in a $^1$H-NMR spectrum; and
(b) a peak located at about 45 ppm in a $^{13}$C-NMR spectrum.

6. The method of claim 5, wherein the compound or pharmaceutically acceptable salt is administered as a vaginal cream, gel, suppository or transdermal patch.

7. The method of claim 5, wherein the compound or pharmaceutically acceptable salt thereof is administered as part of a pharmaceutical composition, said composition further comprising at least one additional pharmaceutically active ingredient.

8. The method of claim 7, wherein the at least one additional pharmaceutically active ingredient is selected from the group consisting of estrogenic compounds, androgenic compounds, progestin compounds, vasodilation agents, calcium salts, and vitamin D, and mixtures and combinations thereof.

9. The method of claim 5, wherein the condition treatable by estrogen therapy is selected from the group consisting of vasomotor symptoms, atrophic vaginitis, osteoporosis, hypoestrogenism due to hypogonadism, hypoestrogenism due to castration, hypoestrogenism due to primary ovarian failure, breast cancer in selected persons with metastatic disease, advanced androgen-dependent carcinoma of the prostate, abnormal uterine bleeding, and kraurosis vulvae.

10. A topical pharmaceutical formulation comprising:
(a) a compound represented by Formula I:

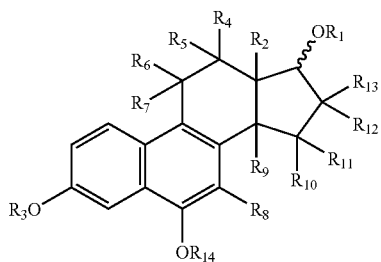

or pharmaceutically acceptable salts thereof,
wherein:
the bond represented by the wavy line may be a single or double bond such that when the wavy line is a single bond, $R_1$ is selected from the group consisting of hydrogen, sulfate and glucuronide or other esters, and when the wavy line is a double bond, $R_1$ does not exist;

$R_2$ is lower alkyl;

$R_3$ is selected from the group consisting of hydrogen, sulfate and glucuronide;

$R_4$ through $R_7$ and $R_{10}$ through $R_{13}$ may be the same or different and each represents hydrogen, hydroxy, ketone, lower alkyl, lower alkoxy, halogen, or carbonyl group;

$R_8$ and $R_9$ are independently selected from the group consisting of hydrogen, hydroxy, lower alkyl, lower alkoxy, halogen, and carbonyl groups; and $R_{14}$ is selected from the group consisting of hydrogen, sulfate and glucuronide;

said compound being present in chemically pure form; and (b) a pharmaceutically active ingredient selected from the group consisting of estrogenic compounds, androgenic compounds, progestin compounds, vasodilation agents, calcium salts, and vitamin D, and mixtures and combinations thereof.

11. The topical pharmaceutical formulation of claim 10, wherein the formulation is a vaginal cream.

12. The topical pharmaceutical formulation of claim 10, wherein the formulation is a gel.

13. The topical pharmaceutical formulation of claim 10, wherein the formulation is a suppository.

14. The topical pharmaceutical formulation of claim 10, wherein the formulation is a transdermal patch.

* * * * *